US012747421B2

(12) United States Patent
Fahmy et al.

(10) Patent No.: US 12,747,421 B2
(45) Date of Patent: Sep. 29, 2026

(54) COMPOSITIONS AND SYSTEMS FOR EX VIVO CELL MODULATION AND METHODS OF USE THEREOF

(71) Applicant: Yale University, New Haven, CT (US)

(72) Inventors: Tarek Fahmy, Middlefield, CT (US); Rabib Shahab Chaudhury, Nanuet, NY (US)

(73) Assignee: Yale University, New Haven, CT (US)

( * ) Notice: Subject to any disclaimer, the term of this patent is extended or adjusted under 35 U.S.C. 154(b) by 1502 days.

(21) Appl. No.: 17/054,115

(22) PCT Filed: May 9, 2019

(86) PCT No.: PCT/US2019/031494
§ 371 (c)(1),
(2) Date: Nov. 9, 2020

(87) PCT Pub. No.: WO2019/217661
PCT Pub. Date: Nov. 14, 2019

(65) Prior Publication Data

US 2021/0115378 A1 Apr. 22, 2021

Related U.S. Application Data

(60) Provisional application No. 62/669,213, filed on May 9, 2018.

(51) Int. Cl.
*A61K 40/11* (2025.01)
*A61K 40/42* (2025.01)
*C12M 1/00* (2006.01)
*C12M 1/12* (2006.01)
*C12N 5/0783* (2010.01)

(52) U.S. Cl.
CPC ............. *C12M 25/14* (2013.01); *A61K 40/11* (2025.01); *A61K 40/42* (2025.01); *C12M 23/20* (2013.01); *C12M 25/16* (2013.01); *C12N 5/0636* (2013.01)

(58) Field of Classification Search
CPC ...... C12M 25/14; C12M 23/20; C12M 23/06; A61K 39/4611; C12N 5/0636
See application file for complete search history.

(56) References Cited

U.S. PATENT DOCUMENTS

| | | | |
|---|---|---|---|
| 4,638,045 | A | 1/1987 | Kohn |
| 4,806,621 | A | 2/1989 | Kohn |
| 4,946,929 | A | 8/1990 | D Amore |
| 5,010,167 | A | 4/1991 | Ron |
| 5,019,379 | A | 5/1991 | Domb |
| 5,120,727 | A | 6/1992 | Kao |
| 5,162,333 | A | 11/1992 | Failli |
| 5,202,332 | A | 4/1993 | Hughes |
| 5,385,908 | A | 1/1995 | Nelson |
| 5,399,665 | A | 3/1995 | Barrera |
| 5,484,790 | A | 1/1996 | Failli |
| 5,512,600 | A | 4/1996 | Mikos |
| 5,514,378 | A | 5/1996 | Mikos |
| 5,530,006 | A | 6/1996 | Waranis |
| 5,559,112 | A | 9/1996 | Skotnicki |
| 5,567,709 | A | 10/1996 | Skotnicki |
| 5,696,175 | A | 12/1997 | Mikos |
| 5,716,404 | A | 2/1998 | Vacanti |
| 5,736,372 | A | 4/1998 | Vacanti |
| 5,770,417 | A | 6/1998 | Vacanti |
| 5,780,462 | A | 7/1998 | Lee |
| 5,804,178 | A | 9/1998 | Vacanti |
| 5,837,752 | A | 11/1998 | Shastri |
| 5,902,599 | A | 5/1999 | Anseth |
| 5,989,591 | A | 11/1999 | Nagi |
| 6,015,809 | A | 1/2000 | Zhu |
| 6,095,148 | A | 8/2000 | Shastri |
| 6,123,727 | A | 9/2000 | Vacanti |

(Continued)

FOREIGN PATENT DOCUMENTS

| | | |
|---|---|---|
| EP | 3315596 | 5/2018 |
| JP | 2007267673 | 10/2007 |

(Continued)

OTHER PUBLICATIONS

Bikiaris D. Microstructure and Properties of Polypropylene/Carbon Nanotube Nanocomposites. Materials (Basel). Apr. 21, 2010;3(4):2884â946. doi: 10.3390/ma3042884. PMCID: PMC5445858. (Year: 2010).*
Sharma S. et al. PLGA-based nanoparticles: A new paradigm in biomedical applications, TrAC Trends in Analytical Chemistry, vol. 80, p. 30-40. 2016 (Year: 2016).*
Andersen, et al., "A Response Calculus for Immobilized T Cell Receptor Ligands", J. Biol. Chem., 276(52):49125-32 (2001).
Apostolopoulos, et al., "Structural implications for the design of molecular vaccines", Curr. Opin. Mol. Ther., 2(1):29-36 (2000). Abstract Only.
Auffray, et al., "Isotypic and allotypic variation of human class II histocompatibility antigen α-chain genes", Nature, 308(5957):327-333 (1984).

(Continued)

*Primary Examiner* — Maria G Leavitt
*Assistant Examiner* — Vyoma Shubham Tiwari
(74) *Attorney, Agent, or Firm* — PABST PATENT GROUP LLP

(57) ABSTRACT

Bioreactor devices for modulating cells, systems including the devices, and methods of using the devices and systems to modulate cells are provided. The bioreactor devices typically include (i) a base support; (ii) a scaffold having bound to or present on the surface thereof, one or more cell receptor ligands; and (iii) a biodegradable polymer, co-polymer, or blend of polymers including an active agent associated with, encapsulated within, surrounded by, and/or dispersed therein. The systems include a bioreactor device, and one or more additional components, such as a housing for the device, one or more flow lines, one or more ports, one or more valves or clamps, etc. Methods of using the devices and systems for modulating cells ex vivo and treating subjects with cell adaptive therapy are also provided.

25 Claims, 16 Drawing Sheets

(56) References Cited

U.S. PATENT DOCUMENTS

| | | | |
|---|---|---|---|
| 6,506,577 B1 | 1/2003 | Deming | |
| 6,632,922 B1 | 10/2003 | Deming | |
| 6,686,446 B2 | 2/2004 | Deming | |
| 6,818,732 B2 | 11/2004 | Deming | |
| 8,658,178 B2 | 2/2014 | Fahmy | |
| 9,737,593 B2 | 8/2017 | Fahmy | |
| 2004/0232073 A1 | 11/2004 | Papadimitrakopoulos | |
| 2013/0216581 A1* | 8/2013 | Fahmy | A61K 39/4611 424/277.1 |
| 2015/0125384 A1 | 5/2015 | Mellman | |

FOREIGN PATENT DOCUMENTS

| | | | |
|---|---|---|---|
| WO | 9504738 | 2/1995 | |
| WO | 9516691 | 6/1995 | |
| WO | 9522972 | 8/1995 | |
| WO | 0001385 | 1/2000 | |
| WO | 0162895 | 8/2001 | |
| WO | 2013192532 | 12/2013 | |
| WO | WO-2013192532 A2 * | 12/2013 | A61K 39/0005 |

OTHER PUBLICATIONS

Barrera, et al., "Synthesis and RGD peptide modification of a new biodegradable copolymer: poly(lactic acid-co-lysine)", J. Am. Chem. Soc., 115(23):11010 (1993).

Bergmann, et al., "An endogenously synthesized decamer peptide efficiently primes cytotoxic T cells specific for the HIV-1 envelope glycoprotein", Eur. J. Immunol., 23(11):2777-2781 (1993).

Bergmann, et al., "Flanking residues alter antigenicity and immunogenicity of multi-unit CTL epitope", J. Immunol., 157:3242-3249 (1996).

Bianco, et al., "Applications of carbon nanotubes in drug delivery", Curr. Opin. Chem. Biol., 9(6):674-9 (2005).

Boussif, et al., "A versatile vector for gene and oligonucleotide transfer into cells in culture and in vivo: Polyethylenimine", Proc. Natl. Acad. Sci., USA, 92:7297 (1995).

Burke, et al., "The influence of adjuvant on the therapeutic efficacy of a recombinant genital herpes vaccine", J. Inf Dis., 170(5): 1110-19 (1994).

Chambers, et al., "Co-stimulation in T cell responses", Curr. Opin. Immunol., 9(3):396-404 (1997).

Das, et al., "Structure and nucleotide sequence of the heavy chain gene of HLA-DR", Proc. Natl. Acad. Sci. U.S.A., 80(12): 3543-3547 (1983).

Deming, et al., Facile synthesis of block copolypeptides of defined architecture, Nature, 390:386 (1997).

Engelhard, "Structure of peptides associated with MHC class I molecules", Curr. Opin. Immun., 6:13-23 (1994).

Fadel, et al., "A carbon nanotube-polymer composite for T-cell therapy", Nature Nanotechnology, 9(8):639-647 (2014b).

Fadel, et al., "Adsorption of Multimeric T Cell Antigens on Carbon Nanotubes: Effect on Protein Structure and Antigen-Specific T Cell Stimulation", Small, 9(5):666-672 (2013).

Fadel, et al., "Clustering of stimuli on single-walled carbon nanotube bundles enhances cellular activation", Langmuir, 26(8):5645-5654 (2010).

Fadel, et al., "Enhanced cellular activation with single walled carbon nanotube bundles presenting antibody stimuli", Nano letters, 8(7):2070-2076 (2008).

Fadel, et al., "Immunotherapy applications of carbon nanotubes: from design to safe applications", Trends in Biotechnology, 32(4):198-209 (2014a).

Feazell, et al., "Soluble Single-Walled Carbon Nanotubes as Longboat Delivery Systems for Platinum(IV) Anticancer Drug Design", J. Am. Chem. Soc., 129(27):8438-9 (2007).

Freeman, et al., "Engagement of the Pd-1 Immunoinhibitory Receptor by a Novel B7 Family Member Leads to Negative Regulation of Lymphocyte Activation", J. Exp Med., 192(7): 1027-1034 (2000).

Gonzalez, et al., "T cell receptor binding kinetics required for T cell activation depend on the density of cognate ligand on the antigen-presenting cell", Proc. Natl. Acad. Sci. U.S.A., 102(13):4824-9 (2005).

Grakoui, et al., "The immunological synapse: a molecular machine controlling T cell activation", Science, 285(5425):221-7 (1999).

Haensler, et al., "Polyamidoamine cascade polymers mediate efficient transfection of cells in culture", Bioconjugate Chem., 4(5):372 (1993).

Hemraj-Benny, et al., "Effect of ozonolysis on the pore structure, surface chemistry, and bundling of single-walled carbon nanotubes", Jour. Coll. Interj. Sci., 317(2):375-82 (2008).

Hentikoff, "Amino acid substitution matrices from protein blocks", Proc. Natl. Acad. Sci. U.S.A., 89(22):10915-10919 (1992).

Hu, et al., "Nitric Acid Purification of Single-Walled Carbon Nanotubes", Jour. Phys. Chem. B, 107(50): 13838-42 (2003).

International Search Report for PCT/US2019/031494 dated Aug. 2, 2019.

Itoh, et al., "Thymus and Autoimmunity: Production of CD25+ CD4+ Naturally Anergic and Suppressive T Cells as a Key Function of the Thymus in Maintaining Immunologic Self-Tolerance", J. Immunol., 162(9):5317-5326 (1999).

Kabanov, et al., "DNA Complexes with Polycations for the Delivery of Genetic Material into Cells", Bioconjugate Chem., 6(1):7-20 (1995).

Kam, et al., "Nanotube molecular transporters: internalization of carbon nanotube-protein conjugates into Mammalian cells", J. Am. Chem. Soc., 126(22):6850-1 (2004).

Karajanagi, et al., "Structure and function of enzymes adsorbed onto single-walled carbon nanotubes", Langmuir, 20(26):11594-9 (2004).

Kelly, et al., "Complete nucleotide sequence of a functional HLA-DP beta gene and the region between the DP beta 1 and DP alpha 1 genes: comparison of the 5' ends of HLA class II genes", Nucl. Acids Res., 13(5):1607-1621 (1985).

Kim, et al., "The ABCs of artificial antigen presentation", Nat. Biotechn., 22(4):403-10 (2004).

Kisielow, et al., "Tolerance in T-cell-receptor transgenic mice involves deletion of nonmature CD4+8+ thymocytes", Nature, 333(6175):742-746 (1988).

Kostelny, et al., "Formation of a bispecific antibody by the use of leucine zippers", J. Immunol., 148(5):1547-1553 (1992).

Krummel, et al., "CTLA-4 engagement inhibits IL-2 accumulation and cell cycle progression upon activation of resting T cells" J. Exp. Med., 183(6):2533-2540 (1996).

Kukowska-Latallo, et al., "Efficient transfer of genetic material into mammalian cells using Starburst polyamidoamine dendrimers", Proc. Natl. Acad. Sci., USA, 93(10):4897 (1996).

Kwon, et al., "Pseudopoly(amino acids): a study of the synthesis and characterization of poly(trans-4-hydroxy-N-acyl-L-proline esters)", Macromolecules, 22:3250 (1989).

Langer, et al., "Biomaterials in Drug Delivery and Tissue Engineering: One Laboratory's Experience", Acc. Chem. Res., 33(2):94-101 (2000).

Langer, et al., "Selected advances in drug delivery and tissue engineering", J. Control. Release, 62(1-2):7-11 (1999).

Lanzavecchia, "Mechanisms of antigen uptake for presentation", Curr. Opin. Immunol., 8(3):348-54 (1996).

Larhammar, et al., "Exon-intron organization and complete nucleotide sequence of a human major histocompatibility antigen DC beta gene", Proc. Natl. Acad. Sci. U.S.A., 80(23):7313-7317 (1983).

Latchman, et al., "PD-L2 is a second ligand for PD-1 and inhibits T cell activation", Nat Immunol., 2(3):261-8 (2001).

Lawrance, et al., "The genomic organisation and nucleotide sequence of the HLA-SB(DP) alpha gene", Nucleic Acids Res., 13(20):7515-7528 (1985).

Lenshow, et al., "CD28/B7 system of T cell costimulation", Annu. Rev. Immunol., 14:233-258 (1996).

Liang, et al., "A Convenient Route to Functionalized Carbon Nanotubes", Nano Lett., 4(7):1257-60 (2004).

Lim, et al., "A Self-Destroying Polycationic Polymer: Biodegradable Poly(4-hydroxy-l-proline ester)", J. Am. Chem. Soc., 121(24):5633 (1999).

(56) References Cited

OTHER PUBLICATIONS

Lim, et al., "Cationic hyperbranched poly(amino ester): a novel class of DNA condensing molecule with cationic surface, biodegradable three-dimensional structure, and tertiary amine groups in the interior", J. Am. Chem. Soc., 123(10):2460 (2001).
Miller, et al., "Self-Ignorance in the Peripheral T-Cell Pool", Immunol. Rev., 133:131-150 (1993).
Monks, et al., "Three-dimensional segregation of supramolecular activation clusters in T cells", Nature, 395(6697):82-6 (1998).
Moore, "Introduction of soluble protein into the class I pathway of antigen processing and presentation", Cell, 54(6):777-785 (1988).
Needleman, et al., "A general method applicable to the search for similarities in the amino acid sequence of two proteins", Mol. Biol., 48(3):443-453 (1970).
Oelke, et al., "Ex vivo induction and expansion of antigen-specific cytotoxic T cells by HLA-Ig-coated artificial antigen-presenting cells", Nat. Med., 9(5):619-24 (2003).
Ouyang, et al., "Fundamental electronic properties and applications of single-walled carbon nanotubes", Acc. of Chem. Res., 35(12):1018-25 (2002).
Pantarotto, et al., "Synthesis, structural characterization, and immunological properties of carbon nanotubes functionalized with peptides", J. Am. Chem. Soc., 125(20):6160-4 (2003).
Pantarotto, et al., "Translocation of bioactive peptides across cell membranes by carbon nanotubes", Chem. Commun., 1:16-7 (2004).
Papisov, "Acyclic Polyacetals from Polysaccharides: Biomimetic Biomedical "Stealth" Polymers", ACS Symposium Series, 786:301-304 (2001).
Prakken, et al., "Artificial antigen-presenting cells as a tool to exploit the immune 'synapse'", Nat. Med., 6(12):1406-10 (2000).
Putnam, et al., "Poly(4-hydroxy-l-proline ester): Low-Temperature Polycondensation and Plasmid DNA Complexation", Macromolecules, 32(11):3658-3662 (1999).
Raker, et al., "Tolerogenic Dendritic Cells for Regulatory T Cell Induction in Man", Front Immunol., 6:569 (2015).
Rathmell, et al., "The Central Effectors Of Cell Death In The Immune System", Annu. Rev. Immunol., 17:781-828 (1999).
Rocha, et al., "Peripheral selection of the T cell repertoire", Science, 251(4998):1225-1228 (1991).
Sakaguchi, et al., "Immunologic self-tolerance maintained by activated T cells expressing IL-2 receptor alpha-chains (CD25). Breakdown of a single mechanism of self-tolerance causes various autoimmune diseases", J. Immunol., 155(3):1151-1164 (1995).
Schwartz, "A cell culture model for T lymphocyte clonal anergy", Science, 248:1349-1356 (1990).
Shastri, "Needles in haystacks: identifying specific peptide antigens for T cells", Curr. Opin. Immunol., 8(2):271-7 (1996).
Shawar, et al., "Antigen presentation by major histocompatibility complex class I-B molecules", Annu. Rev. Immunol., 12:839-880 (1994).
Shimizu, et al., "Induction of Tumor Immunity by Removing CD25+CD4+ T Cells: A Common Basis Between Tumor Immunity and Autoimmunity", J. Immunol., 163:5211-5218 (1999).
Sitharaman, et al., "Superparamagnetic gadonanotubes are high-performance MRI contrast agents", Chem. Commun., (31):3915-7 (2005).
Sojka, et al., "Mechanisms of regulatory T-cell suppression—a diverse arsenal for a moving target", Immunology, 124:13-22 (2008).
Songsivilai, et al., "Bispecific antibody: a tool for diagnosis and treatment of disease", Clin. Exp. Immunol., 79(3):315-321 (1990).
Steenblock, et al., "An artificial antigen-presenting cell with paracrine delivery of IL-2 impacts the magnitude and direction of the T cell response", The Journal of Biological Chemistry, 286(40):34883-34892 (2011).
Stenger, et al., "Dendritic cells and regulation of graft-versus-host disease and graft-versus-leukemia activity", Blood, 119(22):5088-5103 (2012).
Suhrbier, "Multi-epitope DNA vaccines", Immunol. and Cell Biol., 75(4):402-408 (1997).
Takahashi, et al., "Immunologic self-tolerance maintained by CD25+ CD4+ naturally anergic and suppressive T cells: induction of autoimmune disease by breaking their anergic/suppressive state", Int. Immunol., 10(12):1969-1980 (1998).
Tang, et al., "In vitro gene delivery by degraded polyamidoamine dendrimers", Bioconjugate Chem., 7(6):703-14 (1996).
Tigges, et al., "Human herpes simplex virus (HSV)-specific CD8+ CTL clones recognize HSV-2-infected fibroblasts after treatment with IFN-gamma or when virion host shutoff functions are disabled", J. Immunol., 156(10):3901-3910 (1996).
Tonnelle, et al., "DO beta: a new beta chain gene in HLA-D with a distinct regulation of expression", EMBO J., 4(11):2839-2847 (1985).
Townsend, et al., "Antigen recognition by class I-restricted T lymphocytes", Annu. Rev. Immunol., 7:601-624 (1989).
Uhrich, et al., "Polymeric systems for controlled drug release", Chem. Rev., 99:3181 (1991).
Walunas, et al., "CTLA-4 ligation blocks CD28-dependent T cell activation", J. Exp. Med., 183(6):2541-2550 (1996).
Wang, et al., "A Novel Biodegradable Gene Carrier Based on Polyphosphoester", J. Am. Chem. Soc., 123(38):9480 (2001).
Wang, et al., "Vertically oriented single-wall carbon nanotube/enzyme on silicon as biosensor electrode", Journal of the Minerals, 57:27-29 (2005).
Watson, et al., "Differential Effects of Costimulatory Pathway Modulation on Corneal Allograft Survival", Invest Ophthalmol Vis Sci., 47(8):3417-22 (2006).
Williams, et al., "Carbon nanotubes with DNA recognition", Nature, 420(6917):761 (2002).
Yewdell, et al., "Cell biology of antigen processing and presentation to major histocompatibility complex class I molecule-restricted T lymphocytes", Adv. in Immunol., 52:1-123 (1992).
Youngnak et al., "Differential binding properties of B7-H1 and B7-DC to programmed death-1", Biochem Biophys Res Comm., 307(3):672-677 (2003).
Zauner, et al., "Polylysine-based transfection systems utilizing receptor-mediated delivery", Adv. Drug Del. Rev., 30:97-113 (1998).
Zhou, et al., "Preparation of poly(L-serine ester): a structural analog of conventional poly(L-serine)", Macromolecules, 23(14):3399-3406 (1990).

* cited by examiner

COMPOSITIONS AND SYSTEMS FOR EX VIVO CELL MODULATION AND METHODS OF USE THEREOF

CROSS REFERENCE TO RELATED APPLICATIONS

This application is a National Phase application under 35 U.S.C. § 371 of PCT/US2019/031494, filed May 9, 2019, which claims priority to and the benefit of U.S. Provisional Application No. 62/669,213, filed May 9, 2018, which are hereby incorporated herein by reference in their entirety.

FIELD OF THE INVENTION

The present disclosure generally relates to the field of bioreactor devices that can be used at a patient's bedside or in a doctor's office and methods for making and using them.

BACKGROUND OF THE INVENTION

T cells are central players in initiating and maintaining immune responses. An important goal of successful immunotherapy is the stimulation of T cell immune responses against targets of interest such as tumors. This can be accomplished in two ways: 1) through immunization with tumor antigens or 2) by isolation of T cells specific to tumor antigens, and expansion of this population outside the body followed by re-transfer into the patient (adoptive transfer immunotherapy).

Some of the most encouraging data regarding immunotherapy come from studies employing adoptive transfer of tumor reactive T cells. Adoptive T cell transfer is an elegant approach to the treatment of infectious and malignant diseases. This therapeutic method involves the ex vivo expansion of T cells, which may be infused into patients to bolster the natural immune response. For example, expanded tumor-specific T cells have been shown to strengthen patient's immune responses to melanoma by infiltrating the tumor site and inducing tumor shrinkage. Researchers have also demonstrated that the adoptive transfer of T cells is a viable therapeutic approach to treating Epstein-Barr virus (EBV) as well as human immunodeficiency virus (HIV)-related infections. Thus, adoptive T cell transfer has potential applications in the treatment of both infectious diseases and cancer.

Despite the successes of these studies, adoptive T cell transfer by clonal expansion limited clinically because it does not consistently generate therapeutic numbers of T cells. This shortcoming has prompted the development of an alternative techniques for ex vivo T cell expansion, using artificial antigen presentation to T cells (Prakken, et al., *Nat. Med.,* 6(12):1406-10 (2000); Oelke, et al., *Nat. Med.,* 9(5): 619-24 (2003); Kim, et al., *Nat. Biotechn.,* 22:403-10 (2004)). The development of artificial APCs (aAPCs) is a new effort to generate a reproducible, "off-the shelf" means of stimulating and expanding T cells. Several types of aAPCs have been developed, including nonspecific bead-based systems that are currently used in many research laboratories to sustain the long-term expansion of $CD8^+$ T cells (Oelke, et al., *Nat. Med.,* 9(5):619-24 (2003); Kim, et al., *Nat. Biotechn.,* 22:403-10 (2004)).

Specific expansion of T cells outside the body depends however on efficient methods for displaying protein ligands that stimulate those cells. Ultimately, T cell stimulus intensity depends on the density of bound receptors in the contact area with a surface (Andersen, et al., *J. Biol. Chem.,* 276 (52):49125-32 (2001); Gonzalez, et al., *Proc. Natl. Acad. Sci. U.S.A.,* 102(13):4824-9 (2005)). Regions with a high density of T cell antigen receptors have been termed activated clusters because they are critical for T cell stimulation (Grakoui, et al., *Science,* 285(5425:221-7 (1999); Monks, et al., *Nature,* 395(6697):82-6 (1998)). The presence of such high density clusters has also been shown to accelerate T cell activation (Gonzalez, et al., *Proc. Natl. Acad. Sci. U.S.A.,* 102(13):4824-9 (2005)). In the lymph node, the primary site for T cell stimulation, antigen presenting cells are thought to concentrate the presentation of T cell stimuli by trafficking in a dense architectural scaffolding in close proximity to T cells.

In recent years, the principles of nanoassembly and biomimicry or physiological organ or cell emulation have advanced and provided a better understanding of biological processes (Fadel, et al. *Trends in Biotechnology,* 32, 198-209 (2014), Fadel, et al., *Small,* 9, 666-672 (2013), Fadel, et al., *Langmuir,* 26, 5645-5654 (2010), Fadel, et al., *Nature Nanotechnology,* 9, 639-647 (2014), Fadel, et al., *Nano letters,* 8, 2070-2076 (2008), Steenblock, et al., *The Journal of Biological Chemistry,* 286, 34883-34892 (2011)). However, there remains a need for improved clinical implementations of these exciting advances.

It is therefore an object of the invention to provide compositions and devices for ex vivo cell activation and expansion.

It is object of the invention to provide methods of making compositions and devices for ex vivo cell activation and expansion.

It is an objection of the invention to provide methods of ex vivo cell activation and expansion.

SUMMARY OF THE INVENTION

A device and method have been developed to produce potent T cells without genetic engineering, for example, CAR-T cells. This is achieved through the design of the device to resemble a natural environment for T cell modulation and growth. Expanded cells are more potent, without genetic engineering.

The device can be utilized bedside for T cell modulation and expansion. The ex vivo antigen-specific T cell potency and enrichment can be greatly facilitated by the use of nanoscale modules assembled into a macro medical device, referred to as a "bioreactor" unit, that is facile to use and easily deployed in any clinical setting. This bioreactor produces potent T cells within 3-10 days at 37° C. for treatment of tissue and blood malignancies as well as autoimmune disease.

In the body, T cells are known to expand rapidly, within 3-5 days following an infection, not weeks, as is currently the conventional procedure for expanding cells outside the body. In the body this is done with minute amounts of growth factors (Interlukin-2, produced in vivo and localized in the region where expansion of T cells is taking place). This region of the body is a very tortuous, high surface to volume environment, with laminar flow and local presentation of other stimuli beyond growth factors. This place is known as the secondary lymphoid organ or the lymph nodes and is an optimal structure for producing and expanding potent antigen-specific T cells.

The bioreactor is a disposable, T cell biome structure that functions like a lymph node outside the body, but works like a healthy in vivo lymph node to emulate an in vivo biological organ, the lymph node, for increasing the potency and number of immune cells who traffic, crosstalk, and develop for induction and maintenance of the defense system against viruses, bacteria, cancer, and even our own organs (as in autoimmune diseases such as diabetes, lupus, multiple sclerosis, etc.). The device provides the proper architecture, signal cues and operational conditions to produce T cells that are naturally potent against specific (peptide/MHC) or non-specific (CD3) antigens. It is a small device that can be employed in any clinical setting, that can attach to any IV line and can be stored at room temperature or higher (if needed).

The bioreactor devices typically include (i) a base support; (ii) a scaffold having bound to or present on the surface thereof, one or more ligands; and (iii) a biodegradable polymer, co-polymer, or blend of polymers including an active agent associated with, encapsulated within, surrounded by, and/or dispersed therein.

The base support is typically a high strength material, a high wicking material, or a combination thereof. The base support is typically porous. The pores can be, for example, between about 100 μm and 1,200 μm, such as between 200 μm and 1,200 μm, preferably between about 100 μm and 800 μm, most preferably between about 100 μm and about 500 μm, such as about 500 μm, in average diameter. The size of pores can heterogeneous or homogeneous. An exemplary base support material is a thermoplastic, preferably a semicrystalline thermoplastic, such as polypropylene.

The scaffold is a high surface area material and can also be porous. Exemplary scaffold materials include graphene, metallic nanoparticles, and metallic microparticles, or a pore glass system. In some embodiments, the scaffold is formed of carbon nanotubes, preferably bundled carbon nanotubes. The carbon nanotubes can be single-walled or multi-walled. In some embodiments the nanotubes are oxidized. One or more ligands for cell modulation can be adsorbed or otherwise functionalized on the surface of the scaffold. The ligand or ligands are selected based on the cell type for which modulation is desired. Preferred cells include, but are not limited to, T cells and antigen presenting cells including dendritic cells and macrophage.

Exemplary T cell ligands include receptor activators including adhesion molecules; polyclonal T cell activators such as mitogenic lectins concanavalin-A (ConA), phytohemagglutinin (PHA), pokeweed mitogen (PWM), and antibodies that crosslink the T cell receptor/CD3 complex; antigen-specific T cell activators, such as MHC molecules bound to peptide antigens; and co-stimulatory molecules such as CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor, a ligand that specifically binds with B7-H3, antibodies that specifically bind with CD27, CD28, 4-1BB, OX40, CD30, CD40, PD-1, ICOS, lymphocyte function-associated antigen-1 (LFA-1), CD2, CD7, LIGHT, NKG2C, or B7-H3, a ligand that specifically binds with CD83, and variants and fragments thereof.

In some embodiments, particularly those in which tolerance or a reduction in an active immune response is desire, the ligands can include immune checkpoint regulators such as PD-1 and/or CTLA-4 ligands that down-regulate the T cells and promote self tolerance by suppressing T cell inflammatory activity.

In some embodiments, the ligands are linked to the scaffold by an adaptor. For example, in some embodiments the adaptor is a pair of affinity molecules such as biotin-neutravidin. In an exemplary embodiment, neutravidin is adsorbed on the surface of the scaffold and the biotin is conjugated to the T cell ligands. When the biotinylated ligands are contacted with the avidin-functionalized scaffold, the scaffold becomes functionalized with the ligands.

The polymer or polymers are typically biodegradable. Exemplary polymers include, for example, polylactic acid, polyglycolic acid, polylactide-co-glycolide, or a combination thereof. In some embodiments, the polymers are in the form of nanoparticles adsorbed or otherwise functionalized on the surface of the scaffold. In some embodiments, the polymer is in the form of a layer adsorbed onto or otherwise coated onto at least one surface of the base support. For example, when the solvent from a liquid-applied polymer evaporates, the polymer can be left, and harden, in the pores of the porous substrate. After solvent evaporation, the biodegradable polymer is ready to release the embedded active agents in aqueous environments because the polymer. In some embodiments, the polymer is non-biodegradable, which can be advantageous in preventing build up on monomers in the device. Even with non-biodegradable polymer, the aqueous environment of the device in-use will enhance diffusivity of the active agent from the polymer.

The scaffold can be embedded in the polymer layer, or adsorbed onto the surface of the base support.

Active agents include immunomodulators such as cytokines, particularly growth factors such as IL-2, IL-21, IL-23, IL-17 for immune activating embodiments. In some embodiments, such as autoimmune applications, the cytokines can be, for example, IL-10, TGFbeta, +IL-2, and combinations thereof, particularly TGFbeta and IL-2 The active agents may be embedded in the scaffold at an amount between about 0.1 ng per 10 square microns and 100 ng per 10 square microns, preferably between about 10 ng per 10 square microns and 50 ng per 10 square microns, most preferably about 20 ng per 10 square microns.

Systems including the device are also provided. The systems include a bioreactor device, and one or more additional components, such as a housing for the device, one or more flow lines, one or more ports, one or more valves or clamps, etc. In some embodiments, the housing is gas permeable. The bioreactor device can be rolled-up and/or compressed inside the housing. In some embodiments, the housing is connected to two flow lines, wherein at least one of flow lines is connectable to a subject in need of treatment.

Methods of using the devices and systems for modulating cells ex vivo are also provided. For example, in some embodiments, T cells are contacted with a bioreactor device ex vivo for an effective amount of time to activate the T cells. The contacting can be, for example, from 1 to 5 days.

Methods of using ex vivo modulated cells for adoptive therapy can include administering a subject in need thereof with an effective amount of the ex vivo modulated cells. In some embodiments, the subject has cancer or an infection and the adaptive therapy treats the cancer or infection. Thus, methods of treating cancer and infections area also provided.

In some embodiments, the methods include connecting a subject in need of adaptive therapy to a system, drawing blood from the subject into the system, contacting the blood with the bioreactor device for an effective amount of time to active the cells, and returning the cells to the subject. In some embodiments, the system is disconnected for the subject for at least part of the time between drawing blood and returning the cells to the subject. The period of time can be, for example, 1-5 days.

Biotin-anti-CD3 and biotin anti-CD28 were added at equimolar concentrations to all substrates. The graph shows that the scaffold configuration is the most efficient at T cell activation and leads to phenotypically better activated T cells (higher CD25 expression, equivalent levels of CD44 and higher IFNg and IL-2 cytokine secretion from cells incubated with the various configurations. The anti-inflammatory cytokine, IL-10 levels, are low and similar in all systems, reflecting an enhancement, primarily, in pro-inflammatory signals.

Figure 9:
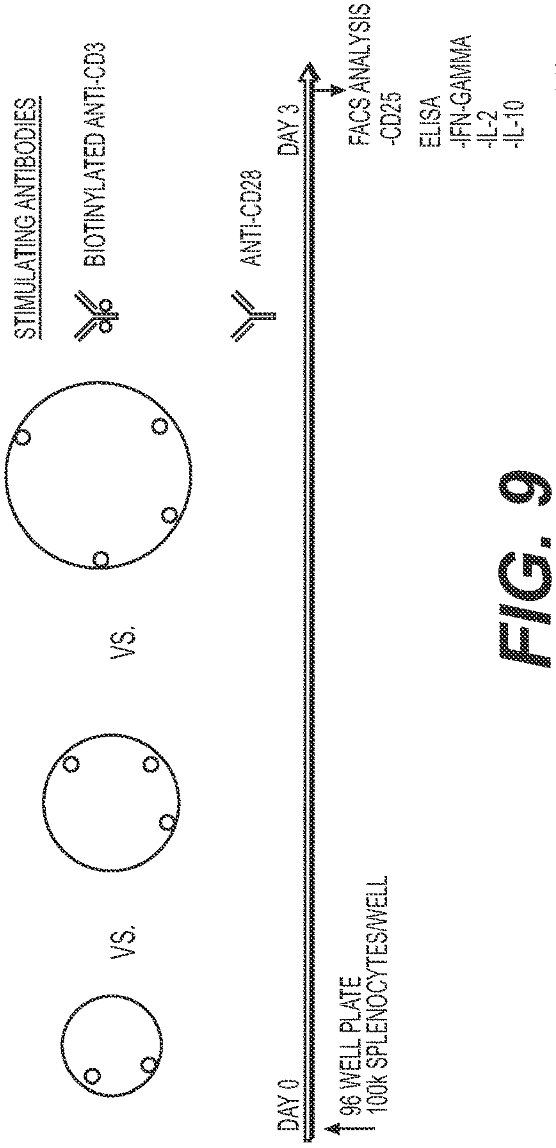
Figure 10A:
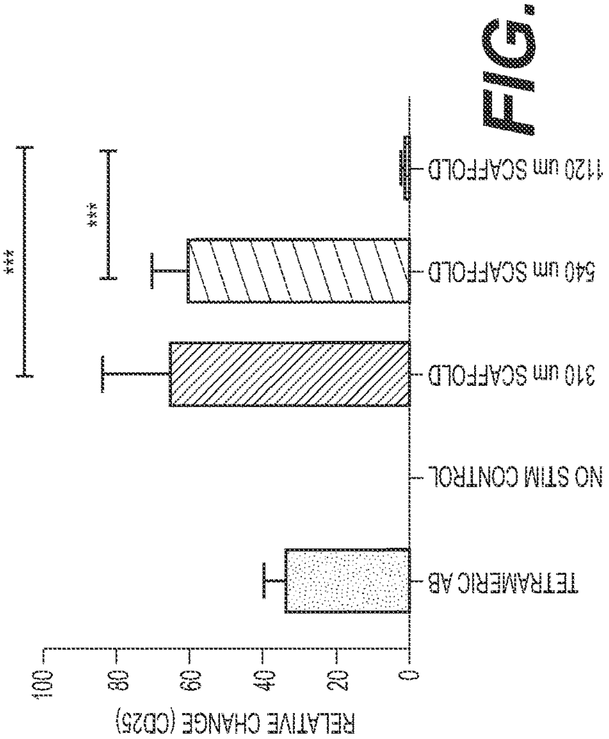
Figure 10B:
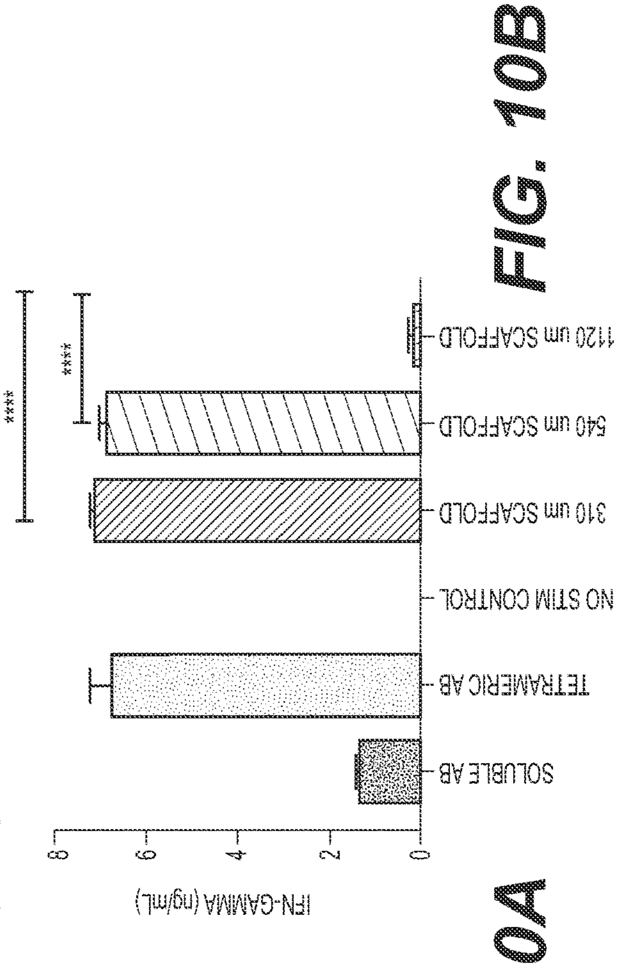
Figure 10C:
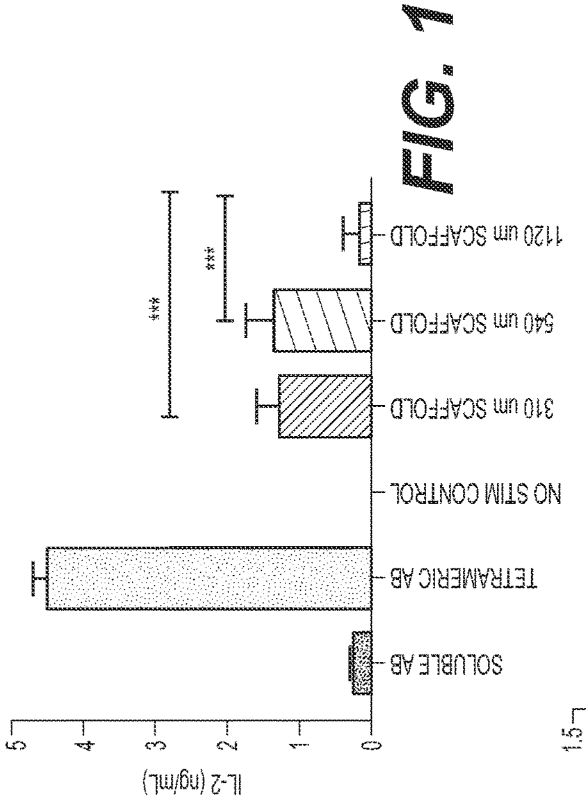
Figure 10D:
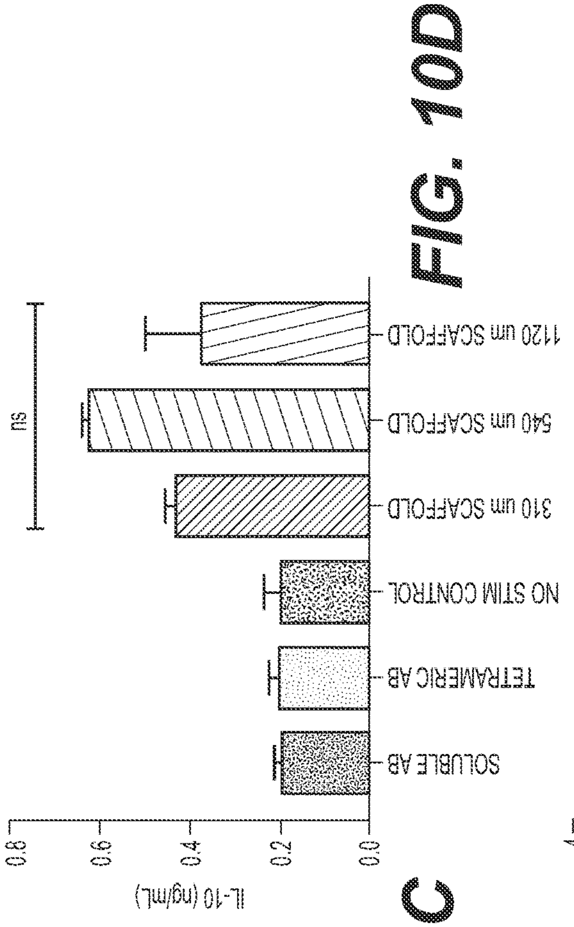
Figure 11A:
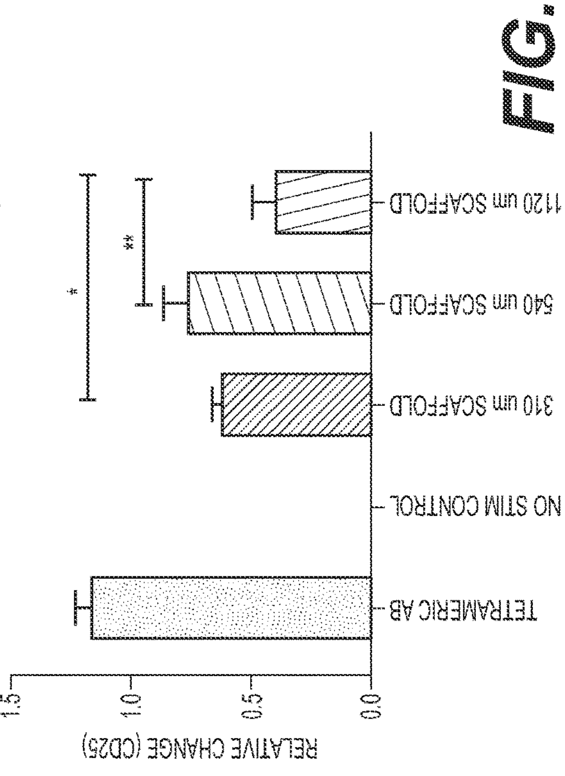
Figure 11B:
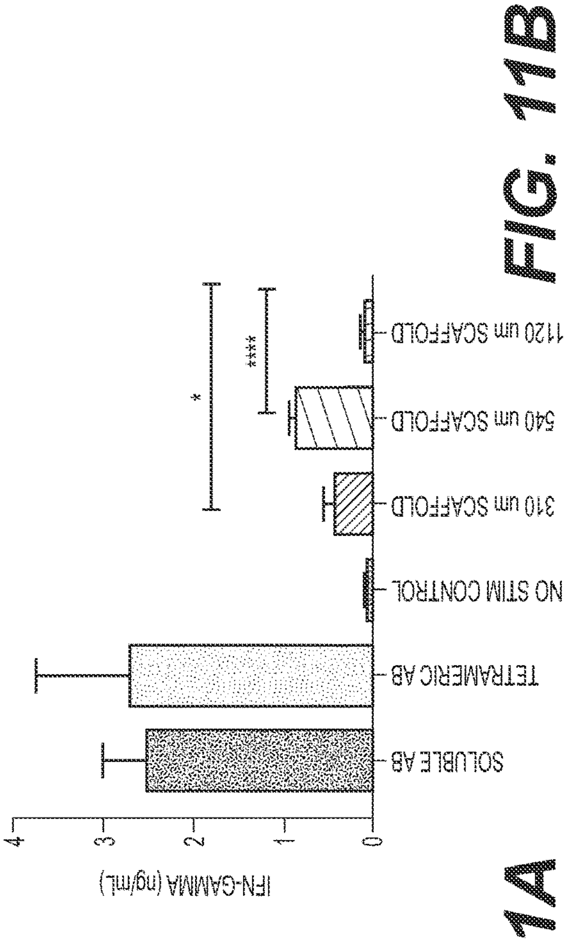
Figure 11C:
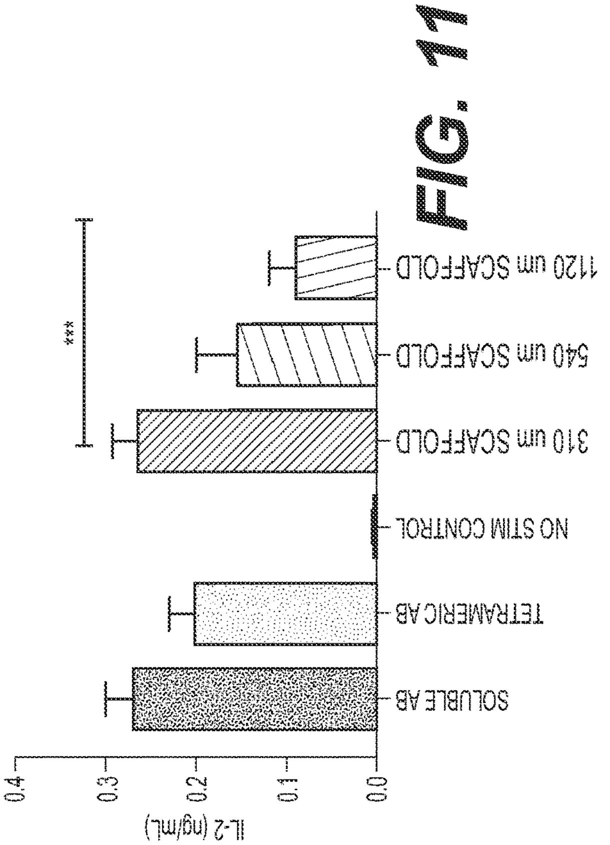
Figure 11D:
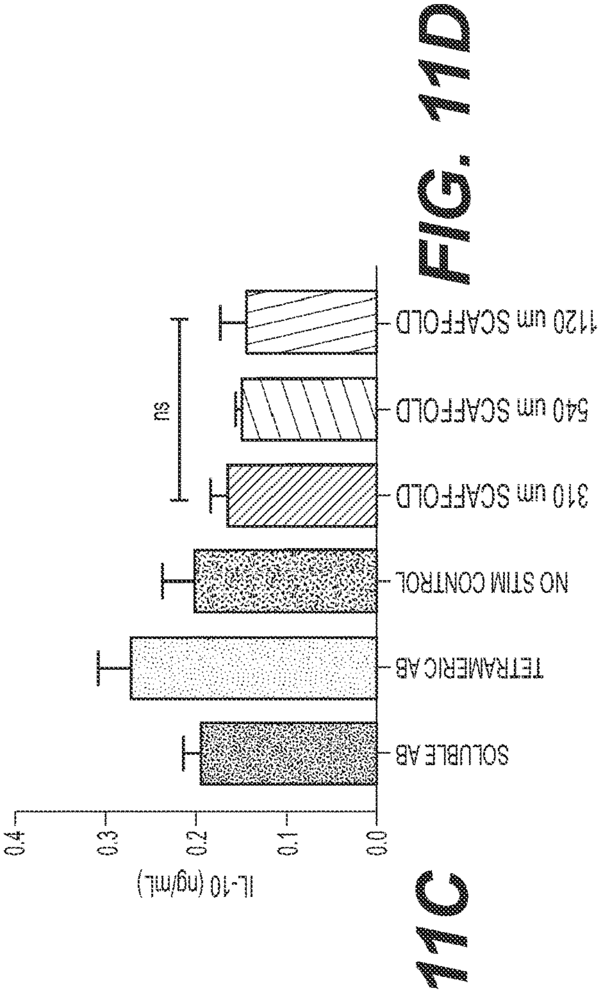

FIG. 9 is an illustration of an assay designed to test the effect of pore size of the core polypropylene substrate on the activation of T cells and the effect of pore size on proximity of stimulatory signals with fixed-costimulatory signals. Here co-stimulation was fixed at 2.5 ug/ml and anti-CD3 was also fixed at 5 ug/ml. As such the different pore sizes can impact the clustering of stimuli and hence the activation profile. Porosity was varied by inert gas-porogen flowrate during scaffold formulation. Porosity range is 300-1100 nm. Scaffolds were tethered with neutravidin at the same concentration then incubated with equimolar concentrations of anti-CD3 and anti CD28 (5 ug ml, 2.5 ug/ml, respectively). The results show that quality of activation is a strong function of the material porosity which allows for clusters of T cells to form and hence increase activation. Depending on the porosity the activation profile, cytokine secretion can be tailored to produce cells with different phenotypic activation profiles. All culture conditions were performed in RPMI medium 1650 supplemented with 10% FBS with no IL-2 added.

FIGS. 10A-10D show the impact of scaffold porosity on T cell activation (Surface markers). Ligand density in the pores is affected by pore size and may play a significant role in T cell activation and hence expansion. Bar graphs showing relative change in CD25 expression (10A), IFN-gamma secretion (ng/ml) (10B), IL-2 secretion (ng/ml) (10C), and IL-10 secretion (ng/ml) (10D) for splenocytes incubated with soluble Ab, tetrameric Ab, no stimulation control, and scaffolds with 310 μm, 540 μm, or 1120 μm pores (antibody concentration of 5 μg).

FIGS. 11A-11D Impact of porosity (Cytokine secretion from T cells). are bar graphs showing relative change in CD25 expression (11A), IFN-gamma secretion (ng/ml) (11B), IL-2 secretion (ng/ml) (11C), and IL-10 secretion (ng/ml) (11D) for splenocytes incubated with soluble Ab, tetrameric Ab, no stimulation control, and scaffolds with 310 μm, 540 μm, or 1120 μm pores (antibody concentration of 0.5 μg).

Figure 12:
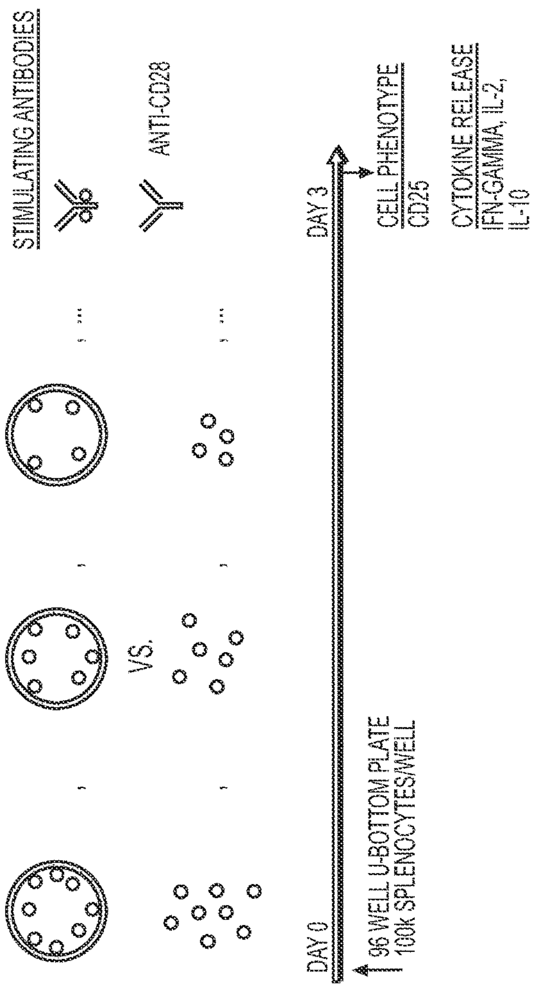
Figure 13A:
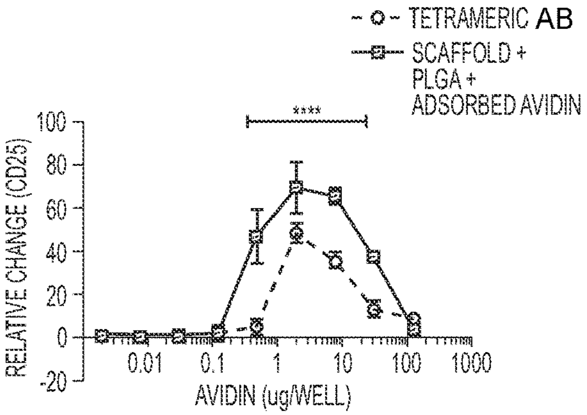
Figure 13B:
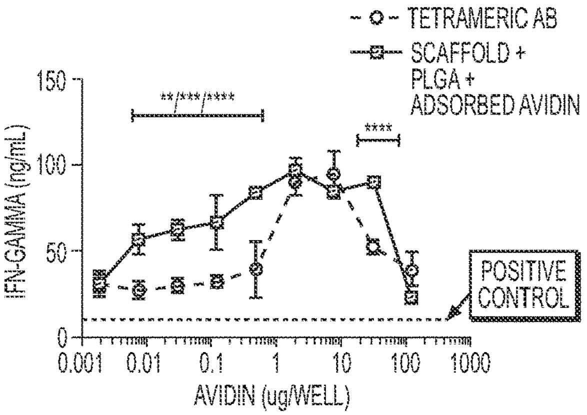
Figure 13C:
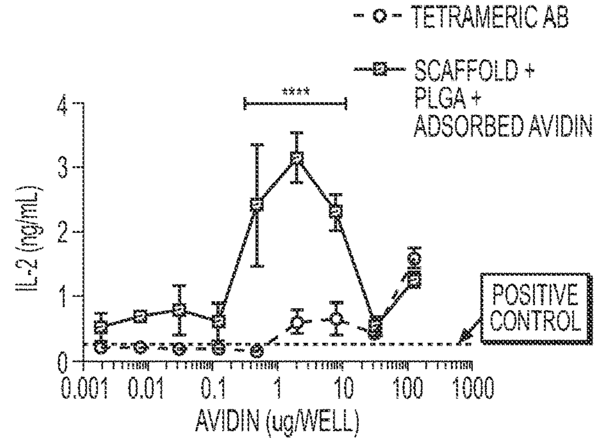
Figure 13D:
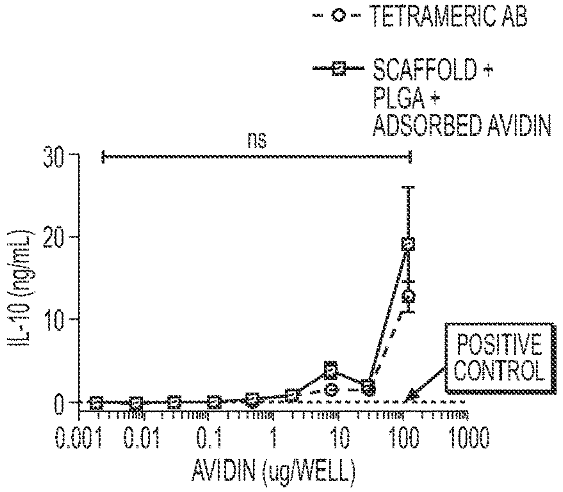

FIG. 12 Impact of ligand density on the scaffold on T cell stimulation. Another strategy to vary ligand density is by direct changes in the concentration of the tethered stimulus concentration. Here anti-CD3 and anti-CD28 biotin were varied from 0.5-5 ug/ml. The figure is an illustration of an assay designed to test the influence of density of T cell activating signals on T cell activation FIGS. 13A-13D Impact of ligand density (Surface markers). Bar graphs showing relative change in CD25 expression (13A), IFN-gamma secretion (ng/ml) (13B), IL-2 secretion (ng/ml) (13C), and IL-10 secretion (ng/ml) (13D) for splenocytes incubated with tetrameric Ab and scaffolds at various antibody densities. The figure shows that optimal activation occurs at an optimal concentration of presented ligands (between 1-10 ug/ml) and the quality of activation (i.e., minimal IL-10 levels) is best achieved at lower stimulus concentrations below 100 ug/ml.

Figure 14:
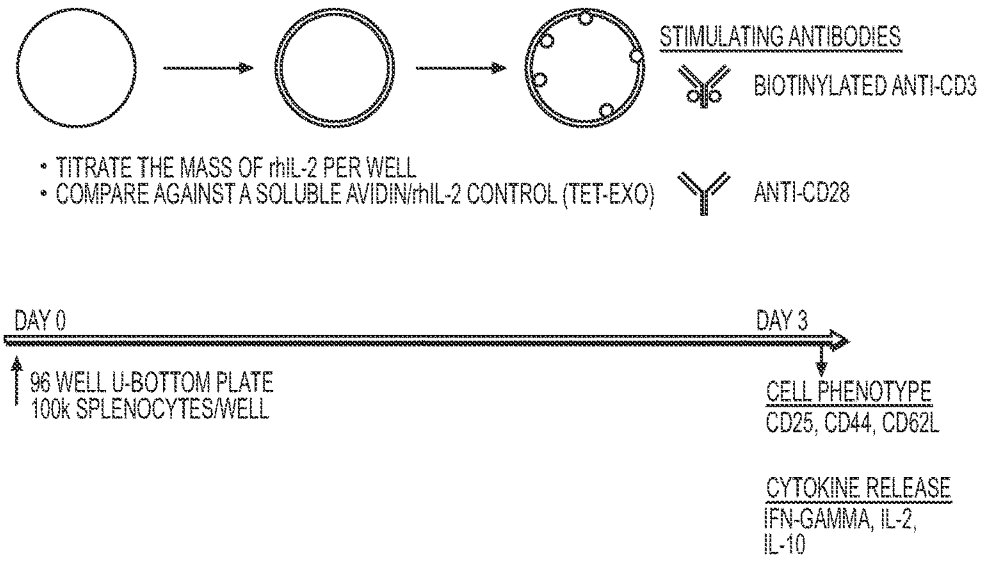
Figure 15A:
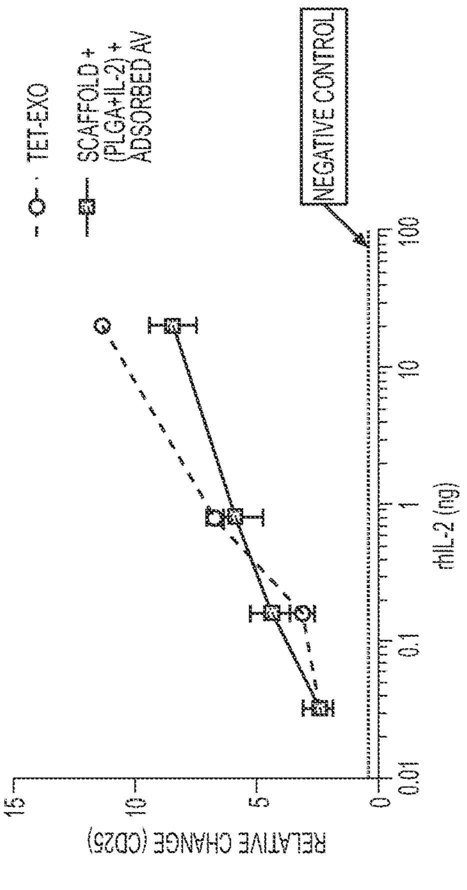
Figure 15B:
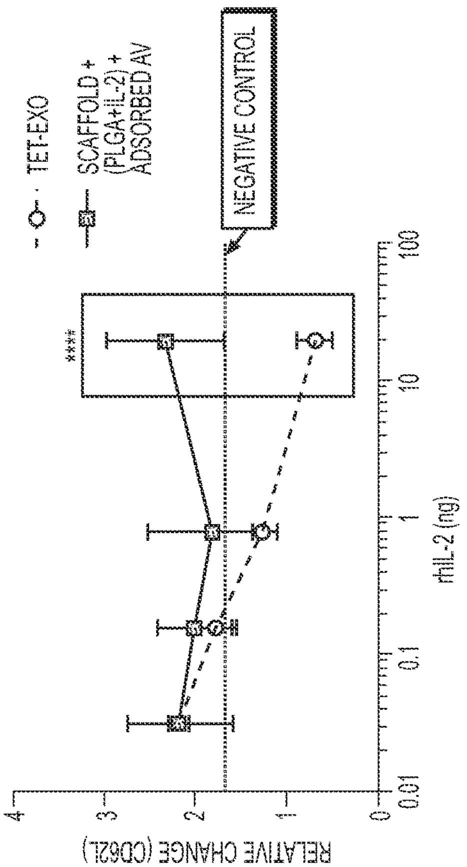
Figure 15C:
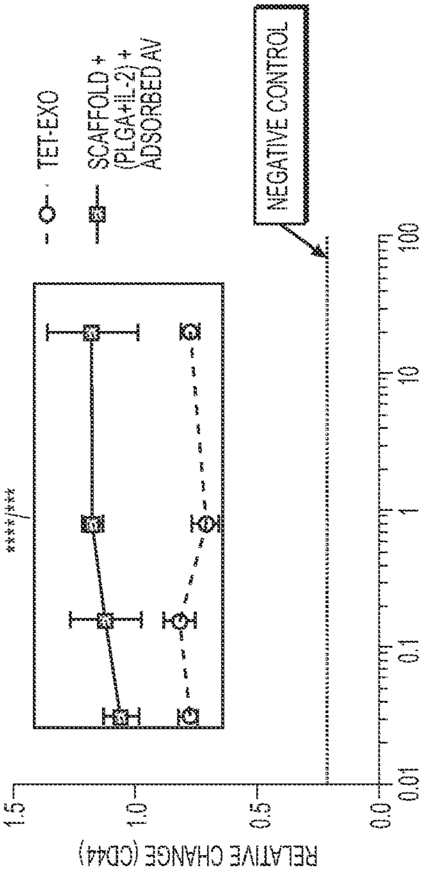
Figure 15D:
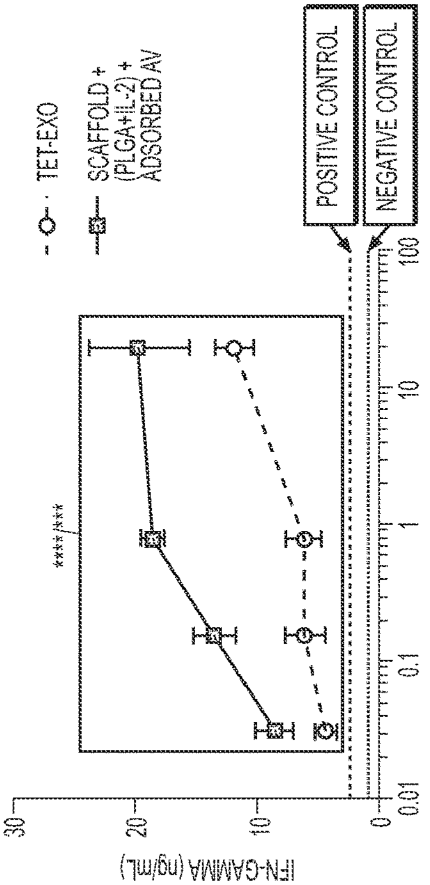
Figure 15E:
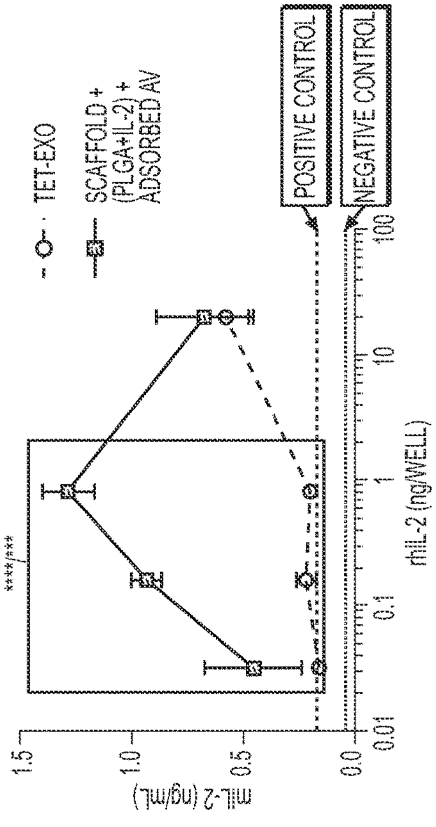
Figure 15F:
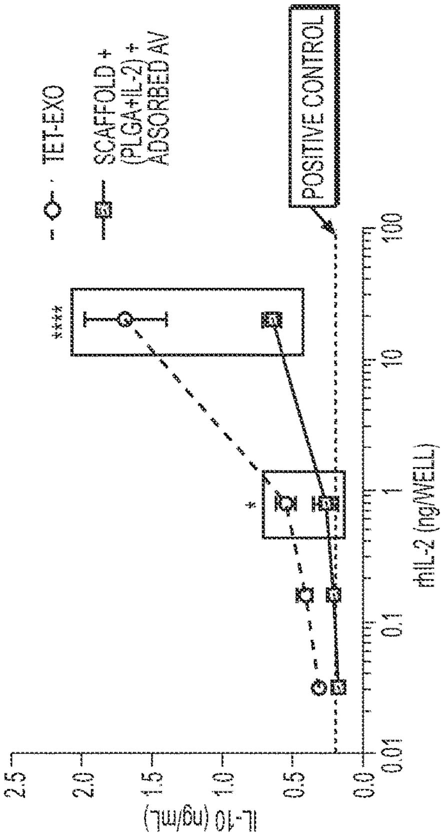

FIG. 14 is an illustration of an assay designed to test the impact scaffold-releasing different IL-2 levels on T cell activation. Human IL-2 was encapsulated in a PLGA coating on the scaffold (human IL-2 is cross-reactive with mouse T cells). The encapsulated amount was varied from 0.01 to 10 ng/well. 100% of the IL-2 was adsorbed in the PLGA coating during formulation and there were no washing steps.

FIGS. 15A-15F Impact of scaffold IL-2 on T cell activation. Bar graphs showing relative change in CD25 expression (15A), relative change in CD62L expression (15B), relative change in CD44 expression (15C), IFN-gamma secretion (ng/ml) (15D), mIL-2 secretion (ng/ml) (15E), and IL-10 secretion (ng/ml) (15F) for splenocytes incubated with tet-exo (tetrameric antibody and exogenous IL-2) and scaffolds with adsorbed avidin and rhIL-2 at various concentrations impregnated into a PGLA polymer layer for sustained release. Note maximal activation as assessed by mouse IL-2 secretion from activated cells and IFNg levels is achieved with paracrine release of human IL-2 from scaffolds. This effect was not recapitulated with soluble IL-2 and positive controls (highest level of IL-2) in soluble form did not achieve a similar effect. Negative controls are no IL-2 addition.

Figure 16:
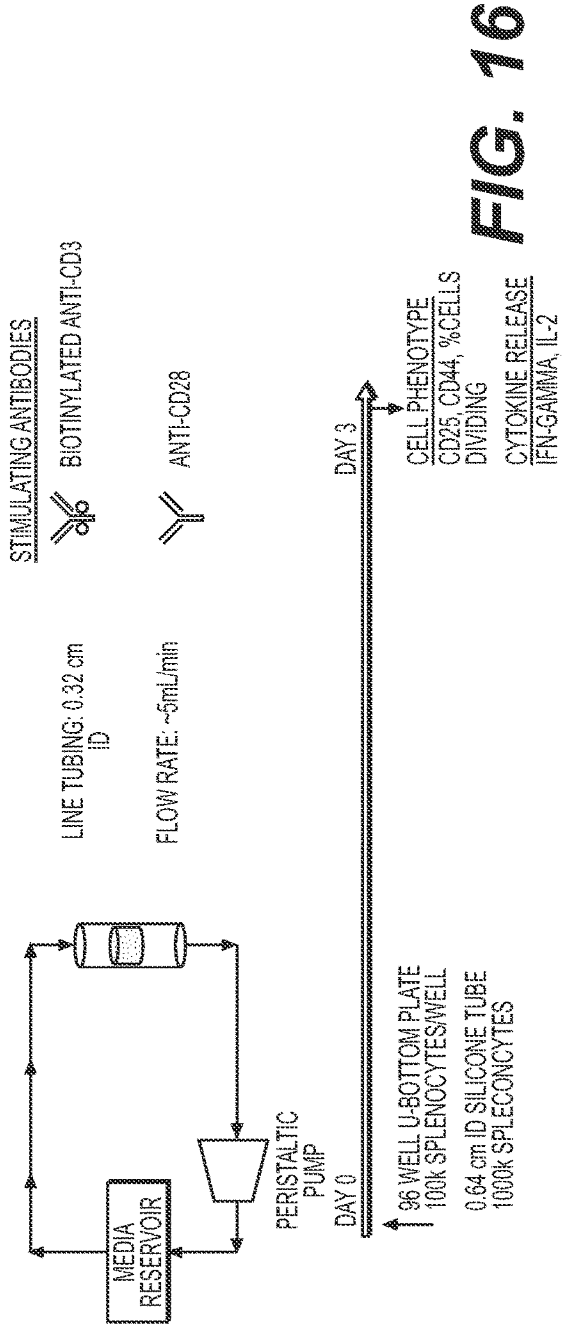
Figure 17A:
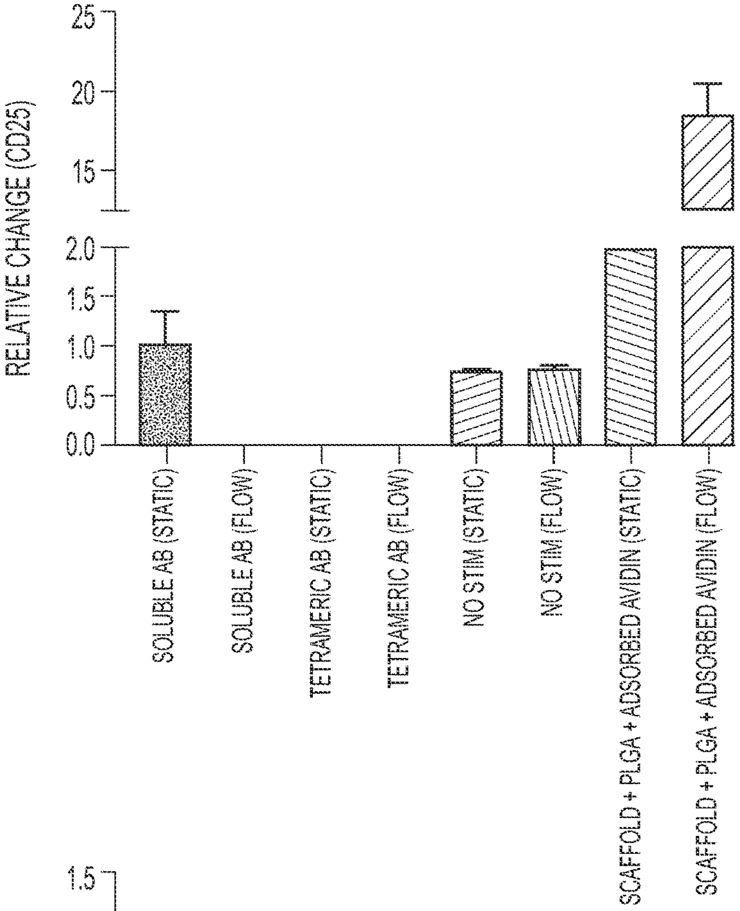
Figure 17B:
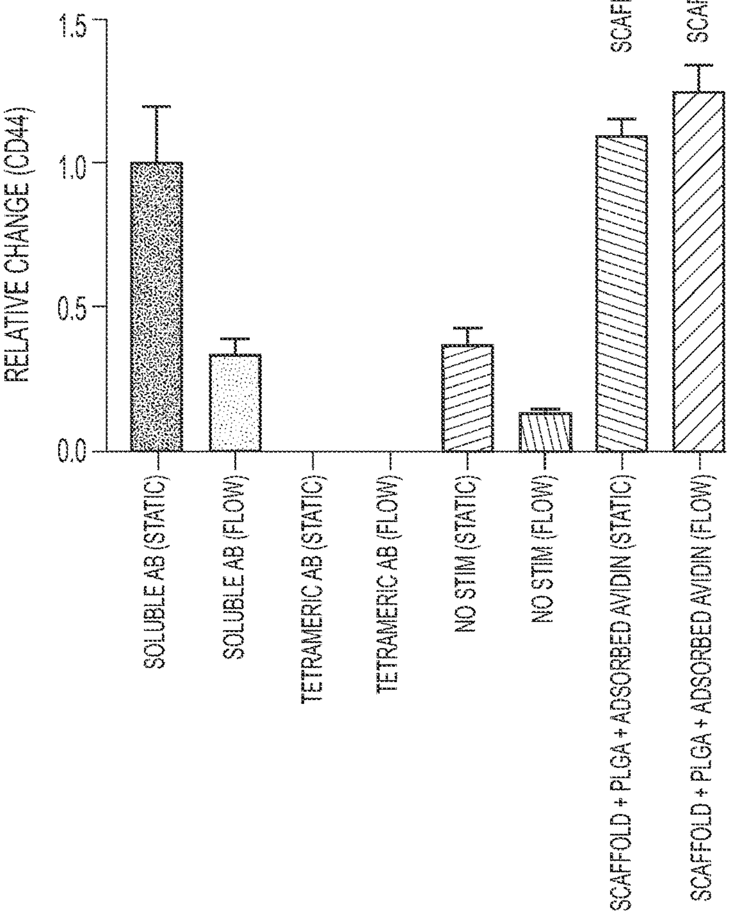
Figure 17C:
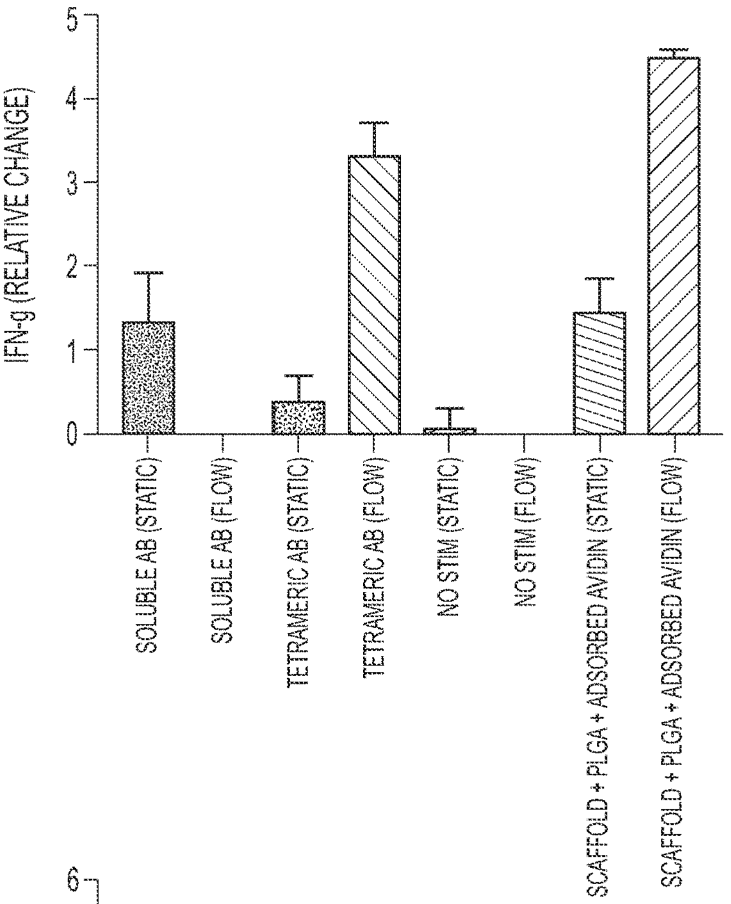
Figure 17D:
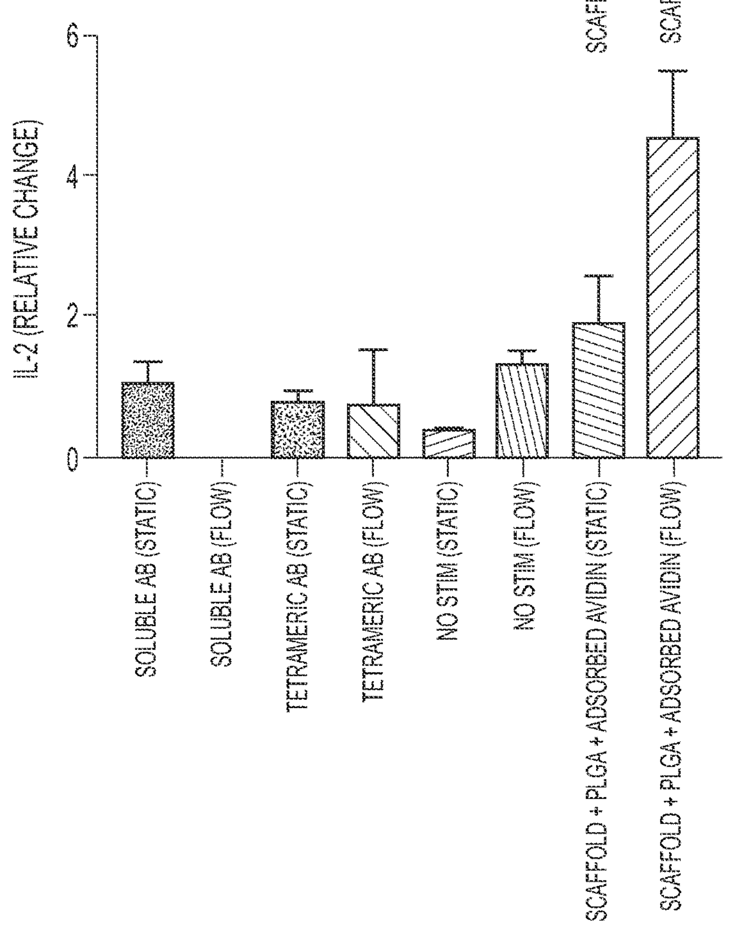
Figure 17E:
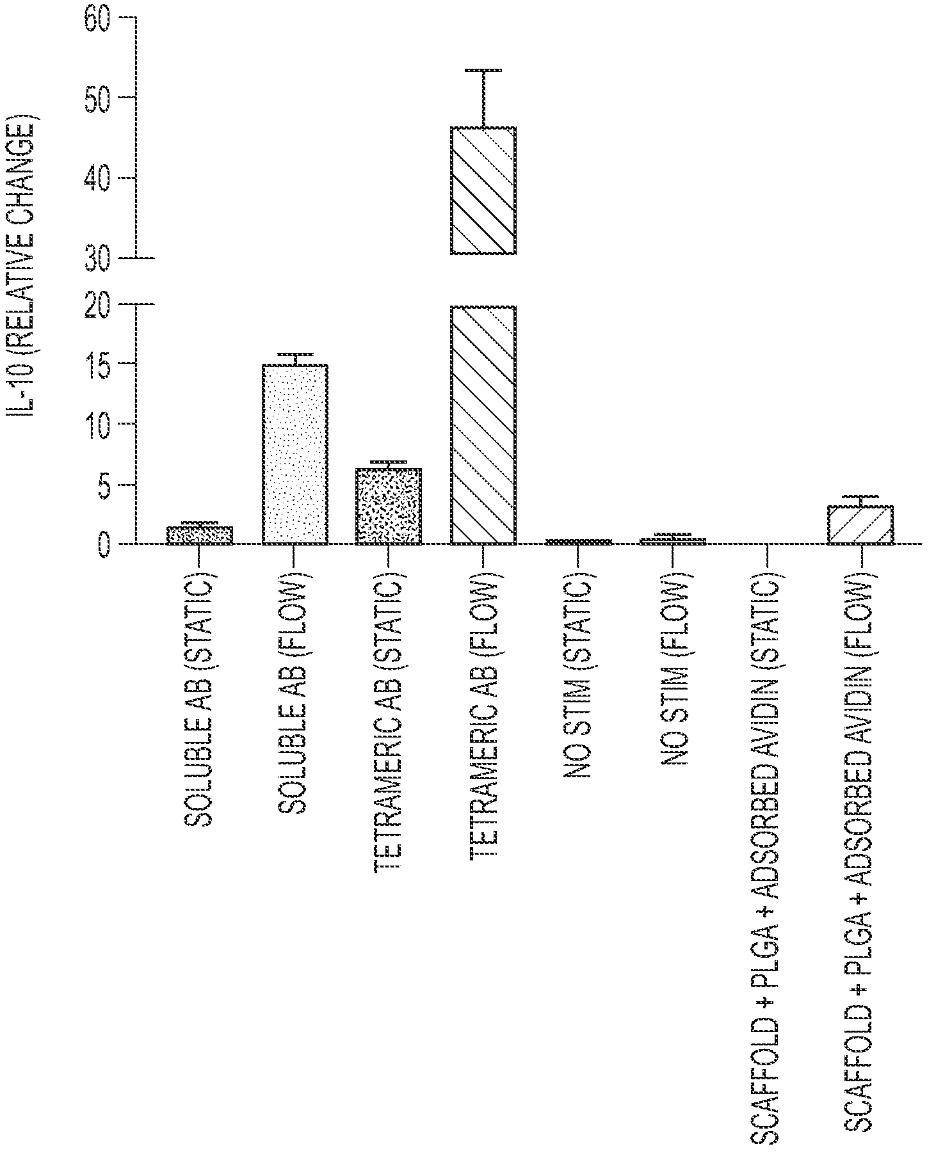

FIG. 16 The impact of flow on T cell activation and selectin expression. This is an illustration of an assay designed to test the impact of laminar flow on T cell activation. Cartridges were immobilized in a plastic tubing and subjected to laminar flow 5 ml/min.

FIGS. 17A-17E are bar graphs showing relative change in CD25 expression (17A), relative change in CD44 expression (17B), IFN-gamma secretion (relative change) (17C), IL-2 secretion (relative change) (17D), and IL-10 secretion (relative change) (17E) for splenocytes incubated with soluble Ab (under static or flow conditions), tetrameric Ab (under static or flow conditions), no stimulation control (under static or flow conditions), and scaffold+PLGA+adsorbed avidin (under static or flow conditions). Note that maximal activation, as evidenced by IFN and IL-2 secretion from expanded cells and least amount of IL-10 secreted is achieved under dynamic conditions of buffer flow through the device during T cell activation.

DETAILED DESCRIPTION OF THE INVENTION

I. Definitions

As used herein, "antigen" is a molecule which contains one or more epitopes that will stimulate a host's immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (Bergmann, et al., *Eur. J. Immunol.,* 23:2777-2781 (1993); Bergmann, et al., *J. Immunol.,* 157:3242-3249 (1996); Suhrbier, Immunol. and *Cell Biol.,* 75:402-408 (1997).

As used herein, "tumor-specific antigen" is an antigen that is unique to tumor cells and does not occur in or on other cells in the body.

As used herein, "tumor-associated antigen" is an antigen that is not unique to a tumor cell and is also expressed in or on a normal cell under conditions that fail to induce an immune response to the antigen.

As used herein, the term "isolated" describes a compound of interest (e.g., either a polynucleotide or a polypeptide) that is in an environment different from that in which the compound naturally occurs, e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation).

As used herein, a "variant" polypeptide contains at least one amino acid sequence alteration (addition, deletion, substitution, preferably conservative i.e., not substantially changing the function except in magnitude) as compared to the amino acid sequence of the corresponding wild-type polypeptide.

As used herein, an "amino acid sequence alteration" can be, for example, a substitution, a deletion, or an insertion of one or more amino acids.

As used herein, a "fragment" of a polypeptide refers to any subset of the polypeptide that is a shorter polypeptide of the full length protein. Generally, fragments will be five or more amino acids in length.

As used herein, "conservative" amino acid substitutions are substitutions wherein the substituted amino acid has similar structural or chemical properties.

As used herein, "non-conservative" amino acid substitutions are those in which the charge, hydrophobicity, or bulk of the substituted amino acid is significantly altered.

As used herein, "isolated nucleic acid" refers to a nucleic acid that is separated from other nucleic acid molecules that are present in a mammalian genome, including nucleic acids that normally flank one or both sides of the nucleic acid in a mammalian genome. As used herein with respect to nucleic acids, the term "isolated" includes any non-naturally-occurring nucleic acid sequence, since such non-naturally-occurring sequences are not found in nature and do not have immediately contiguous sequences in a naturally-occurring genome.

As used herein, the term "host cell" refers to prokaryotic and eukaryotic cells into which a recombinant expression vector can be introduced.

As used herein, "transformed" and "transfected" encompass the introduction of a nucleic acid (e.g. a vector) into a cell by a number of techniques known in the art.

As used herein, the phrase that a molecule "specifically binds" to a target refers to a binding reaction which is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity. Specific binding between two entities means an affinity of at least $10^6$, $10^7$, $10^8$, $10^9$, or $10^{10}$ $M^{-1}$. Affinities greater than $10^8$ $M^{-1}$ are preferred.

As used herein, the terms "antibody" or "immunoglobulin" include intact antibodies and binding fragments thereof. Typically, fragments compete with the intact antibody from which they were derived for specific binding to an antigen fragment including separate heavy chains, light chains Fab, Fab', F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.,* 79:315-321 (1990); Kostelny et al., *J. Immunol.,* 148, 1547-1553 (1992).

As used herein, the terms "epitope" or "antigenic determinant" refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids, in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke, et al., *J. Inf. Dis.,* 170:1110-19 (1994)), by antigen-dependent killing (cytotoxic T lymphocyte assay, Tigges, et al., *J. Immunol.,* 156:3901-3910) or by cytokine secretion.

As used herein, the terms "immunologic", "immunological" or "immune" response is the development of a humoral (antibody mediated) and/or a cellular (mediated by antigen-specific T cells or their secretion products) response directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, a "co-stimulatory polypeptide" is a polypeptide that, upon interaction with a cell-surface molecule on T cells, modulates the activity of the T cell. Thus, the response of the T cell can be an effector (e.g., CTL or antibody-producing B cell) response, a helper response providing help for one or more effector (e.g., CTL or antibody-producing B cell) responses, or a suppressive response. In some embodiments, co-stimulatory polypeptides enhance a T cell response, enhance proliferation of T cells, enhance production and/or secretion of cytokines by T cells, stimulate differentiation and effector function of T cells or promote survival of T cells relative to T cells not contacted with a costimulatory peptide.

As used herein the term "thermoplastic" or "thermoplastic polymeric material", refers to a material that softens and becomes fluid when heated and which hardens or freezes to a very glassy state when cooled sufficiently.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

II. Bioreactor Cartridges for Cell Modulation

Bioreactor cartridges (also referred to herein simply as "bioreactor" or "cartridge") for cell modulation, expansion, or a combination thereof are provided. The cartridges typically include a base support, a high surface area scaffold or substrate for presentation of cell ligands such as signaling molecules, and a polymer matrix or nanoparticulate layer for release of active agents such as cytokines. The structure of the cartridge can thus both physically engage the cells via ligand-receptor and/or provide secretory factors in a paracrine-like matter. The bioreactor can also be coupled to a means of providing a laminar flow (e.g., a pump and media reservoir), which creates laminar flow in the cartridge's microenvironment. The cartridge is particularly well suited for modulation of immune cells including T cells and antigen presenting cells, and in some embodiments, can be viewed as an artificial lymph node.

The components of the bioreactor, and exemplary applications thereof, are discussed in more detail below. Generally, a high surface area scaffold typically forms a high density, packed bed on a solid base support. Carbon nanotube scaffolds are a preferred high surface substrate. The substrate can be immobilized on the solid support in a polymer to add greater surface area and texture to the support. The substrate can be functionalized with end groups, such as carboxylic acids, amines, or other functional chemical groups allowing the attachment of ligands that can capture and/or provide signals to the cells.

Active agents such as a growth factor is typically impregnated in a biodegradable or non-biodegradable polymer such that it is released in a paracrine-like fashion in the vicinity of cells captured by the cartridge (also referred to as "paracrine delivery"). For example, a preferred growth factor for T cell activation and expansion is Interleukin-2 (IL-2). Paracrine delivery can increase expansion rates and achieve a more functionally robust cell product. Thus, the release of the factor is typically localized and in an effective amount to enhance the magnitude and kinetics of cell proliferation and/or a desired cellular phenotypic state (e.g., activation, suppression, etc.). Modulation and/or expansion (e.g., proliferation) of cells may be greater when presented to the cells via paracrine delivery than when the same growth factor is exogenously supplemented (e.g., added to the incubation media).

Following assembly of the bioreactor, the support can rolled or packed. In some embodiments, the rolled or packed reactor is placed in a housing chamber. Packing the support can further enhance the surface area, and facilitate cell-cell interactions/contact.

Media can be contacted with the bioreactor to create a shear rate that induces a physiological-like cell expansion. Flow rate through bioreactor may be between about about 0.1 ml/min and about 100 ml/min, preferably between about 0.1 ml/min and about 50 ml/min, such as between about 0.1 ml/min and about 5 ml/min, most preferably about 1.5 ml/min. Flow rates from 1 ml/min to 50 ml/min are important for various cell applications. In some embodiments, the flow rate is between 1 ml/min and 50 ml/min Flow can be intermittent/pulsed or continuous. Flow can be recycled through the reactor to conserve media and released growth factors.

The reactors can be stacked or serially arranged to produce a multiplicity of cell products with different specifies.

Each component of the bioreactor cartridge, systems including the cartridge, and methods of preparation and use thereof are provided in more detail below.

A. Base Support

The base support provides core support for the other components of the device. Typically, it can adsorb polymer solution impregnated with active agents. The base support is generally a high strength, high wicking porous substrate. It is typically strong enough to provide support for the T cell ligands discussed in more detail below, but also flexible or pliable enough to be manipulated into different shapes or orientations. For example, in some embodiments, the base support is a sheet that can be rolled.

In some embodiments, the base support is formed from a polymeric material or contains a polymeric material thereon. The polymeric material can be a thermoplastic, preferably a semicrystalline thermoplastic, such as a polypropylene or a poly(ethylene). The base support may be formed from or contain thereon any suitable thermoplastic polymeric material. Suitable thermoplastic polymeric materials include, but are not limited to, polyolefins, poly(isoprenes), poly(urethanes), poly(butadienes), fluorinated polymers, chlorinated polymers, polyamides, polyimides, polyethers, poly(ether sulfones), poly(sulfones), poly(vinyl acetates), copolymers of vinyl acetate, poly(phosphazenes), poly(vinyl esters), poly(vinyl ethers), poly(vinyl alcohols), poly(carbonates), or a combination thereof.

Suitable exemplary polyolefins include, but are not limited to, poly(ethylene), poly(propylene), poly(l-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene). Suitable exemplary fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene). Suitable polyamides include, but are not limited to, poly(imino(1-oxohexamethylene)), poly(iminoadipoyliminohexamethylene), poly(iminoadipoyliminodecamethylene), and polycaprolactam. Suitable poly(ether sulfones) include, but are not limited to, poly(diphenylether sulfone) and poly(diphenylsulfone-co-diphenylene oxide sulfone). Suitable copolymers of vinyl acetate include, but are not limited to, poly(ethylene-co-vinyl acetate) and such copolymers in which at least some of the acetate groups have been hydrolyzed to afford various poly(vinyl alcohols The base support formed from or containing thereon the aforementioned thermoplastic polymeric material(s) can be porous, such as macroporous or microporous. Methods of preparing substrates using thermoplastic polymeric material(s) which have selected porosities are known in the art. Selection of a particular thermoplastic material is within the knowledge level of a person of ordinary skill and will depend on the specific properties and characteristics desired, such as degree of porosity of the base support. The average pore diameter can be, for example, between about 50 μm and about 1,000 μm, or between about 50 μm and about 500 μm, or between about 50 μm and about 250 μm, or between about 50 μm and about 100 μm. The porosity over the surface of the base support can be uniform or substantially uniform (i.e., having substantially the same porosity and average pore diameter throughout its dimensions and thickness) or non-uniform or gradient porosity (i.e., having a first average diameter or first porosity at one major surface of the support and one or more second average pore diameters or second porosities at one or more opposing major surfaces, such that the average pore diameter or the porosity varies throughout the thickness of the base support).

In some embodiments, the average pore diameter is between about 100 μm and about 1000 μm. Smaller average pore diameters, for example 500 μm or less, e.g., between about 100 μm and 500 μm, are preferred for inducing activation of immune cells, while a larger average pore diameter, for example greater than 500 μm, e.g., 500 μm and 1000 μm may be favored for inducing a suppressive profile.

The average pore diameters can be of the same or similar sizes (i.e., homogenous or uniform), or can be of various different sizes within a range (i.e., homogenous or diversified). Pore sizes in the range of 100 μm to 5 mm Spherical pores are preferable, but pores may not necessarily be limited to spherical or any specific geometry or separations. Contiguous pores with boundaries in the thickness range of 1 μm are preferred but, tortuous pores with no defined boundaries or shape are acceptable. It is preferred that the material is an elastic substrate. Aligned or random pores or geometries are a possibility (we tested random alignment). Fiber diameters (composition of the scaffold boundaries) can range from 100 nm to 5000 nm. The elastic modulus (stiffness of the scaffold) is ideally between 0.05 to 0.2 GPa. However, acceptable ranges are from 0.005 to 2 GPa. The stiffness or elasticity depends on the polymer fiber density and hence a density of n between 1-100 fibers per square micron is acceptable, preferably 10 per square micron.

High wicking refers to absorption of fluid (organic or water-soluble) containing a cytokine to be adsorbed. High wicking range is between 5 to 10% of weight liquid absorbed per weight of polymer. Range is 0.1 to 15% and preferable 5-8% by weight.

Any of the devices herein can be formed of two or more sheets of base support. The character of the two or more sheets of base support in any device can be the same or different. Thus, a device can include two or more sheets of base support formed of the same or different materials, having the same or different scaffolds, the same or different signaling molecules and/or cell ligands, the same or different polymer layers, the same or different active agents, etc. By non-limiting illustration only, sheet 1 can contain anti-CD3 for polyclonal expansion, while sheet 2 may have MHC Class I with a cancer antigen (e.g., melanoma, etc.).

In some embodiments, a single sheet or multiple sheets of base support is rolled tightly. In other embodiments, a single sheet or multiple sheets of base support is rolled loosely or variably (e.g., varying the gap width between successive turns). In some embodiments, a spacer (e.g., blank sheet) can be used to vary the gap size between two or more layers.

The gap width(s) within a roll of a single sheet, and/or between two sheets can be from 1 μm to 500 μm. In some embodiments, the gap width varies, and is thus different, within rolls of single sheet, and/or between two or more sheets. In some embodiments, the gap width is consistent throughout a single rolled sheet, and/or between two or more sheets.

Although collectively referred to herein as rolled or rolling, it will be appreciated that different geometric shapes can be formed by different rolling or folding techniques. For example, conventional rolling by turning the sheet over and over on a single axis can be used to form a cylindrical shape, squeezing or balling can be used to form spherical shape, flat folding can be used to form a rectangular shape, etc.

The rolled sheet or sheets can be housed in a support device, for example, a gas permeable cylinder.

B. Scaffolds and Ligands

Attached to or otherwise adhered to base support are materials suitable for inducing or enhancing cell adhesion, signaling or a combination thereof. The materials typically include a scaffold (also referred to as substrate) upon which one or more ligands, co-receptors, or other signaling molecules are presented to cells, 1. Scaffolds and Substrates Suitable substrates and scaffolds include, but are not limited to, carbon, graphene, metallic nano and micro particles, pore glass systems or any other high surface area porous support typically used in the solid phase catalytic chemical reaction industry. Graphene, porous polymeric substrates with randomly aligned or aligned pores can be used. Preferable are high surface area substrates in the range of 250 micron square per gram of material to 2000.

In preferred embodiments, the substrate or scaffold is formed by carbon nanotubes (CNTs), or bundles thereof. CNT compositions and methods of use thereof for forming artificial antigen presenting cells are discussed in U.S. Pat. Nos. 9,737,593 and 8,658,178.

a. Carbon Nanotubes

Compositions for ligand presentation include carbon nanotubes (CNTs) as high surface area scaffolds for the attachment of ligands, co-receptors, and/or antigens. A carbon nanotube is a crystalline carbon with a structure in which a thin layer of graphite crystal is rolled-up into the shape of a cylinder. CNTs are formed of carbons atoms in the form of a graphene structure, which is a flat or curved layer formed by arranging six-membered rings of carbon atoms in a honeycomb. A carbon nanotube is a cylindrical structure in which such a layer is rolled-up in one direction. In general, those with a diameter of several nanometers to several ten of nanometers and a length of several ten times to not less than several thousand times longer than its diameter are called "carbon nanotubes".

CNTs that form the scaffold may be either single-walled CNTs (SWNTs) or multi-walled CNTs (MWNTs). In a preferred embodiment, the compositions contain SWNTs. SWNTs are formed by a single graphene layer rolled-up in the shape of a cylinder. MWNTs are formed by two or more graphene layers rolled-up in the shape of a cylinder. Single-walled carbon nanotubes may assume three types of shapes, termed "armchair", "zigzag", and "chiral", depending on how the six-membered rings are arranged.

SWNTs have applications ranging from electronics (Ouyang, et al., *Acc. of Chem. Res.,* 35:1018-25 (2002)), drug delivery (Feazell, et al., *J. Am. Chem. Soc.,* 129(27):8438-9 (2007); Kam, et al., *J. Am. Chem. Soc.,* 126(22):6850-1 (2004)), imaging (Sitharaman, et al., *Chem. Commun.,* (31): 3915-7 (2005)) and biosensing (Wang and Iqbal, *Journal of the Minerals,* 57:27-29 (2005)).

b. Methods for Making CNTs

CNTs may be fabricated using any suitable method. CNTs are normally produced by various methods, such as arc-discharge methods, laser evaporation methods, thermal chemical vapor deposition (CVD) methods, and flowing vapor deposition methods. The arc-discharge method is a method of growing CNTs by means of arc discharge using carbon electrodes. The arc-discharge method is capable of producing an enormous amount of CNTs. The laser evaporation method typically forms CNTs by evaporating part of a graphite electrode by means of a laser. The thermal CVD method grows carbon nanotubes at a high temperature by thermally decomposing hydrocarbon, which is a carbon source, on a substrate with a metal catalyst thereon. The flowing vapor deposition method generates carbon nanotubes by making an organic transition metal compound and a hydrocarbon compound, which is a carbon source, both flowing with a carrier gas, react with each other at a high temperature.

c. Methods for Attaching Proteins to CNTs

The CNT compositions typically contain attached proteins. Proteins may be attached to CNTs covalently through reaction with the functionalized CNT surface or non-covalently by non-specific adsorption (Kam, et al., *J. Am. Chem. Soc.,* 126(22):6850-1 (2004); Karajanagi, et al., *Langmuir,* 20:11594-9 (2004)).

CNTs have a high capacity for protein adsorption due to their high surface area. The surface area of CNTs available for protein adsorption may also be adjusted by altering the surface chemistry of the CNT. In this way, accessible surfaces that are a priori not available for protein adsorption may be made accessible through chemical treatment. In one embodiment, CNTs are subjected to treatment with acid prior to protein adsorption. Studies have demonstrated that acid treatment of SWNTs induces defects on the surface of the nanotubes (Hu, et al., *Jour. Phys. Chem. B,* 107:13838-42 (2003)), as well as promote de-bundling (Liang, et al., *Nano Lett.,* 4:1257-60 (2004)), which can be correlated with an increase in surface area (Hemraj-Benny, et al., *Jour. Coll. Interf. Sci.,* 317(2):375-82 (2008)). In one embodiment, CNTs are treated with nitric acid prior to protein adsorption, which introduces carboxylic acid groups at the open ends leading to sites of defects and hence increasing the capacity for protein adsorption (Hu, et al., *Jour. Phys. Chem. B,* 107:13838-42 (2003)). In one embodiment, the CNTs are reduced following acid treatment. For example, following nitric acid treatment, CNTs may be treated with lithium borohydride to preferentially reduce the oxygenated groups created by the acid treatment, favoring the dispersion of the CNTs in solution (U.S. Published Application No. 2004/0232073) and further increasing the surface area available for protein adsorption. The examples below demonstrate that treatment of CNTs with 3M $HNO_3$ significantly increases surface area of SWNTs, which is further increased by subsequent treatment with $LiBH_4$.

In addition to non-specific adsorption, proteins can also be attached to CNTs through covalent interactions through various functional groups. Functionality refers to conjugation of a molecule to the surface of the CNT via a functional chemical group (carboxylic acids, aldehydes, amines, sulfhydryls and hydroxyls) present on the CNT and present on the molecule to be attached. Biochemical functionalization of CNTs using various proteins for potential applications in biological systems are described by Kam, et al., *J. Am. Chem. Soc.,* 126(22):6850-1 (2004); Bianco, et al., *Curr. Opin. Chem. Biol.,* 9(6):674-9 (2005); Pantarotto, et al., *J. Am. Chem. Soc.,* 125(20):6160-4 (2003); Williams, et al., *Nature,* 420(6917):761 (2002); Pamtarotto, et al., *Chem. Commun.,* 1:16-7 (2004).

2. Ligands

The scaffold is typically utilized as a substrate for the presentation of one or more ligands to cells. The ligand or ligands are selected based on the target cell type and thus application specific. Exemplary ligands are provided below.

a. T Cell Recognition Signals

The scaffold can include one or more T cell recognition signals.

i. Antigen-Specific T Cell Activators

The scaffold can include antigen-specific T cell activators. Antigen molecules are recognized by the immune system after internal processing by natural APCs (Lanzavecchia, *Curr. Opin. Immunol.,* 8:348-54 (1996)). In order to present an antigen, the antigen is broken down into small peptidic fragments by enzymes contained in vesicles in the cytoplasm of the APCs. The enzymes are part of a complex of proteolytic enzymes called a proteosome. Most cells have several different types of proteosomes with differing combinations of specificities, which they use to recycle their intracellular proteins. The peptides produced by the proteosomes are generated in the cytosol and transported into the Golgi, where they are linked to cellular major histocompatibility complex (MHC) molecules. These are referred to as human leukocyte antigens, or "HLAs", in human. MHC and HLA are used interchangeably herein unless specified otherwise.

HLA and MHC Molecules

In some embodiments, the scaffolds described herein include antigen-presenting molecules having determinants which match that of a selected subject or which match any known antigen-presenting molecule determinants. The antigen-presenting molecules may be MHC/HLA class I or class II molecules.

There are two types of HLA molecules used for antigen presentation, class I and class II molecules. HLA class I molecules are expressed on the surface of all cells and HLA class II are expressed on the surface of a specialized class of cells called professional APCs. HLA class II molecules bind primarily to peptides derived from proteins made outside of an APC, but can present self (endogenous) antigens. In contrast, HLA class I molecules bind to peptides derived from proteins made inside a cell, including proteins expressed by an infectious agent (e.g., such as a virus) in the cell and by a tumor cell. When the HLA class I proteins reach the surface of the cell these molecules will thus display any one of many peptides derived from the cytosolic proteins of that cell, along with normal "self" peptides being synthesized by the cell. Peptides presented in this way are recognized by T-cell receptors which engage T-lymphocytes in an immune response against the antigens to induce antigen-specific cellular immunity.

Class I transplantation antigens of the major histocompatibility complex (MHC) or HLA are cell surface glycoproteins which present antigens to cytotoxic T-cells. They are heterodimeric and composed of a polymorphic, MHC-encoded, approximately 45 kD heavy chain, which is non-covalently associated with an approximately 12 kD β-2 microglobulin (β-2 m) light chain.

The extracellular portion of the MHC Class I heavy chain is divided into three domains, α-1, α-2, and α-3, each approximately 90 amino acids long and encoded on separate exons. The α-3 domain and β-2 m are relatively conserved and show amino-acid sequence homology to immunoglobulin constant domains. The polymorphic α-1 and α-2 domains show no significant sequence homology to immunoglobulin constant or variable region, but do have weak sequence homology to each other. The membrane-distal polymorphic α-1 (approximately 90 amino acids) and α-2 (approximately 92 amino acids) domains each include four anti-parallel, β-pleated sheets bordered by one α-helical regions, (the first from the α-1 and the second from the α-2 domain). The α-2 domain is attached to the less-polymorphic, membrane-proximal α-3 (approximately 92 amino acids) domain which is followed by a conserved transmembrane (25 amino acids) and an intra-cytoplasmic (approximately 30 amino acids) segment. The rat, mouse, and human Class I MHC molecules are believed to have similar structural characteristics based upon known nucleotide sequences of the various MHC Class I molecules.

The classical class I gene family includes the highly polymorphic human class I molecules HLA-A, -B, and -C, and murine class I (i.e., H-2) molecules D, K, and L. A series of structural relatives (non-classical class I molecules) has been found in humans (e.g., HLA-E, -F, -G, -H, -I, and -J; and CD1) and mice (Q, T, M, and CD1) (Shawar, et al., *Annu. Rev. Immunol.,* 12:839-880 (1994)). These molecules have the typical structure of an antigen-presenting molecule, where a polymorphic heavy chain is noncovalently associated with the conserved β2-M subunit.

In the case of human class I determinants, the determinant can be a polypeptide encoded by any of the known HLA genetic loci, as well as polypeptides encoded by genetic loci not yet discovered so long as these can present antigen to a T cell in a manner effective to activate the T cell receptor. Examples of known HLA class I genetic loci include for HLA-A: A1, A2, A3, A11, A23, A24, A25, A26, A28, A29, A30, A31, A32 and Aw33; for HLA-B: B7, B13, B18, B27, B35, B37, B38, B39, Bw31, Bw42, B44, B45, B49, Bw50, B51, Bw52, Bw53, Bw54, Bw55, Bw57, Bw58, Bw60, Bw61, Bw62, Bw63, Bw64 and Bw65; for HLA-C: $Cw1^b$, Cw2, Cw3, Cw4, Cw5, Cw6, Cw7 and Cw8.

The amino acid sequences of mammalian MHC class II alpha and beta chain proteins, as well as nucleic acids encoding these proteins, are also well known in the art and available from numerous sources including GenBank. Exemplary sequences are provided in Auffray, et al., *Nature,* 308(5957):327-333 (1984) (human HLA DQc); Larhammar, et al., *Proc. Natl. Acad. Sci. U.S.A.,* 80(23):7313-7317 (1983) (human LILA DQβ); Das, et al., *Proc. Natl. Acad. Sci. U.S.A.,* 80 (12): 3543-3547 (1983) (human HLA DRα); Tonnelle, et al., *EMBO J.,* 4(11):2839-2847 (1985) (human HLA DRβ); Lawrence, et al., *Nucleic Acids Res.,* 13(20): 7515-7528 (1985) (human HLA DPα); and Kelly and Trowsdale, *Nucl. Acids Res.,* 13(5):1607-1621 (1985) (human HLA DPβ).

The MHC class I or class II polypeptide selected for use with the CNT aAPCs is typically encoded by genetic loci present in the subject to be treated.

Antigens

MHC/HLA class I or class II molecules are used to present antigens to T cells to activate and expand T cells specific to the antigen. Antigens can be peptides, polypeptides, proteins, polysaccharides, saccharides, lipids, nucleic acids, or combinations thereof. Because CTL epitopes usually include 8-10 amino acid long (Townsend, et al., *Annu. Rev. Immunol.,* 7:601-624 (1989); Monaco, Cell, 54:777-785 (1992); Yewdell, et al., *Adv. in Immunol.,* 52:1-123 (1992)), in some embodiments, antigens are short polypeptides. Antigenic polypeptides may be about 5 to 40 amino acids, preferably 6 to 25 amino acids, more preferably 8 to 10 amino acids, in length. Examples of antigens presented in various immune responses are described in more detail below and are generally known in the art (Engelhard, *Curr. Opin. Immun.,* 6:13-23 (1994)).

Suitable antigens are known in the art and are available from commercial government and scientific sources. Criteria for identifying and selecting effective antigenic peptides (e.g., minimal peptide sequences capable of eliciting an immune response) can be found in the art. For example, Apostolopoulos, et al. (*Curr. Opin. Mol. Ther.,* 2:29-36 (2000)), discusses the strategy for identifying minimal antigenic peptide sequences based on an understanding of the three-dimensional structure of an antigen-presenting molecule and its interaction with both an antigenic peptide and T-cell receptor. Shastri, (*Curr. Opin. Immunol.,* 8:271-7 (1996)), disclose how to distinguish rare peptides that serve to activate T cells from the thousands peptides normally bound to MHC molecules.

The antigen can be derived from any source including, but not limited to, a virus, bacterium, parasite, plant, protozoan, fungus, tissue or transformed cell such as a cancer or leukemic cell. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic polypeptide. The DNA may be in the form of vector DNA such as plasmid DNA.

Antigens may be provided as single antigens or may be provided in combination. Antigens may also be provided as complex mixtures of polypeptides or nucleic acids.

Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Bacterial antigens Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halo-*

*bacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.e. birch (*Betula*), alder (*Alnus*), hazel (*Corylus*), hornbeam (*Carpinus*) and olive (*Olea*), cedar (*Cryptomeriaand Juniperus*), Plane tree (*Platanus*), the order of Poales including i.e. grasses of the genera *Lolium, Phleum, Poa, Cynodon, Dactylis, Holcus, Phalaris, Secale*, and Sorghum, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

Self-Antigens or Autoantigens

The antigen may also be a self-antigen or an autoantigen. Antigens may be antigens of any autoimmune or inflammatory disease or disorder including, but not limited to, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia greata, allergic responses due to arthropod bite reactions, Crohn's disease, ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

Preferred autoantigens include, but are not limited to, at least a portion of a thyroid-stimulating hormone receptor, pancreatic P cell antigens, epidermal cadherin, acetyl choline receptor, platelet antigens, nucleic acids, nucleic acid protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in graft rejection include antigenic components of the graft to be transplanted into the graft recipient such as heart, lung, liver, pancreas, kidney, and neural graft components.

ii. Polyclonal T Cell Activators

In some embodiments, the scaffold includes one or more polyclonal T cell receptor activators that activate T cells in the absence of specific antigens. Suitable polyclonal T cell activators include the mitogenic lectins concanavalin-A (ConA), phytohemagglutinin (PHA) and pokeweed mitogen (PWM).

Other suitable polyclonal T cell activators include antibodies that crosslink the T cell receptor/CD3 complex.

Exemplary antibodies that crosslink the T cell receptor include the HIT3a, UCHT1 and OKT3 monoclonal antibodies.

b. Costimulatory and T Cell Adhesion Molecules

In addition to ligation of the T cell receptor, activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.,* 14:233-258 (1996); Chambers and Allison, *Curr. Opin. Immunol.,* 9:396-404 (1997); and Rathmell and Thompson, *Annu. Rev. Immunol.,* 17:781-828 (1999)).

The scaffold may contain one or more species of co-stimulatory molecule. Exemplary co-stimulatory molecules, also referred to as "co-stimulators", include, but are not limited to, CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. Other exemplary co-stimulatory molecules that can be used include antibodies that specifically bind with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, CD4, CD25 (IL2RA), and a ligand that specifically binds with CD83. Other suitable costimulatory molecules include, but are not limited to, costimulatory variants and fragments of the natural ligands described above.

Adhesion molecules may be included for the purpose of enhancing the binding association between the CNT aAPCs and T cells. Suitable adhesion molecules include, but are not limited to, LFA-1, CD49d/29(VLA-4), CD11a/18, CD54 (ICAM-1), and CD106(VCAM) and antibodies to their ligands. Other suitable adhesion molecules include antibodies to selectins L, E, and P.

3. Adaptor Elements

CLICK chemistry (azido/Alkyne chemistry) can be used to attach various elements such as antibody or antigen linkers and homobifunctional and heterobifunctional linkers of size ranges from 10 nm length to 200 nm for large spanning domains and hence flexibility in tethering to T cells. Both cleavable and non-cleavable linker chemistries can be used.

"Click Chemistry" is a term used to describe reactions that are high yielding, wide in scope, create only byproducts that can be removed without chromatography, are stereospecific, simple to perform, and can be conducted in easily removable or benign solvents. This concept was developed in parallel with the interest within the pharmaceutical, materials, and other industries in capabilities for generating large libraries of compounds for screening in discovery research. Several types of reaction fulfill these criteria, thermodynamically-favored reactions that lead specifically to one product, such as nucleophilic ring opening reactions of epoxides and aziridines, non-aldol type carbonyl reactions, such as formation of hydrazones and heterocycles, additions to carbon-carbon multiple bonds, such as oxidative formation of epoxides and Michael Additions, and cycloaddition reactions.

In some embodiments, the substrate or scaffold for presentation of T cell ligands (e.g., carbon nanotudes) and the T cell ligands are linked via an adaptor element. Adaptor elements are molecular entities that associate with a substrate or support and facilitate the modular assembly and/or disassembly of functional elements including, but not limited to, T cell ligands, thereto. In some embodiments, the adaptor elements is, or otherwise includes, an affinity tag. For example, in some embodiments, the substrate for presentation of T cell ligands and the T cell ligands are each functionalized with a part of an affinity tag system. For example, in some embodiments, the substrate or scaffold is functionalized with avidin or variant thereof such as neutravidin, and the ligand(s) are functionalized with an avidin-binding material such as biotin.

The affinity tags can be any molecular species that form specific, noncovalent, physiochemical interactions with defined binding partners (also referred to as affinity tag pairs). Affinity tag binding partners which form highly specific, noncovalent, physiochemical interactions with one another can be referred to as "complementary". Suitable affinity tag pairs are well known in the art and include epitope/antibody, biotin/avidin, biotin/streptavidin, biotin/neutravidin, glutathione-S-transferase/glutathione, maltose binding protein/amylase and maltose binding protein/maltose. Examples of suitable epitopes which may be used for epitope/antibody binding pairs include, but are not limited to, HA, FLAG, c-Myc, glutatione-S-transferase, $His_6$, GFP, DIG, biotin and avidin. Antibodies (both monoclonal and polyclonal and antigen-binding fragments thereof) which bind to these epitopes are well known in the art. See, e.g., U.S. Pat. No. 9,737,593, which describes bundling neutravidin functionalized CNTs, and adding stochiometric amounts of biotinylated T cell antigens to be presented on the CNT surface. Compositions and methods for activating the surface of CNTs for functionalization with proteins and other molecules are also discussed above.

Affinity tags and other adaptor elements allow for highly flexible, modular assembly and disassembly of functional elements which are conjugated to affinity tags which form highly specific, noncovalent, physiochemical interactions with complementary affinity tags which are directly or indirectly conjugated to substrate or scaffold. Adaptor elements may be conjugated with a single species of affinity tag or with any combination of affinity tag species in any ratio. The ability to vary the number of species of affinity tags and their ratios conjugated to the substrate or scaffold allows for exquisite control over the number of functional elements which may be attached and their ratios.

Additionally or alternatively, the functional elements, such as T cell ligands, can coupled to the substrate or scaffold in the absence of affinity tags, such as through direct covalent interactions, or indirectly through an adaptor element. Adaptor elements can be covalently coupled to at least one species of functional element. Adaptor elements can be covalently coupled to a single species of functional element or with any combination of species of functional elements in any ratio. In some embodiments, the substrate or scaffold, the functional element(s) or a combination thereof are functionalized with one or more adaptor elements, and optionally an affinity tag. Thus, in some embodiments, an adaptor element links the substrate or scaffold to an affinity tag. In some embodiments, an adaptor element links the functional element, such a T cell ligand(s) to an affinity tag.

Suitable adaptors are known in the art. See, for example, U.S. Published Application No. 2015/0125384.

Adaptor elements may associate with the substrate or support through a variety of interactions including, but not limited to, hydrophobic interactions, electrostatic interactions and covalent coupling. Examples of adaptor elements which may associate with the substrate or support via hydrophobic interactions include, but are not limited to, fatty acids, hydrophobic or amphipathic peptides or proteins, and polymers. These classes of adaptor elements may also be used in any combination or ratio.

C. Polymer Layer

The base support can be coated or decorated with one or more polymers, preferably one or more biodegradable and/or non-biodegradable polymers. Whether biodegradable or non-biodegradable, the polymer is typically adsorbed or tethered to a porous, high tensile strength substrate, and the active agent(s) is release therefrom.

For example, biodegradable polymer can release the active agent as it degrades in the aqueous environment of a device in-use. Non-biodegradable polymers can also be advantageous because they can reduce the build up of polymer monomers up in the device relative to biodegradable polymers. In both cases, the aqueous environment of the device in-use, enhances diffusivity from the polymer.

In some embodiments, a polymer solution is applied to the base support and allowed to solidify. As the solvent in the polymer solution evaporates, the polymer is left in the pores of the porous support. After solvent evaporation, the polymer releases the active agent into aqueous environments. In some embodiments, the polymer layer is composed of particles such as microparticles, nanoparticles, or a combination thereof.

Typically, the polymer, or a matrix formed therefrom, includes one or more active agents associated with, encapsulated within, surrounded by, and/or dispersed therein. The one or more active agents can be released from the polymer or polymeric matrix into the surrounding aqueous microenvironment of the device (e.g, as the polymer degrades). Exemplary active agents, which are typically selected based on the desired application and cell type to modulated, are discussed in more detail below.

Paracrine release of active agents such as IL-2 may enhance T cell stimulation to a level comparable to exogenous IL-2 supplementation using a tens-, hundreds, or thousand-fold less soluble IL-2, and may show enhanced effector function and improved tumor fighting capability.

1. Polymers

A wide variety of polymers and methods for forming particles and matrices therefrom are known in the art of drug delivery. Polymers may be natural or unnatural (synthetic) polymers. Polymers can biodegradable and non-biodegradable.

Polymers may be homopolymers or copolymers that include two or more monomers. In terms of sequence, copolymers may be random, block, or include a combination of random and block sequences. Typically, polymers are organic polymers.

In some embodiments, non-biodegradable polymers can be used, especially hydrophobic polymers. Examples of preferred non-biodegradable polymers include ethylene vinyl acetate, poly(meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

Examples of polymers also include polyalkylenes (e.g., polyethylenes), polycarbonates (e.g., poly(1,3-dioxan-2one)), polyanhydrides (e.g., poly(sebacic anhydride)), polyhydroxyacids (e.g., poly(.beta.-hydroxyalkanoate)), polyfumarates, polycaprolactones, polyamides (e.g., polycaprolactam), polyacetals, polyethers, polyesters (e.g., polylactide, polyglycolide), poly(orthoesters), polyvinyl alcohols, polyurethanes, polyphosphazenes, polyacrylates, polymethacrylates, polycyanoacrylates, polyureas, polystyrenes, polyamines, poly(arylates), polycarbonates, poly(propylene fumarates), polyhydroxyalkanoates, polyketals, polyesteramides, poly(dioxanones), polyhydroxybutyrates, polyhydroxyvalyrates, polyorthocarbonates, poly(vinyl pyrrolidone), polyalkylene oxalates, polyalkylene succinates, poly(malic acid), poly(methyl vinyl ether), and poly(maleic anhydride). In some embodiments, polymers include polymers which have been approved for use in humans by the United States Food and Drug Administration (U.S.F.D.A.) under 21 C.F.R. § 177.2600, including but not limited to polyesters (e.g., polylactic acid, polyglycolic acid, poly (lactic-co-glycolic acid)), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may include anionic groups (e.g., phosphate group, sulphate group, carboxylate group); cationic groups (e.g., quaternary amine group); or polar groups (e.g., hydroxyl group, thiol group, amine group).

In some embodiments, polymers may be modified with one or more moieties and/or functional groups. Any moiety or functional group can be used. In some embodiments, polymers may be modified with polyethylene glycol (PEG), with a carbohydrate, and/or with acyclic polyacetals derived from polysaccharides (Papisov, 2001, ACS Symposium Series, 786:301). In some embodiments, polymers may be modified with PEG.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers including lactic acid and glycolic acid units, such as poly(lactic acid-co-glycolic acid) and poly (lactide-co-glycolide), collectively referred to herein as "PLGA"; and homopolymers including glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; lactide-PEG copolymers (e.g., PLA-PEG copolymers); glycolide-PEG copolymers (e.g., PGA-PEG copolymers); copolymers of lactide and glycolide (e.g., PLGA); copolymers of lactide, glycolide, and PEG (e.g., PLGA-PEG copolymers); and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly (ethylene imine)-PEG copolymers, poly(L-lactide-co-L-lysine), poly(serine ester), poly(4-hydroxy-L-proline ester), poly[.alpha.-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used is characterized by a lactic acid:glycolic acid ratio of approximately 85:15, approximately 75:25, approximately 60:40, approximately 65:35, approximately 50:50, approximately 40:60, approximately 25:75, or approximately 15:85. These may be copolymers or blends.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations including one or more of the foregoing polymers. The acrylic polymer may include fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof) Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules,* 32:3658; Barrera et al., 1993, *J. Am. Chem. Soc.,* 115:11010; Kwon et al., 1989, *Macromolecules,* 22:3250; Lim et al., 1999, *J. Am. Chem. Soc.,* 121:5633; and Zhou et al., 1990, *Macromolecules,* 23:3399). Examples of these polyesters include poly(L-lactide-co-L-lysine) (Barrera et al., 1993, *J. Am. Chem. Soc.,* 115:11010), poly(serine ester) (Zhou et al., 1990, *Macromolecules,* 23:3399), poly (4-hydroxy-L-proline ester) (Putnam et al., 1999, *Macromolecules,* 32:3658; and Lim et al., 1999, *J. Am. Chem. Soc.,* 121:5633). Poly(4-hydroxy-L-proline ester) was recently demonstrated to condense plasmid DNA through electrostatic interactions, and to mediate gene transfer (Putnam et al., 1999, *Macromolecules,* 32:3658; and Lim et al., 1999, *J. Am. Chem. Soc.,* 121:5633). These new polymers are less toxic than poly(lysine) and PEI, and they degrade into non-toxic metabolites.

In some embodiments, polymers can be anionic polymers. In some embodiments, anionic polymers include carboxyl, sulfate, or groups. To give but a few examples, anionic polymers include, but are not limited to, dextran sulfate, heparan sulfate, alginic acid, polyvinylcarboxylic acid, and arabic acid carboxymethylcellulose. In some embodiments, anionic polymers are provided as a salt (e.g., sodium salt).

In some embodiments, a polymer may be a carbohydrate, properties of which are described in further detail below. In some embodiments, a carbohydrate may be a polysaccharide including simple sugars (or their derivatives) connected by glycosidic bonds, as known in the art. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, a polymer may be a protein or peptide, properties of which are described in further detail below. Exemplary proteins include, but are not limited to, albumin, collagen, gelatin, poly(amino acid) (e.g., polylysine), and antibodies.

In some embodiments, a polymer may be a polynucleotide. Exemplary polynucleotides include, but are not limited to, DNA, RNA, etc.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, *J. Am. Chem. Soc.,* 123:9480; Lim et al., 2001, *J. Am. Chem. Soc.,* 123:2460; Langer, 2000, *Acc. Chem. Res.,* 33:94; Langer, 1999, *J. Control. Release,* 62:7; and Uhrich et al., 1999, *Chem. Rev.,* 99:3181). More generally, a variety of methods for synthesizing suitable polymers are described in Concise Encyclopedia of Polymer Science and Polymeric Amines and Ammonium Salts, Ed. by Goethals, Pergamon Press, 1980; *Principles of Polymerization* by Odian, John Wiley & Sons, Fourth Edition, 2004; Contemporary Polymer Chemistry by Allcock et al., Prentice-Hall, 1981; Deming et al., 1997, *Nature,* 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used without undergoing a cross-linking step.

It is further to be understood that controlled release polymer systems may be a homopolymer, block copolymer, diblock triblock, multibock copolymer, linear polymer, dendritic polymer, branched polymer, graft copolymer, blend, mixture, and/or adduct of any of the foregoing and other polymers.

In some embodiments, the polymeric matrix layer is formed of particles, such as microparticles or nanoparticles, or a combination thereof, and the active agents are encapsulated therein.

2. Active Agents

One or more therapeutic, diagnostic, and/or prophylactic agents can be associated with or dispersed within a polymeric matrix. Association can be covalent or non-covalent. In some embodiments, covalent association is mediated by a linker (e.g., an aliphatic or heteroaliphatic linker). In some embodiments, a therapeutic, diagnostic, and/or prophylactic agent is non-covalently associated with a polymeric matrix. In some embodiments, a therapeutic, diagnostic, and/or prophylactic agent is associated with the surface of, encapsulated within, surrounded by, and/or dispersed throughout a polymeric matrix.

The active agent can be a polypeptide. Such proteins may be provided as the full-length polypeptide or an active fragment thereof. Any of the proteins can be human proteins, particularly when the subject to be treated is a human.

Typically, for modulation of immune cells including T cells and antigen presenting cells, at least one immunomodulators is included in or associated with the polymer. In particular embodiments at least one immunostimulatory agent is associated with or dispersed within the polymeric matrix.

Immunomodulators include, but are not limited to, matrix metalloproteinases (MMP), cytokines, interleukins (e.g., IL-1, IL-1β, IL-2, IL-4, IL-5, IL-6, IL-7, IL-12, IL-21, IL-22, IL-23, IL-17 etc.), interferons (e.g., interferon-γ), macrophage colony stimulating factor, and tumor necrosis factor (e.g., TNF-α, TGF-beta); and co-stimulatory molecules, such as those of the B7 family.

Active agent also include nucleic acids (e.g., nucleic acids encoding gene editing constructs, inhibitory nucleic acids such miRNA, siRNA, etc., and nucleic acids encoding proteins).

Active agents also include antigens. For example, the bioreactor can be used to modulate dendritic cells and other antigen presenting cells. As discussed in more detail below, antigens (e.g., protein or peptide antigens) can be released from the polymeric layer where they internalized by the APC and processed for later presentation to T cells.

Active agents also include small molecules. In some embodiments, particularly those associated with induction of tolerance (when inducing dendritic cells or other Antigen Presenting Cells to assume a tolerogenic phenotype), the small molecule can be a tolerogenic drug.

Preferred agents include Rapamycin, Retinoic acid, TGFβ and IL-2 proteins. Other small molecule tolerogenic agents include *RAPA* analogues, Mycophenolic acid, or combinations thereof. Biologics include all anti-inflammatory cytokines with focus on TGFb and IL-10 for autoimmune applications.

3. Other Materials

In some embodiments, the particles or matrix includes one or more magnetic particles. The magnetic particles will in some cases be present on or encapsulated within the polymeric particles, or dispersed within or otherwise associated with the polymer sheet. The magnetic particles can be in the same or different polymeric particles as the active agent. In some embodiments, the magnetic particles are associated with the scaffold in addition to or alternative to the polymeric material. In some embodiments, the magnetic particles allow a composition with which they are associated to exhibit superparamagnetic properties (e.g., at room temperature). The magnetic particles can be used to separate the disclosed materials, particularly the scaffold, from the cells. "Magnetic material" as used herein refers to any material that induces a force or movement when introduced into a magnetic field. Suitable magnetic materials include, but are not limited to, ferromagnetica and superparamagnetic materials, such as iron containing compounds, martensitic stainless steels (e.g. 400 series), iron oxides($Fe_2O_3$, $Fe_3O_4$), neodymium iron boron, alnico (AlNiCo), and samarium cobalt ($SmCo_5$).

In some embodiments, the polymeric material may include an antigen or combination of antigens. Exemplary antigens are discussed in more detail below.

In some embodiments, the polymeric material includes one or more nucleic acids, for example a vector encoding a heterologous protein. Such embodiments can be used to facilitate the preparation of modified T cells (e.g., CAR-T cells, during T cell activation and expansion). Such methods are discussed in more detail below.

The polymer layer may release a cytokine. For example, high surface inorganic materials such as carbon nanotubes or graphene may be used to adsorb cytokine which is then released into the medium. Other materials include materials that impact the functionality of T cells such as antibodies, selectins and integrins, carbohydrates such as sialyl lewis X, and metabolic factors that may alter T cell metabolism and hence impact activation such as glucose, butyric acid, or other metabolic substrates.

III. Methods of Making Cartridges

Cartridges can be prepared using any means such that the materials retain their ability to modulate cells. In an exemplary method, a liquid polymer solution containing the one or more active agents is adsorbed onto or otherwise coats at least one surface of a base support. The polymer is allowed to cure to form a polymer layer that can release the one or more active agents as it degrades. Before the liquid polymer has fully cured, carbon nanotube bundles or another suitable substrate for presentation of functional elements such as cell ligands are added to the semi-dry polymer layer such that they when the layer dries the substrate for presentation of cell ligands is immobilized therein.

In some embodiments, the substrate or scaffold (e.g., carbon nanotubes) are decorated with polymeric particles (e.g., nanoparticles) having an active agent associate therewith or dispersed therein. The substrate or scaffold can then be adsorbed onto the base support. In some embodiments, the scaffold is passively adsorbed onto the base support.

The functional elements such as T cell ligands can be associated with their substrate or scaffold (e.g., carbon nanotubes) before, or after, the substrate or scaffold is immobilized in the polymer or adsorbed onto the support. In a non-limiting example, the scaffold is functionalized with one part of an affinity pair (e.g., neutravidin), the functionalized scaffold is immobilized in the semi-dry polymer layer otherwise adsorbed onto the support, and the scaffold is contacted with a second part of the affinity pair (e.g., biotin-functionalized elements such as T cell ligands) to form artificial antigen presenting cells immobilized on the support.

Substrate adsorbed with polymer releasing cytokine and, optionally, inorganic material for added surface area, may be rolled or stacked. Stacked rectangular or circular discs in alternating patterns with blank discs or rolled sheets are preferable. Alternatively, a gas formed polymer through porogen flow may be used to assemble the scaffold. Packing cylindrical or spherical or prismoid geometries with polymeric beads can also be used. Packed bed reactors with polymeric or randomly shaped beads are important embodiments.

As discussed in more detail below, cells can be modulated by incubating them in the presence of the cartridge. The incubating can occur in any environment suitable for culturing cells. In some embodiments, the cartridge is part of a larger system for modulating and expanding cells. For example, the cartridge can be packaged into a gas permeable housing. In some embodiments, the cartridge is loosely rolled (e.g., into a cylinder) or otherwise bundled to compact the cartridge for packaging into the housing.

Figure 1:
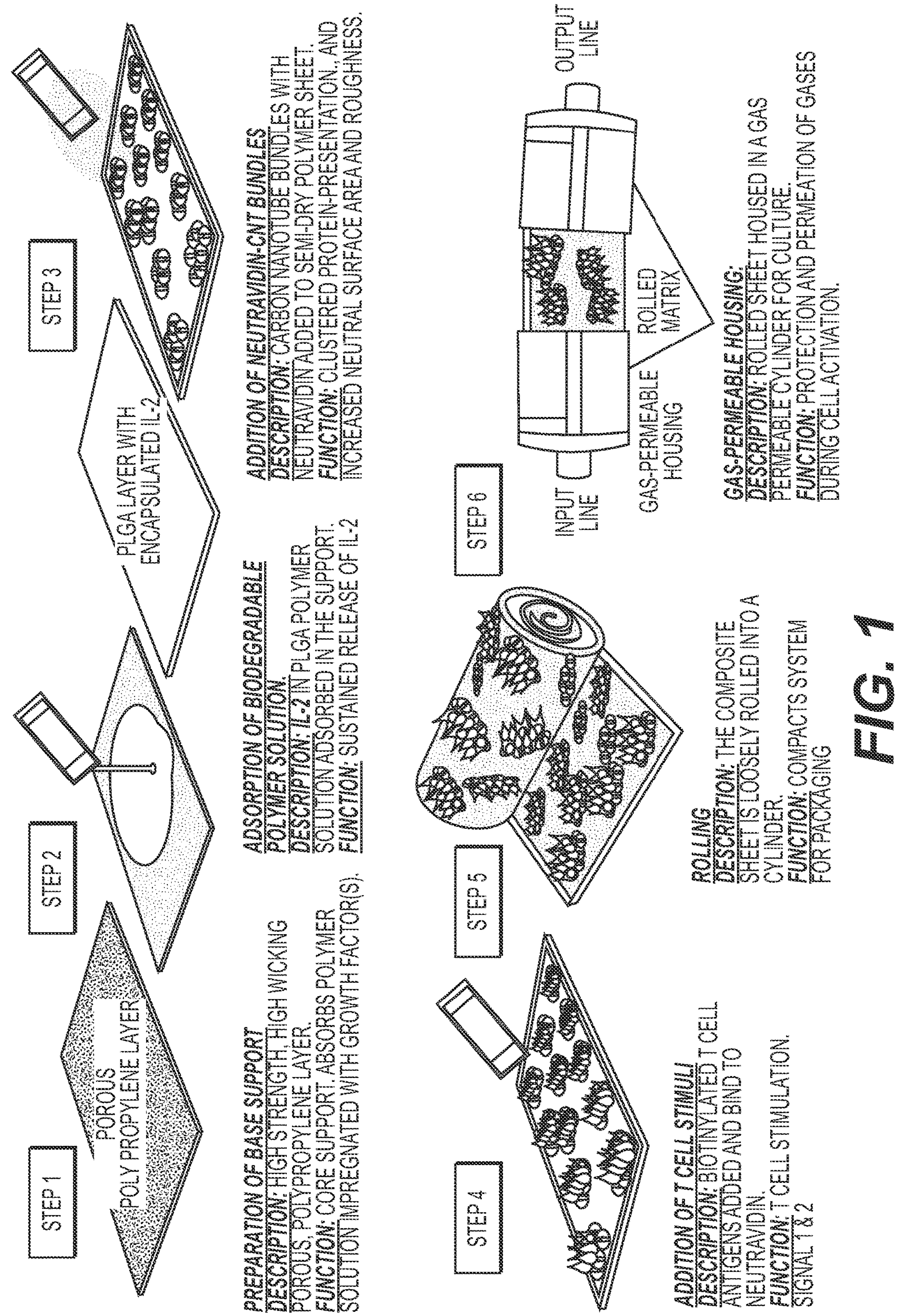
FIG. 1 is an illustration showing the materials, structure, and preparation of an exemplary bioreactor cartridge. A base support formed of a high strength, high wicking, porous, (non-biodegradable) polypropylene layer serves a core support and surface for the adsorption of a biodegradable or non-biodegradable polymer (e.g., PLGA), preferably non-biodegrable polymer impregnated with active agent such as growth factor (e.g., IL-2). Liquid (in solution or heated to above the melting point) polymer is poured onto a surface of the base support and allowed to coat the surface and form a polymer layer that can facilitate sustained release of active agent. Carbon nanotube bundles functionalized with a linker, in this case neutravidin, can be added to the semi-dry polymer sheet, and thus embedded in the layer formed therefrom. T cell stimuli such as biotinylated T cell antigens and co-stimulatory molecules can be added to the functionalized nanotubes to form artificial antigen presenting cells. The composite sheet can be rolled into a cylinder, which compacts the system for packing into a housing (e.g., a gas permeable housing) or other compartment. The housing can protect the cartridge and allow permeation of gases during T cell incubation, activation, and expansion.

An exemplary method of making a bioreactor cartridge is illustrated in FIG. 1.

Exemplary Protocol for Device Preparation

An exemplary, non-limiting device preparation protocol can include one or more of the following steps or a variation thereof.

Bundled CNTs can be obtained from a commercial vendor (e.g., Nanoshel) or synthesized (e.g., from cobalt-incorporated MCM-41 (Co-MCM-41) to generate bulk low-defect-density nanotubes). The nanotubes can be purified using a mild, treatment procedure that can include NaOH reflux, HCl wash, and oxidation by 4 mol % molecular oxygen. Material can be washed twice in sodium hydroxide (e.g, for 1 hour), followed by subsequent filtration using a PTFE filter. A second cleaning step can be carried out using hydrochloric acid (HCl) (e.g., at 60° C. overnight). To remove amorphous carbon particulates, material can be heated in 4 mol % oxygen stream in a quartz reactor (e.g., at 300° C.) followed by repeated HCl washing, filtration, and drying steps.

To facilitate protein attachment and further increase surface area, defects can be introduced by oxidation/reduction. Thus an exemplary preferred CNT is oxidized bundled (bCNTs-OH). Oxidized bundled CNTs can be produced by stirring 1 gram of material with 10 ml 3 M $HNO_3$ (e.g., at 70° C. for 1 hour). This step introduces —COOH groups that are later reduced with $LiBH_4$ to produce OH groups. Introduction of OH groups facilitates dispersion and increased surface area. This can be followed by filtration using a 5 μm pore size PTFE membrane and drying (e.g., at 45° C. for 24 hrs). The material can be reduced by the addition of $LiBH_4$ solution in THF and sonication (e.g., for 1.5 hours).

In an exemplary method of attaching proteins to CNTs, any remaining solvent from CNT manufacturing can be evaporated. Bundled CNTs can be dispersed in buffered saline. This is sonicated (for e.g., 10 minutes) to obtain uniform dispersion. An equal volume of 100 μg/ml of protein (e.g., neutravidin) is added. The mixture is allowed to mix in a rotary shaker (e.g., at 4° C. overnight). Bundled CNT-protein mixtures are then centrifuged in a microcentrifuge (e.g., at 15,000 rpm for e.g., 20 minutes) to wash away excess proteins. If stored, no washing steps are needed. Washing can take place just before attachment of biotinylated ligands.

Next the CNTs can be immobilized in polymer or otherwise adsorbed on the support base. In some embodiments, the base support is first soaked in a biodegradable polymer such as PLGA or a non-biodegradable polymer such as poly(ethylene-co-vinyl acetate). The polymer solution which is typically in hydrophobic organic solvent containing an active agent, for example a growth factor such as IL-2 or another active agent for cell modulation (e.g., T cell proliferation).

After polymer deposition and approximately 50 to 80% prior to full solvent evaporation, the graphene or CNT or other high surface area scaffold is added. This adds additional surface area and charge and provides a substrate for surface presentation (and clustering) of, e.g., signals 1 and 2.

Next the solvent is completely evaporated and the polymer and CNT are fully adsorbed to the base support. When the solvent evaporates the polymer is left in the porous substrate, and ready to release active agent when exposed to an aqueous environment.

Biotinylated ligands such as anti-CD3, anti-CD28 can be added before or after the CNTs are immobilized on the base. For example, signaling molecules can be incubated with CNTs (e.g., for 1 hour at equimolar concentration). In some embodiments, nanoparticles are adsorbed or otherwise functionalized on the CNTs and/or the base support. Particles can be absorbed on the CNTs or the base support. In an exemplary method recombinant proleukin human IL-2 (e.g., from Novartis) at 1.2 mg/mL in PBS is added dropwise to a vortexing solution of PLGA 50:50 (100 mg) with an inherent viscosity of 0.59 dL/g (Lactel Polymers). The mixture can be added dropwise to a vortexing solution of 5% poly-vinyl alcohol or PVA (Sigma-Aldrich) with MW average 30-70 kD and DSPE-PEG-Biotin (4.14 mg/0.828 mL) (Avanti Polar Lipid). The mixture can then be sonicated (e.g., 3 times for 10 seconds at 38% amplitude). The solution can be added dropwise to 100 mL of 0.2% PVA, and left stirring (e.g., for 3 hr) to evaporate the solvent. Particles can be collected by centrifugation (e.g., at 12,000 rpm for 15 min at 4° C.), then washed (e.g., 3 times) with deionized water. The particles can be lyophilized and stored at −20° C. Nanoparticles can be added to CNTs (e.g., for 30 min) An exemplary ratio is 100 ug of NP per 100 ug of CNT. The mixture can be diluted in cell culture media at a 5:1 dilution ratio.

The base support can be washed (e.g., one with 1×PBS) and rolled and packaged in a gas permeable housing. The housing can be fitted with IV lines for quick implementation into a system and use in clinical settings as discussed in more detail below.

IV. Methods of Modulating T Cells

A. Modulation Strategies

1. T Cell Activation

The cartridge is useful for ex vivo activation T cells, for use in, for example, adoptive immunotherapy applications. A number of important signals have been identified that lead to robust ex vivo activation and expansion of cells. The disclosed bioreactors are designed to provide these signals in a microenvironment that enhances cell modulation and expansion over traditional tissue culture. Although the ligands and paracrine factors can be changed based on the cell type of interest, the principles of the bioreactors can be illustrated with reference to T cell activation and expansion.

In immune stimulation applications, the materials for immune stimulation are typically present in amounts effective to cause activation of T cells, proliferation of T cells, or the combination thereof. Any suitable means of antigen presentation can be used. Artificial antigen presentation to T cells is known in the art and discussed in, for example, (Prakken, et al., *Nat. Med.,* 6(12):1406-10 (2000); Oelke, et al., *Nat. Med.,* 9(5):619-24 (2003); Kim, et al., *Nat. Biotechn.,* 22:403-10 (2004)). The development of artificial APCs (aAPCs) is an effort to generate a reproducible, "off-the shelf" means of stimulating and expanding T cells. Several types of aAPCs have been developed, including nonspecific bead-based systems that are currently used in many research laboratories to sustain the long-term expansion of $CD8^+$ T cells (Oelke, et al., *Nat. Med.,* 9(5):619-24 (2003); Kim, et al., *Nat. Biotechn.,* 22:403-10 (2004)).

Thus, in some embodiments, the substrate and ligand(s) is an artificial antigen presenting cell (aAPC).

Specific expansion of T cells outside the body is favored by efficient methods of displaying protein ligands that stimulate those cells. Ultimately, T cell stimulus intensity depends on the density of bound receptors in the contact area with a surface (Andersen, et al., *J. Biol. Chem.,* 276(52):49125-32 (2001); Gonzalez, et al., *Proc. Natl. Acad. Sci. U.S.A.,* 102(13):4824-9 (2005)). Regions with a high density of T cell antigen receptors have been termed activated clusters because they are important for T cell stimulation (Grakoui, et al., *Science,* 285(5425):221-7 (1999); Monks, et al., *Nature,* 395(6697):82-6 (1998)). The presence of such high-density clusters has also been shown to accelerate T cell activation (Gonzalez, et al., *Proc. Natl. Acad. Sci. U.S.A.,* 102(13):4824-9 (2005)). In the lymph node, the primary site for T cell stimulation, antigen presenting cells are thought to concentrate the presentation of T cell stimuli by trafficking in a dense architectural scaffolding in close proximity to T cells. Thus in preferred embodiments, ligands for T cell activation and expansion are presented on carbon nanotube scaffolds.

Scaffold compositions such as CNTs can function as artificial antigen presenting cells (aAPCs) by coupling immune stimulators to the scaffold. Proteins that are covalently or non-covalently attached to scaffolds are typically T cell ligands that bind to cell surface molecules on T cells. Typically, the ligands are polypeptides. Suitable T cell ligands include, but are not limited to, antigen-specific and polyclonal T cell receptor ligands, co-stimulatory molecules, and T cell targeting and adhesion molecules. Scaffolds aAPCs may be associated with a single species of functional T cell ligand or may be associated with any combination of disclosed T cell ligands in any ratio.

Exemplary ligands are discussed in more detail above.

Suitable T cell ligands may contain the entire protein that binds to the desired cell surface receptor, or may contain only a portion of the ligand. For example, it may be desirable to remove a portion of the ligand that has an undesirable biological activity, or it may be desirable to remove a portion of the ligand to enable attachment of the scaffolds. The only requirement when a portion of a ligand is present is that the portion of the ligand substantially retains the ligand's receptor binding activity. The terms "portion" and "fragment" are used herein interchangeably.

Suitable T cell ligands include variant ligands. As used herein, a "variant" polypeptide contains at least one amino acid sequence alteration as compared to the amino acid sequence of the corresponding wild-type polypeptide. An amino acid sequence alteration can be, for example, a substitution, a deletion, or an insertion of one or more amino acids.

A variant polypeptide can have any combination of amino acid substitutions, deletions or insertions. In one embodiment, variant polypeptides have an integer number of amino acid alterations such that their amino acid sequence shares at least 60, 70, 80, 85, 90, 95, 97, 98, 99, 99.5 or 100% identity with an amino acid sequence of a corresponding wild type amino acid sequence. In a preferred embodiment, variant polypeptides have an amino acid sequence sharing at least 60, 70, 80, 85, 90, 95, 97, 98, 99, 99.5 or 100% identity with the amino acid sequence of a corresponding wild type polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The well-known Smith Waterman algorithm may also be used to determine identity.

Exemplary parameters for amino acid sequence comparison include the following: 1) algorithm from Needleman and Wunsch (*J. Mol. Biol.,* 48:443-453 (1970)); 2) BLOSSUM62 comparison matrix from Hentikoff and Hentikoff (*Proc. Natl. Acad. Sci. U.S.A.,* 89:10915-10919 (1992)) 3) gap penalty=12; and 4) gap length penalty=4. A program useful with these parameters is publicly available as the "gap" program (Genetics Computer Group, Madison, Wis.). The aforementioned parameters are the default parameters for polypeptide comparisons (with no penalty for end gaps).

Alternatively, polypeptide sequence identity can be calculated using the following equation: % identity=(the number of identical residues)/(alignment length in amino acid residues)*100. For this calculation, alignment length includes internal gaps but does not include terminal gaps.

Amino acid substitutions in variant polypeptides may be "conservative" or "non-conservative". As used herein, "conservative" amino acid substitutions are substitutions wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain.

Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Variant polypeptides may be modified by chemical moieties that may be present in polypeptides in a normal cellular environment, for example, phosphorylation, methylation, amidation, sulfation, acylation, glycosylation, sumoylation and ubiquitylation. Variant polypeptides may also be modified with a label capable of providing a detectable signal, either directly or indirectly, including, but not limited to, radioisotopes and fluorescent compounds.

Variant polypeptides may also be modified by chemical moieties that are not normally added to polypeptides in a cellular environment. Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Polypeptides may also include one or more D-amino acids that are substituted for one or more L-amino acids.

Polypeptides to be attached to scaffolds such as CNTs may also be coupled to other polypeptides to form fusion proteins. Exemplary polypeptides have a first fusion partner including all or a part of a T cell ligand fused (i) directly to a second polypeptide or, (ii) optionally, fused to a linker peptide sequence that is fused to the second polypeptide.

An exemplary bioreactor strategy for activating T cells can include the following signals:

Signal 1: A T cell recognition signal (e.g., Polyclonal: anti-CD3 or Clonal: Peptide/Major Histocompatibility Complex). This signal selects for the phenotype or specificity of cells of interest.

Signal 2: A Co-stimulatory amplification signal (anti-CD28, anti-IBB, etc.). This signal amplifies the recognition signal and initiates the T cell activation program.

Signal 3: Paracrine delivery of a T cell growth factor (e.g., Interleukin-2). This signal is most effective at insuring robustness of T cell expansion when deployed similarly to the body's natural delivery of this factor in vivo: proximal, with high concentration, and sustained.

Signal 4: Laminar Flow Laminar flow enhances the quality of expanded T cells and expression of key markers important for cell potency against tumors.

Signal 5: High surface area of presentation of other signals, which is how T cells are expanded in the lymph nodes in vivo.

Signal 6: Electrostatics. T cell expansion is best performed under specific charge. The structure of the cartridge provides signals 1-3 and 5-6. When coupled to a means of providing a laminar flow (e.g., a pump and media reservoir), all six signals are present in the cartridge microenvironment. The cartridge can be viewed as an artificial lymph node used outside the body for cell expansion.

In preferred embodiments, antigen presentation includes regions of high density of T cell stimuli. In some embodiments, ligand density of, for example, 0.1 μg/square micron to 100 μg/square micron, or 0.5 μg/square micron to 10 μg/square micron, or 1 μg/square micron to 10 μg/square micron, or 2.5 μg/square micron to 100 μg/square micron or 5 μg/square micron to 50 μg/square micron or 5 μg/square micron to 10 μg/square micron. The ligand density may also be between about 0.1 μg per 10 square micron and about 100 μg per 10 square micron. A density in the range of about 1 μg per 10 square micron to about 30 μg per 10 square micron is preferred, and a density in the range of about 0.9 μg per 10 square micron to about 5 μg per 10 square micron, such as about 5 μg per 10 square micron, is most preferred.

Activation of T cells can increase their proliferation, cytokine production, differentiation, effector functions and/or survival. Methods for measuring these are well known to those in the art.

2. T Cell Tolerance

Adoptive immunotherapy may also be used to treat or prevent conditions associated with undesirable activation, over-activation or inappropriate or aberrant activation of an immune response, as occurs in conditions including autoimmune disorders and diseases, allergic reactions, graft rejection and graft-versus-host disease. Although most typically discussed herein with reference to modulating T cells to achieve an activated state against an antigen such as a cancer or foreign antigen, the compositions, materials, systems and methods for suppressing T cells, or activating or expanding regulatory T cells are also provided. For example, such compositions may include T cell ligands (T cell recognition signal and suppressive co-stimulatory molecules) that induce T cell suppression again self-antigens.

In some embodiments, the scaffolds and ligands mimic tolergoenic antigen presenting cells. Tolerogenic dendritic cells induce tolerance through several mechanisms. For example, tolerogenic APCs can present antigens to T cells via interaction of MHC class II-antigen complexes on the dendritic cell with T cell receptors on the T cell (Raker, et al., *Front Immunol.* 2015; 6: 569). This can induce T cell clonal deletion, T cell anergy or the proliferation of regulatory T cells (Tregs). Collectively, these mechanisms produce tolerance to specific antigens, which should help to prevent autoimmunity, but could therefore also be used as a therapy to induce tolerance to specific antigens implicated in autoimmune disease, or donor antigens in transplant patients.

Tolerogenic APCs may provide insufficient stimulatory signals for T cells and therefore drive naïve T cells to differentiate into Tregs rather than T effector cells. For example, immature DCs (iDCs) are poorly immunogenic because of low surface expression of costimulatory molecules and only modest MHC II levels. Therefore, iDCs themselves are tolerance inducers under steady state conditions. Thus, in some embodiments, the scaffold provides low surface expression of costimulatory molecules and only modest levels of MHC II (e.g., relative to immune activating conditions discussed above), to induce naïve T cell to differentiate into Tregs. Different populations of Tregs can require different levels of costimulation provided by DCs. A strong CD80/CD86 signal may be sufficient in maintaining thymus-derived Tregs but low or no costimulation may be needed for maintenance Foxp3+ Tregs.

In some embodiments, the scaffold mimics tolerogenic APCs by presenting MHC II complexed with a tolerogenic antigen alone or in combination with an MHC II costimulatory molecule such as ligand for CD4, CD25, or a combination thereof. Ligands for CD4 and CD25 include, but are not limited to, antibodies that specifically bind to CD4 or CD25 (e.g., anti-CD4 and anti-CD25 antibodies).

Besides costimulatory molecules, DCs can also display membrane receptors that may modulate T effector cells during activation. For example, immunoglobuline-like transcripts (ILT) receptors, such as ILT4, can interacts with MHC I molecules on T cells and in inhibit their activation. Upregulation of PD-1 occurs after repetitive stimulations of T cells (e.g., in chronic viral infections) and is a characteristic of "exhausted" T cells. Programmed Death-1 (PD-1) is a member of the CD28 family of receptors that delivers a negative immune response when induced on T cells. The primary result of PD-1 ligation by its ligands is to inhibit signaling downstream of the T cell Receptor (TCR). Therefore, signal transduction via PD-1 usually provides a suppressive or inhibitory signal to the T cell that results in decreased T cell proliferation or other reduction in T cell activation. B7-H1 is the predominant PD-1 ligand causing inhibitory signal transduction in T cells. Effects facilitated by PD-1 resemble in most parts IL-10 receptor (IL-10R) pathways such as limitation of PI3K activation and restriction of costimulatory signaling. Additionally, signaling through CTLA-4 delivers a negative signal that inhibits T cell proliferation, IL-2 production, and cell cycle progression (Krummel and Allison, J. Exp. Med., 183:2533-2540 (1996); and Walunas, et al., J. Exp. Med., 183:2541-2550 (1996)).

Thus, in some embodiments in which immune tolerance is desired, the scaffold presents one or more ligands or co-receptors that reduce or reverse immune stimulation of T cells such as helper T cells, cytotoxic T cells, and/or other effector T cells.

Exemplary ligands and agonists include ligands or agonists that activate PD-1. Natural ligands for PD-1 include PD-L1 (also referred to as Programmed Death 1 Ligand 1, Programmed Cell Death 1 Ligand 1, PDCD1L1, B7H1, and CD274) and PD-L2 (also referred to as Programmed Death 1 Ligand 2, Programmed Cell Death 1 Ligand 2, B7-DC, PDCD1L2, and CD273, and functional fragments and variants thereof. Other types of PD-1 agonists include PD-1 agonistic antibodies, small molecules, and aptamers that include RNA or DNA molecules that can be substituted for antibodies. In some embodiments, a PD-1 agonist is a soluble form of a PD-1 ligand (e.g., soluble PD-L1, soluble PD-L2). Soluble forms of PD-1 ligands typically include the extracellular domain of the ligand, or a portion thereof sufficient to bind to, and agonize, PD-1. In some embodiments, a PD-1 agonist is a soluble PD-1 ligand fused to a heterologous polypeptide (e.g., such as an Fc region of an immunoglobulin). In some embodiments, a PD-1 ligand is fused to an Fc portion of a human IgG1. PD-1 ligand-Fc fusions are referred to herein PD-L1-Ig and PD-L2-Ig. PD-L1-Ig and PD-L2-Ig are described, e.g., in Freeman et al., *J. Exp Med.* 2000 Oct. 2; 192(7): 1027-1034; Latchman et al., *Nat Immunol.,* 2001 March; 2(3):261-8; Watson et al., *Invest Ophthalmol Vis Sci.* 2006 August; 47(8):3417-22; and Youngnak et al., *Biochem Biophys Res Comm.* 2003; 307: 672-677.

Exemplary ligands or agonist include ligands or agonists that activate CTLA-4. CTLA-4 is expressed by activated T cells and transmits an inhibitory signal to T cells. CTLA-4 is homologous to the T-cell co-stimulatory protein, CD28, and both molecules bind to CD80 and CD86, also called B7-1 and B7-2 respectively, on antigen-presenting cells. Thus is some embodiments, the scaffold presents a natural ligand of CTLA-4 such as CD80 and CD86 or functional fragments and variants thereof. CTLA-4 binds CD80 and CD86 with greater affinity and avidity than CD28 thus enabling it to outcompete CD28 for its ligands. Other types of CTLA-4 agonists include CTLA-4 agonistic antibodies, small molecules, and aptamers which include RNA or DNA molecules that can be substituted for antibodies. Soluble forms of CTLA-4 ligands typically include the extracellular domain of the ligand, or a portion thereof sufficient to bind to, and agonize, CTLA-4. In some embodiments, a CTLA-4 agonist is a soluble CTLA-4 ligand fused to a heterologous polypeptide (e.g., such as an Fc region of an immunoglobulin). In some embodiments, a CTLA-4 ligand is fused to an Fc portion of a human IgG1. CTLA-4 fusion proteins, include, for example, CTLA-4 Ig (abatacept), and belatacept that contains two amino acid substitutions (L104E and A29Y) that markedly increase its avidity to CD86 in vivo. CTLA-4-Ig fusion proteins compete with the co-stimulatory receptor, CD28 on T cells for binding to CD80/CD86 (B7-1/B7-2), and thus function to inhibit T cell activation.

In some embodiments, undesirable or aberrant antigen-specific immune responses are treated or prevented by adoptive immunotherapy using "regulatory" T cells (Tregs) activated by the compositions and methods disclosed herein.

Immunological self-tolerance is critical for the prevention of autoimmunity and maintenance of immune homeostasis. The ability of the immune system to discriminate between self and non-self is controlled by mechanisms of central and peripheral tolerance. Central tolerance involves deletion of self-reactive T lymphocytes in the thymus at an early stage of development (Rocha, et al., *Science,* 251:1225-1228 (1991); Kisielow, et al., *Nature,* 333:742-746 (1988)). Several mechanisms of peripheral tolerance have been described, including T cell anergy and ignorance (Schwartz, *Science,* 248:1349-1356 (1990); Miller, et al., *Immunol. Rev.,* 133:131-150 (1993)). Studies have provided evidence for the existence of a unique $CD4^{+}CD25^{+}$ population of professional regulatory/suppressor T cells that actively and dominantly prevent both the activation as well as the effector function of autoreactive T cells that have escaped other mechanisms of tolerance (Sakaguchi, et al., *J. Immunol.,* 155:1151-1164 (1995); Takahashi, et al., *Int. Immunol.,* 10:1969-1980 (1998); Itoh, et al., *J. Immunol.,* 162:5317-5326 (1999)). The elimination or inactivation of these cells resulted in severe autoimmune disease, and was also found to enhance immune responses to alloantigens and even tumors (Sakaguchi, et al., *J. Immunol.,* 155:1151-1164 (1995); Itoh, et al., *J. Immunol.,* 162:5317-5326 (1999); Shimizu, et al., *J. Immunol.,* 163:5211-5218 (1999)). Autoantigen-specific regulatory T (Treg) cells actively regulate autoimmunity and induce long term tolerance and have application as a strategy for inducing long-lived tolerance.

T cells can be obtained from the subject to be treated as described below, and a Treg enriched cell population can be obtained by negative and/or positive selection. An autoantigen-specific regulatory T (Treg) cell enriched composition is one in which the percentage of autoantigen-specific Treg cells is higher than the percentage of autoantigen-specific Treg cells in the originally obtained population of cells. In particular embodiments, at least 75%, 85%, 90%, 95%, or 98% of said cells of the composition are autoantigen-specific regulatory T cells. To maximize efficacy, the subpopulation is enriched to at least 90%, preferably at least 95%, and more preferably at least 98% Treg cells, preferably $CD4^{+}CD25^{+}CD62L^{+}$ Treg cells. Positive selection may be combined with negative selection against cells including surface makers specific to non-Treg cell types, such as depletion of CD8, CD11b, CD16, CD19, CD36 and CD56-bearing cells.

The Treg cells are activated in a polyclonal or antigen-specific manner ex vivo using the compositions, as described above, expanded, and administered to the subject to be treated. In another embodiment, a population of T cells not enriched for Treg cells is activated and expanded, and the Treg cells are selected from the expanded T cell population using appropriate positive and/or negative selection.

Adoptive immunotherapy using Treg cells can be used for prophylactic and therapeutic applications. In prophylactic applications, Treg cells are administered in amounts effective to eliminate or reduce the risk or delay the outset of conditions associated with undesirable activation, over-activation or inappropriate or aberrant activation of an immune response, including physiological, biochemical, histologic and/or behavioral symptoms of the disorder, its complications and intermediate pathological phenotypes presenting during development of the disease or disorder. In therapeutic applications, the compositions and methods are administered to a patient suspected of, or already suffering from such a condition associated with undesirable activation, over-activation or inappropriate or aberrant activation of an immune response to treat, at least partially, the symptoms of the disease (physiological, biochemical, histologic and/or behavioral), including its complications and intermediate pathological phenotypes in development of the disease or disorder. An amount adequate to accomplish therapeutic or prophylactic treatment is defined as a therapeutically- or prophylactically-effective amount.

With respect to allograft rejection or graft versus host disease, in a preferred embodiment, adoptive immunotherapy with Treg cells is initiated prior to transplantation of the allograft. In certain embodiments, the Treg cells can be administered to the subject for a day, three days, a week, two weeks or a month prior to a transplantation. In other embodiments, the Treg cells are administered for a week, two weeks, three weeks, one month, two months, three months or six months following a transplantation. In a preferred embodiment, Treg cells are administered both before and after a transplantation is carried out.

The outcome of the therapeutic and prophylactic methods is to at least produce in a patient a healthful benefit, which includes, but is not limited to, prolonging the lifespan of a patient, delaying the onset of one or more symptoms of the disorder, and/or alleviating a symptom of the disorder after onset of a symptom of the disorder. For example, in the context of allograft rejection, the therapeutic and prophylactic methods can result in prolonging the lifespan of an allograft recipient, prolonging the duration of allograft tolerance prior to rejection, and/or alleviating a symptom associated with allograft rejection.

In another embodiment, undesirable or aberrant antigen-specific immune responses are treated or prevented by adoptive immunotherapy by using the compositions to activate and expand T cells specific for IgE or CD40L.

Immune responses to foreign, sometimes innocuous, substances such as pollen, dust mites, food antigens and bee sting can result in allergic diseases such as hay fever, asthma and systemic anaphylaxis Immune responses to self-antigens such as pancreatic islet antigens and cartilage antigens can lead to diabetes and arthritis, respectively. The hallmark of the allergic diseases is activation of $CD4^+$ T cells and high production of IgE by B cells, whereas the salient feature of autoimmune diseases are activation of $CD4^+$ T cells and over production of inflammation cytokines. Activated $CD4^+$ T cells transiently express the self antigen CD40L.

Cytotoxic T lymphocytes (CTLs) specific for antigenic peptides derived from IgE molecule can be generated ex vivo using the artificial antigen presenting cells and methods disclosed herein presenting antigenic IgE peptides. These IgE specific CTLs can be administered to a subject to lyse the target cells loaded with IgE peptides and inhibit antigen specific IgE responses in vivo. These IgE specific CTLs can also be used to prevent or treat the development of lung inflammation and airway hypersensitivity.

Similarly, cytotoxic T lymphocytes (CTLs) specific for antigenic peptides derived from CD40L can be generated ex vivo using the artificial antigen presenting cells and methods disclosed herein presenting antigenic CD40L peptides. These CD40L specific CTLs can be administered to a subject to lyse target activated $CD4^+$ cells in vivo. These CD40L specific CTLs can be used to inhibit CD4-dependent antibody responses of all isotypes in vivo.

The polymeric layer can also provide immunosuppressive signals. For example, interleukin 10 (IL-10) produced by tolerogenic iDCs is a prerequisite for Treg induction in a variety of different tolerance models like allergy and autoimmunity. Other factors secreted by tolerogenic DCs include TGF-β, which can be delivered in paracrine fashion to T cells alone or in combination with IL-2. Thus, in some embodiments, the polymeric layer provides controlled release of one or more anti-inflammatory cytokines.

The polymeric layer can be used for controlled release of immunosuppressants Immunosuppressants (also referred to herein as immunosuppressant agents, immunosuppressant drugs, immunosuppressive agents, and immunosuppressive drugs) Immunosuppressants are known in the art and include glucocorticoids, cytostatics (such as alkylating agents, antimetabolites, and cytotoxic antibodies), antibodies (such as those directed against T-cell receptors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod). The dosage ranges for immunosuppressant agents are known in the art. The specific dosage will depend upon the desired therapeutic effect, the route of administration, and on the duration of the treatment desired. For example, when used as an immunosuppressant, a cytostatic maybe administered at a lower dosage than when used in chemotherapy.

Immunosuppressants include, but are not limited to, FK506, prednisone, methylprednisolone, cyclophosphamide, thalidomide, azathioprine, and daclizumab, physalin B, physalin F, physalin G, seco-steroids purified from *Physalis angulata* L., 15-deoxyspergualin, MMF, rapamycin and its derivatives, CCI-779, FR 900520, FR 900523, NK86-1086, depsidomycin, kanglemycin-C, spergualin, prodigiosin25-c, cammunomicin, demethomycin, tetranactin, tranilast, stevastelins, myriocin, gliotoxin, FR 651814, SDZ214-104, bredinin, WS9482, mycophenolic acid, mimoribine, misoprostol, OKT3, anti-IL-2 receptor antibodies, azasporine, leflunomide, mizoribine, azaspirane, paclitaxel, altretamine, busulfan, chlorambucil, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, etoposide, teniposide, vinblastine, vincristine, vinorelbine, procarbazine, asparaginase, pegaspargase, octreotide, estramustine, and hydroxyurea.

Other immunosuppressive agents include, for example, antibodies against other immune cell surface markers (e.g., CD40) or against cytokines, other fusion proteins, e.g., CTLA-4Ig, or other immunosuppressive drugs (e.g., cyclosporin A, FK506-like compounds, rapamycin compounds, or steroids).

As used herein, the term “rapamycin compound” includes the neutral tricyclic compound rapamycin, rapamycin derivatives, rapamycin analogs, and other macrolide compounds which are thought to have the same mechanism of action as rapamycin (e.g., inhibition of cytokine function). The language “rapamycin compounds” includes compounds with structural similarity to rapamycin, e.g., compounds with a similar macrocyclic structure, which have been modified to enhance their therapeutic effectiveness. Exemplary Rapamycin compounds, as well as other methods in which Rapamycin has been administered are known in the art (See, e.g. WO 95/22972, WO 95/16691, WO 95/04738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

Rapamycin analogs include, for example, everolimus, ridaforolimus, remsirolimus, umirolimus, and zotarolimus.

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506 like compounds include, for example, those described in WO 00/01385. Preferably, the language "rapamycin compound" as used herein does not include FK506-like compounds.

Furthermore, in addition or alternative to immune checkpoint modulators being tethered or otherwise attached to the scaffold, soluble modulators such as PD-1 or CTLA-4 agonist small molecules, antibodies, and fusion proteins can be released in a paracrine-like fashion from the polymeric layer.

As mentioned elsewhere herein, the molecules tethered to the substrate and those released from the polymeric layer can be selected based on the target cell type and desire modulation. In exemplary immunosuppressive or tolerance-inducing embodiments, CD4 ligands such as anti-CD4 and MHC class II with the peptide for which tolerance is desired can be used as signals I and II. The active agent to be delivered using the polymer layer can be an anti-inflammatory cytokine or cytokines as TGF-beta in combination with IL-2 or IL-10, or other tolerogenic cytokines and/or small molecule tolerogenic drugs.

Thus, in an exemplary embodiment, the immune activating strategy discussed can be modified as follows.

Signal 1: A T cell recognition signal (e.g., Clonal: Tolerogenic Peptide/Major Histocompatibility Complex II). This signal selects for the phenotype or specificity of cells of interest.

Signal 2: A Co-stimulatory amplification signal (anti-CD4, anti-CD25, etc.), and/or an immune checkpoint agonist (e.g., agonist anti-PD-1 antibody, agonist anti-CTLA-4 antibody, etc0. This signal amplifies the recognition signal and initiates the T cell tolerance program, and/or induces T cell suppression or anergy.

Signal 3: Paracrine delivery of one or more tolerogenic cytokines, drugs, or soluble immune checkpoint agonists (e.g., IL-10, or TGFbeta+IL-2).

Signal 4: Laminar Flow Laminar flow enhances the quality of expanded T cells.

Signal 5: High surface area of presentation of other signals, which is how T cells are expanded in the lymph nodes in vivo.

Signal 6: Electrostatics. T cell expansion is best performed under specific charge.

Preferably the charge should be a negatively charged zeta potential between 0 to −10, although the range is between 10 and −100. Neutral is most preferable but slightly negative is acceptable.

The structure of the cartridge provides signals 1-3 and 5-6. When coupled to a means of providing a laminar flow (e.g., a pump and media reservoir), all six signals are present in the cartridge microenvironment. The cartridge can be viewed as an artificial lymph node used outside the body for cell expansion.

3. Antigen Presenting Cells

The bioreactors can also be used to modulate antigen presenting cells (APC) including, but not limited to, dendritic cells, macrophages, and B cells. Depending on which signaling molecules and active agents are selected, the captured APC's can be induced to stimulate naïve T cells to have an effector immune response against the antigen, or, alternatively, the captured APC can be induced to drive tolerance induction and maintain immune-homeostasis.

For example, immature dendritic cells encounter potential antigens via innate pattern-recognition receptors (PRRs), such as toll-like receptors (TLRs) or c-type-lectin receptors, take up the antigens via micropinocytosis and degrade them into smaller peptides, which can be presented to other immunes cells by surface displayed major histocompatibility complexes. The antigen uptake triggers maturation processes of DCs that result in the upregulation of costimulatory molecules like CD40, CD80, CD86 and secretion of proinflammatory cytokines/interleukines (IL) like IL-1β, IL-12, IL-6, and TNF as well as more MHC-peptide complexes. The mature DCs upregulate trafficking receptors, such as CCR7, which enable them mobilize in search of naïve T cells which recognize the MHC-peptide complex with an antigen-specific T cell receptor. Sufficient activation and antigen recognition subsequently activate T cells to differentiate into T helper cells or cytotoxic T effector cells.

Alternatively, as introduced above, DCs do also exhibit regulatory functions in order to maintain central and peripheral tolerance. During steady state, DCs capture self-antigens and silence auto-reactive T cells. So-called tolerogenic DCs bear low amounts of costimulatory molecules on their surface and exhibit reduced secretion of proinflammatory IL-12 but high production of anti-inflammatory cytokines like IL-10. Tolerogenic DCs provide insufficient stimulatory signals for T cells and therefore drive naïve T cells to differentiate into Tregs rather than T effector cells. DCs which are not activated after phagocytosis of, for example apoptotic cells, exhibit a tolerogenic function via the secretion of transforming-growth-factor-beta (TGF-β) and subsequent induction of Foxp3+ Tregs in the draining lymph nodes.

A cell adhesion protein can be displayed by the substrate to capture the cells in the bioreactor. For example, in some embodiments, the substrates display a ligand, such as an antibody, that binds to, or can be bound by, an APC cell surface protein. In exemplary embodiments, the cell surface protein is D11c, CD11b, or a combination thereof.

Antigen (e.g., soluble polypeptide) can be released from the polymeric layer, and internalized by the antigen presenting cells. Exemplary antigens are provided above and can be selected based on the desired modulation. For example, if the desired modulation is to prime the APC to induce an immune response against cancer, the antigen may be a cancer antigen. In other embodiments, where the desired modulation is to prime the APC to induce an immune response against an infection, the antigen may be from the infectious agent (e.g., a viral or bacterial antigen). Embodiments in which APCs are primed to induce an active immune may also include release of one or more proinflammatory immunomodulators (e.g., one or more proinflammatory cytokines) from the polymeric matrix.

If the desired modulation is to prime APC to drive tolerance induction and maintain immune-homeostasis, the antigen may be tolerogenic antigen, for example a self-peptide, allergen, etc. Embodiments in which APCs are primed to induce an active immune response may also include release of one or more anti-inflammatory immunomodulators (e.g., one or more anti-inflammatory cytokines, or immunosuppressive drugs (e.g., rapamycin, mycophenolic acid, retinoic acid, etc.) from the polymeric matrix.

B. Targets Cells

1. Cell Types

The target cells are typically antigen presenting cells including, but not limited to, dendritic cells, macrophages, B cells and/or T cells.

The T cells modulated by the cartridge can be any cell which express a T cell receptor, including α/β and γ/δ T cell receptors. T cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In preferred embodiments, the T cells that are activated are $CD8^+$ T cells.

A source of cells can be a human or another organism in which an immune response can be elicited, e.g., mammals. The subject can be, but need not be, the subject to whom the modulated cells are subsequently administered for adoptive immunotherapy. Examples of subjects include humans, dogs, cats, mice, rats, and transgenic species thereof, although humans are preferred. Cells can be obtained from a number of sources, including peripheral blood leukocytes, bone marrow, lymph node tissue, spleen tissue, and tumors. In a preferred embodiment, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through, e.g., a PERCOLL™ gradient.

A specific subpopulation of T cells, such as $CD4^+$ or $CD8^+$ T cells, can be further isolated by positive or negative selection techniques. For example, negative selection of a T cell population can be accomplished with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate $CD4^+$ cells, a monoclonal antibody cocktail typically includes antibodies to CD14, CD20, CD11b, CD16, HLA-DR, and CD8. The process of negative selection results in an essentially homogenous population of the desired T cell population.

In some embodiments, the cells are Tumor Infiltrating Lymphocytes (TILS). Typically, $1\times10^5$ TILS can be extracted from a 1-2 gram tumor mass.

Generally, about 5 μg/ml of scaffold can be used for about $5\times10^5$ (e.g., TILS). 1 gram of CNTs will treat between about $1\times10^{10}$ and $2\times10^{10}$ cells. The cartridge may be customized according to the subject and the condition or disease to be treated. In some embodiments, the cartridge contains at least one polyclonal T cell receptor activator, such as an anti-T cell receptor antibody. Polyclonal T cell activation can be useful because it can expand a T cell population more quickly than antigen-specific methods. The expanded polyclonal T cells can then be sorted to select for T cells with a specificity for the epitopes of interest. In another embodiment, the scaffold includes MHC class I or MHC class II molecules bound to antigens of interest for antigen-specific T cell activation. The MHC polypeptides used in device are preferably selected to match the MHC alleles expressed by the subject to be treated. The antigen is selected based on the condition or disease to be treated or prevented. The antigen may be derived from the subject to be treated (e.g., cancer antigen(s) from the subject's cancer).

In some embodiments, the T cells are chimeric antigen receptor T cells (CAR-T cells), or T cells that are otherwise modified ex vivo prior to, during, or after, being contacted with the cartridge to activate and/or expand the T cells.

T cells can be modified to include a chimeric antigen receptor by, for example, the use of the polymer (e.g., nanoparticles) on the support or scaffold (e.g., CNT) as a transfection agent. This is possible using, for example, a viral vector of choice incorporated in the polymer system on the scaffold. The nanoparticle platform, alone, has been demonstrated in multiple studies as a transfection system with DNA, mRNA and siRNA. Oligonucleotide incorporation with nanoparticles is achieved via electrostatic complexation with a cationic moiety (typically PEI or Polylysine) encapsulated in the NP or on the surface.

T cells can also be transfected by electrostatic complexation of the vector to the base support, scaffold, or polymer surface using a biodegradable linker. This follows the same principles as above except the vector is attached to a cationic host on the surface itself. The cationic host is linked to the surface via biodegradable linker (a detaching tether). T cells interfacing with the device will be transfected by the vector with a higher efficiency compared to 3D transfection.

2. Incubation Periods

The cells are typically contacted with the cartridge in appropriate medium. The cells are contacted with the cartridge having an effective amount of scaffold for a period of time necessary for the desired modulation of the cells, expansion of the cells, or a combination thereof.

In certain embodiments, it may be desirable to separate the cells from the cartridge after a period of about 2, 3, 4, 5, 6, 7, 8, 9, 10, or 11 days. In certain embodiments, it may be desirable to separate the cells from the device after a period of less than one day, such as after about an hour, or 2, 3,4, 5, 6, 7, 8, 9, 10, 11, 12, 13, 14, 15, 16, 17, 18, 19, 20, 21, 22, or 23 hours. Generally, the cells can be suitably activated and expanded after between about 1 and 7, or about 2-6, or 3 and 5 days in contact with the cartridge. In some embodiments, the cells are incubated with the cartridge for 2, 3, 4, 5, or 6 days.

In some embodiments, the cells may be maintained in long-term culture following the initial activation and stimulation, by separating the cells from the cartridge after stimulation. However, this is generally not necessary and can be excluded from the process. Thus, in some embodiments, the cells are not maintained in long-term culture, and used for adaptive cell therapy upon their separation from the stimulus.

The rate of cell proliferation can be monitored periodically (e.g., daily) by, for example, examining the size or measuring the volume of the cells, such as with a Coulter Counter. In this regard, a resting T cell has a mean diameter of about 6.8 microns, and upon initial activation and stimulation, in the presence of the stimulating ligand, the T cell mean diameter can increase to over 12 microns by day 4 and begin to decrease by about day 6. The T cells may be stimulated through multiple rounds of activation. For example, when the mean T cell diameter decreases to approximately 8 microns, the T cells may be reactivated and re-stimulated to induce further proliferation of the T cells.

The rate of T cell proliferation and time for T cell stimulation or re-stimulation can be monitored by assaying for the presence of cell surface molecules, such as, CD154, CD54, CD25, CD137, CD134, which are induced on activated T cells. CD8, CD4, CD62L, CD44, CD25, FOXP3 and CCR7 can be used to distinguish between slow effector memory cells, central memory, cytotoxic, helper and Treg cells.

Cytokines secretion such as IFN, IL-2, IL-12 and surface expression of IL-15 receptor can also be used as measures of activation.

3. Administration

Following modulation and/or expansion of the cells, they can be administered to the subject in amounts effective to induce the desired therapeutic result (e.g., immune response, tolerance, etc.). The immune response induced in the animal by administering the compositions may include cellular immune responses mediated by $CD8^+$ T cells, capable of killing tumor and infected cells, and $CD4^+$ T cell responses. Humoral immune responses, mediated primarily by B cells that produce antibodies following activation by $CD4^+$ T cells, may also be induced. In a preferred embodiment, the immune response is mediated by cytolytic $CD8^+$ T cells. A variety of techniques which are well known in the art may be used for analyzing the type of immune responses induced by the compositions and methods disclosed herein (Coligan et al., *Current Protocols in Immunology*, John Wiley & Sons Inc. (1994)).

V. Systems for T Cell Modulation

A. Components of the System

Figure 2:
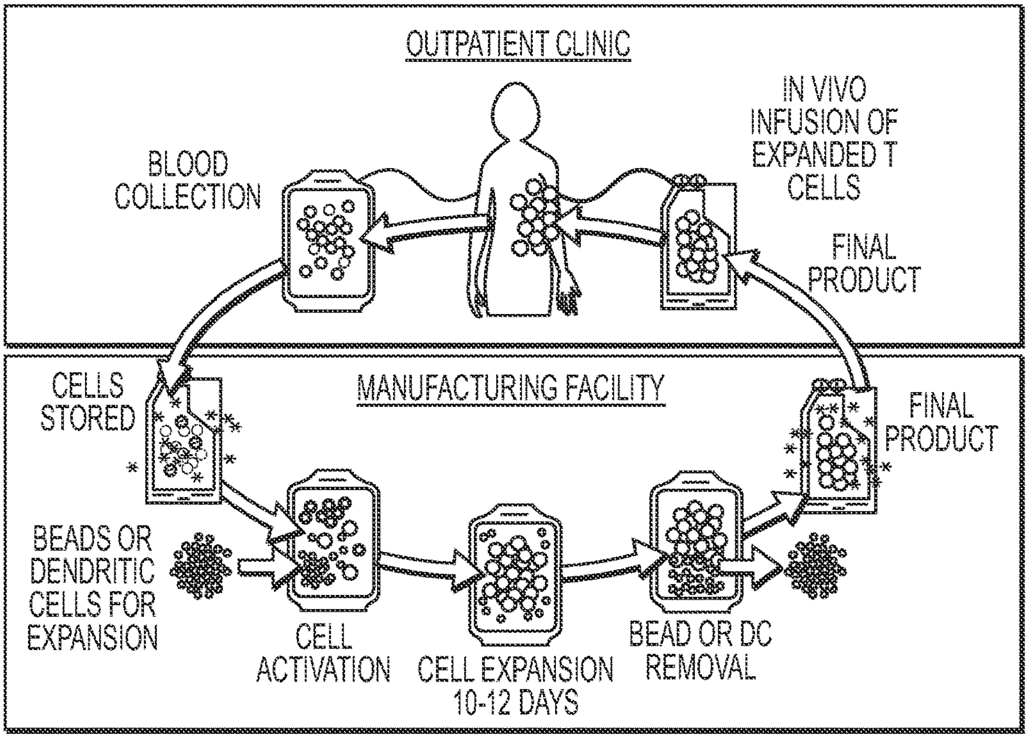
FIG. 2 is a simplified illustration of conventional, ex vivo therapeutic T cell activation and expansion for adoptive immunotherapy. Blood is collected from a subject at an outpatient clinic and transferred to a manufacturing facility where the blood cells may be stored. Lymphocytes from the blood sample are isolated and incubated with an activation stimulus. Typically, activation stimuli are natural antigen-presenting cells such as dendritic cells (DCs) or artificial beads presenting stimulatory and co-stimulatory protein signals. Cells are also supplemented with cocktails of growth factors such as Interleukin-2 and IL-23 or other combinations. The combinations of cells leads to T cell activation and expansion. After 10-12 days, or a sufficient time that allows for expansion of up to a billion cells from 10,000 cells the artificial stimuli are removed or natural stimuli are left to degrade during the incubation period. The final product of activated and expanded T cells are transferred back to the outpatient clinic for infusion into the subject in a process called "adoptive immunotherapy"

In some embodiments, the cartridge is part of a larger system for cell modulation. The availability of cell therapy in a clinical setting can be hindered by the complexity and limitations of traditional manufacturing procedures such the exemplary T cell therapy process illustrated in FIG. 2. Blood is collected from an outpatient clinic as a source of T cells. The blood and/or isolated T cells are stored and transferred to a manufacturing facility. The cells are contacted with dendritic cells or traditional artificial antigen presenting cells (e.g., dynabeads) to induce T cell activation. The cells are typically allowed to expand for 10-12 days, at which time the dendritic cells and/or artificial antigen presenting cells are separated from the expanded T cells to yield a final T cell product. The T cells are returned to the clinic where they are infused into the subject. The process is complex, inefficient, expensive, and lengthy. Much of the process often takes place at a manufacturing facility that is separate for the point-of-care for the patient, and the T cells often have limited efficacy owed to deficiencies in the activation or expansion process.

The cartridges can be integrated into a system that is suitable for use at the point of care.

For example, in some embodiments, the system includes a vessel for the storage or passage of blood, wherein the vessel contains the cartridge. The system can also include one or more lines that allow blood, other fluids, or a combination thereof to flow to and/or from the vessel, as well as valves and other means of controlling the flow of the blood and other fluids into and out of the cartridge.

Vessels suitable for the storage or passage of blood include those vessels which are physiologically inert and clinically suitable to contain blood and blood products to be administered to a subject. These include blood bags (for example, blood bags used to store donated blood for future transfusion), catheters, cannulae, a portion of a flow line (a flow line being an apparatus used for delivery of fluids to a subject, for example intravenously or intra-arterially), syringes, and the components of extracorporeal circuits (for example those used for cardiopulmonary bypass or haemodialysis, and cardiac pumps). Such vessels can be used in combination: for example, blood that has passed through an extracorporeal circuit can pass through a flow line and into a subject via a cannula, any one or more of which may include a cartridge.

In some embodiments, the vessel is a flow line for delivery of blood to or from a patient, for example, from a blood bag or extracorporeal circuit or an IV line from the subject. In certain preferred embodiments, the vessel is a housing or chamber. For example, the housing or chamber can be inline with a flow line. Thus in some embodiments the system includes a cartridge contained by the flow line that is housed in a flow chamber or housing. A flow chamber or housing can be arranged so as to allow a sufficient volume of the blood (an thus a sufficient number of T cells, APCs, etc.) to contact the cartridge and bind to the scaffold. In some embodiments, the system can maintain an acceptable flow rate of the blood through the flow chamber and into the patient. In some embodiments, the flow of blood to and/or from the subject is can be increased, decreased, or stopped completely using one or more valves in the system.

The cartridge can be partially or wholly integrated with the vessel. For example, when the cartridge is partially integrated, the cartridge can be anchored to the vessel from a site on the cartridge. In some embodiments, the cartridge is wholly integrated with the vessel. In such embodiments, the support may form the inner luminal surface of the vessel, for example the cartridge may be part of the inner surface of the flow line or housed in, and form the structure of, a flow chamber. For example, the inner structure of the flow chamber may be the cartridge.

In preferred embodiments, a vessel housing the cartridge is gas permeable.

Typically, part or all of the system can be placed inline with (otherwise includes) an intravenous line or other access point in the subject, and is also removable therefrom. In this way, the cartridge can be connected to the subject and blood drawn into or through the cartridge for an effective amount of time to collect an effective number of cells in the cartridge, vessel, blood bad, or there comment of the system. The system can later be removed from the subject to continue activation and expansion of the cells. Subsequently, the system can be placed inline with the subject again and the cells returned to the subject.

Some embodiments also include a port or other point that allows fluids including, but not limited to saline, to enter the cartridge. Saline or other fluids may be used to prime the cartridge before it is contacted with the subject's blood, and/or to facilitate return of the cells after activation and expansion.

Figure 3:
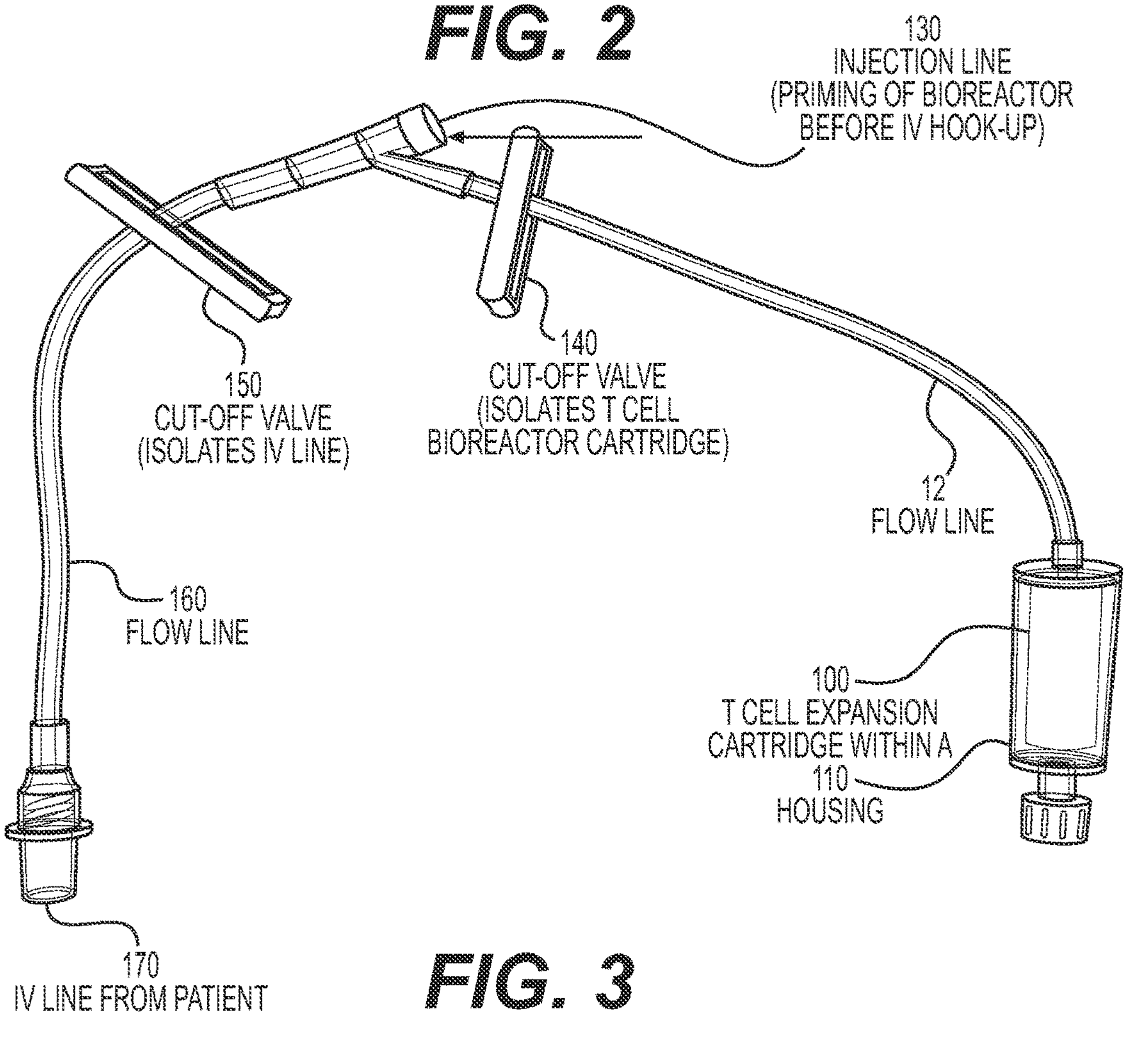
FIG. 3 is an illustration of the device. The end cartridge which resembles a filter is the site of T cell activation and expansion. The tubing are lines that facilitate connection to IV catheter lines for priming the device with saline and blood draw into the device. As noted, this system is the end-product that is envisioned to be commercialized for in situ draw of blood cells, expansion of lymphocytes and following incubation of the cartridge end for 3-5 days, re-infusion of the expanded product back into the patient.

An exemplary system is illustrated in FIG. 3. The figure illustrates a cell cartridge (100) inside a cartridge housing (110). The housing (110) is connected to an injection port (130) with a flow line (120). The injection port is also connected to an IV line, or connector thereto (170) by a second flow line (160). Cut-off values (140) and (150) can be used to control or stop flow along flow line (120) and/or (160) respectively. In some embodiments the cut-off valves are clamps.

Figure 4:
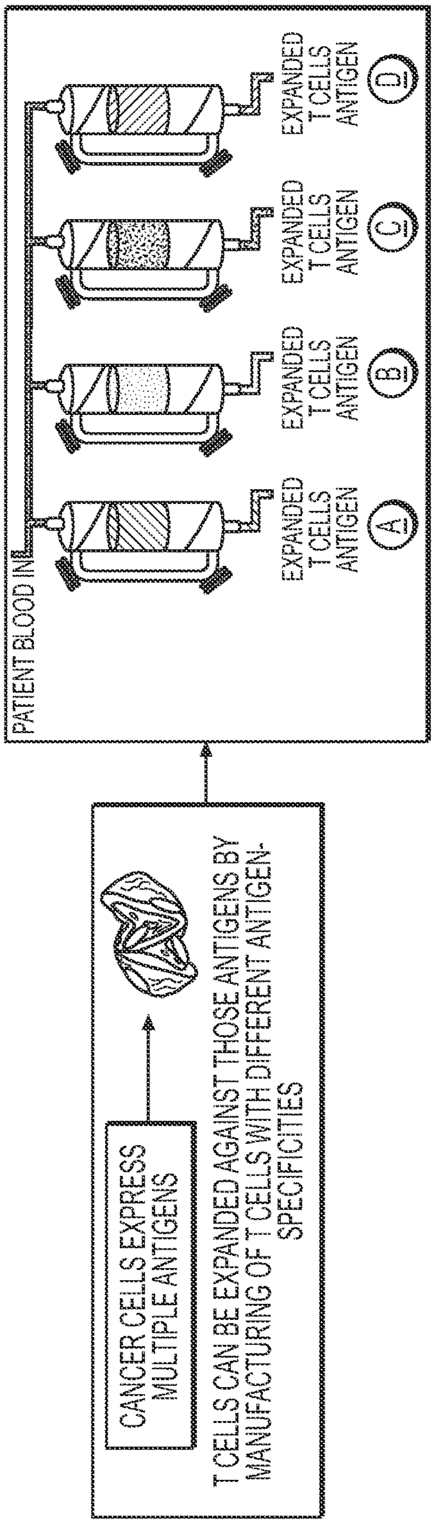
FIG. 4 is a schematic showing that cancer cells express multiple antigens, and an exemplary bioreactor configuration in which four (4) bioreactor cartridges are aligned in parallel, wherein each bioreactor is utilized to activate T cells against different cancer antigen (i.e., "expanded T cell antigen" A, B, C, or D). The combination of the T cells from these bioreactors would be T cells reactive against the four cancer antigens.

In some embodiments, the system includes two or more cartridges. The cartridges may be of the same or different design. For example, the two or more cartridges may be composed of different base supports, different polymers, different scaffolds, and/or different cell ligands. The different cartridges can be used to increase the total number of cells that are modulated, to increase the number of antigens recognized by the cells, increase the different types of cells modulated, or a combination thereof. For example, in some embodiments, two, three, four, or more cartridges with different cell ligands are used to activate T cells against two, three, four, or more antigens. In some embodiments a cartridge may induces and/or expand APC maturation against a target antigen, while another cartridge activates and/or expands T cells against the same or a different antigen. The cartridges can be connected serially, in parallel, or unconnected. An exemplary system illustrating the use of four different cartridges connected in parallel to a flow line is exemplified in FIG. 4.

In some embodiments, the system includes packaging for part or all of the system. For example, in some embodiments, the cartridge, housing, one or more flow lines, one or more ports, and one or more valves or clamps are package in bag or other container for transportation and delivery. In some embodiments, the system is sterilized before package, or preferably at least before use.

B. Methods of Using the Systems

Before use, the cartridge can be primed with saline or another fluid.

Typically, when used as part of a system such as those described above, a flow line from an access point in the subject (e.g., an arterial port or flow line, etc.) can be used to deliver blood to the vessel containing the cartridge and bring blood from the subject into contact with the cartridge. In some embodiments, for example, those in which the source of the cells is a tumor (e.g., TILs) or otherwise isolated free from blood or another source, the cells can be introduced to the cartridge in a saline, PBS, media or another suitable fluid rather than by connecting the system to the subject and allowing the subject's blood to populate the cartridge with T cells. In some embodiments, the cartridge is contacted with blood without connecting the system to the subject. For example, in some embodiments, the cartridge is contacted with whole blood or a fraction thereof containing leukocytes.

In some embodiments, blood flows through the cartridge and is return to the subject (e.g., through a venous port or flow line, etc.) while the cartridge collects or captures an effective amount of cells. In this way, the system can be similar to an inline blood filter with the disclosed cartridge replacing the blood filter. In some embodiments, the blood does not flow through the cartridge, and is instead left to pool in the cartridge until the housing or other vessel is full.

The system or a part thereof including the cartridge can be disconnected from the subject. The cartridge can be incubated for an effective amount of time to modulate (e.g., active or suppress) and optionally expand the cells. A preferred incubation temperature is 37° C. The incubations period can be hours, days or weeks. Preferred incubation periods are days, for example, 1, 2, 3, 4, 5, 6, 7, 8, 9, 10, 11, or 12 days. In preferred embodiment, the cartridge is incubated at about 37° C. for about 1-5 days, or 2-4 days, or about 3 days.

In some embodiments, media is flowed into the bioreactor to facilitate cell modulation and expansion. The flow can be effective to create a shear rate that induces a physiological-like cell expansion. Exemplary flow rates include, but are not limited to, flowrates from 1 ml/min to 50 ml/min. Flow can be intermittent/pulsed or continuous. Media can be recycled through the reactor to conserve media and released growth factors. In some embodiments, the flow rate is between about 1 ml/min and about 25 ml/min, or about 1 ml/min and about 20 ml/min, or about 1 ml/min and about 15 ml/min, or about 1 ml/min and about 10 ml/min, about 1 ml/min and about 5 ml/min Low flow is 100 ul/min and high 10 ml/min.

After the cells are activated and/or expanded, the cells can be returned to a subject in need thereof. In some embodiments, the subject is the same subject from which the cells were withdrawn. In some embodiments, the subject to whom the cells are administered is a different subject from the one from whom the cells were harvested. The cells can be administered to the subject by, for example, a flow line connecting the cartridge to a vein of the subject via, for example a port, IV line, or other point of access.

Figure 5:
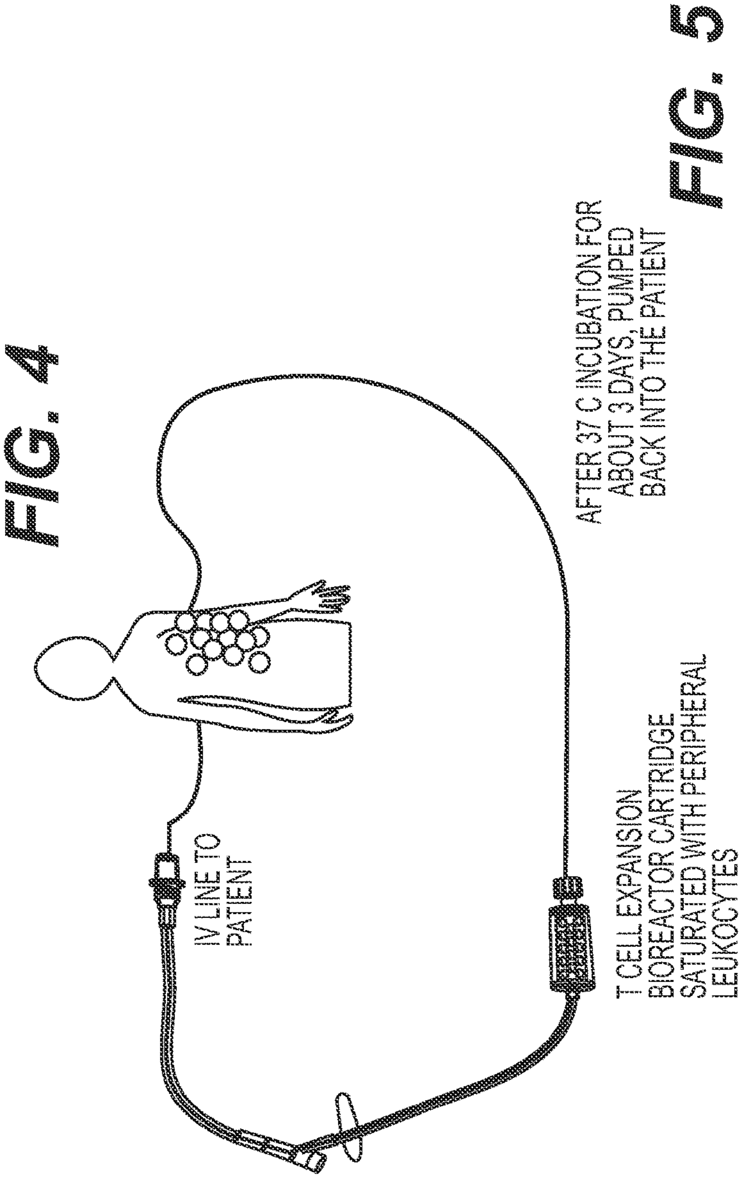
FIG. 5 is a schematic of an exemplary modified approach to ex vivo T cell activation and expansion. Blood is harvested from a subject in need of T cell therapy. Peripheral leukocytes are contacted with a bioreactor cartridge where they are activated and expanded for about 3 days at about 37° C. and then returned to the subject for adoptive cell therapy.
Figure 6:
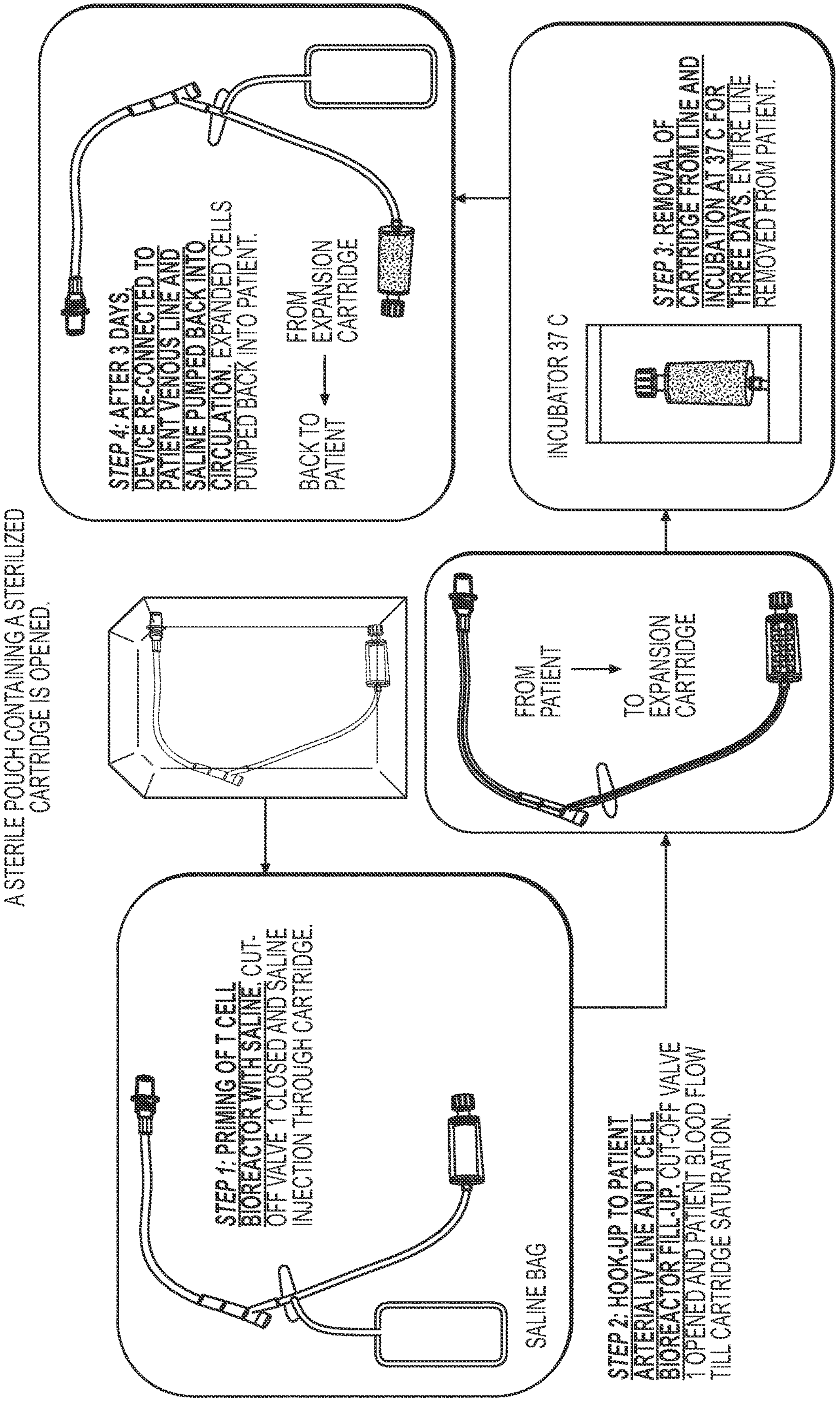
FIG. 6 is a schematic of materials, structure, and preparation of an exemplary system for ex vivo T cell activation and expansion. The system is shipped to users in sterile packaging. The bioreactor can be primed with a fluid such as saline delivered into the cartridge's housing via an injection port and flow line to facilitate wetting and reception of subsequent blood cells. The system can be connected to an arterial or venous IV line and the cut off valves opened, which allows the subject's blood to connect the bioreactor cartridge. After the cartridge is loaded with blood (e.g, T cells). Red blood cells are lysed in a special buffer in the entrance to the cartridge and lysed cells and proteins are flown out during the blood priming step. Only T cells specific to immobilized antigens are captured and expanded in the device. The device therefore functions as a lymphocyte filter during a blood draw. Once blood flow is terminated, the system removed, and the T cells allowed to activate and expand for about 3 days at 37° C. In some embodiments, the system is connected to a media reservoir that provides continuous or periodic media flow across or through the bioreactor.

Exemplary methods are diagramed in FIGS. 5 and 6.

VI. Subjects to Be Treated

In general, the compositions and systems are useful for treating a subject having or being predisposed to any disease or disorder to which the subject's immune system mounts an immune response. Subjects are typically treated by administering the subject an effective amount of ex vivo-treated cells. The ex vivo-treated cells can be T cells, APCs, or a combination thereof. The therapy can induce an active immune response or promote tolerance or homeostasis.

Treating a disease or disorder to which the subject's immune system mounts an immune response may include inhibiting or delaying the development of the disease or disorder or inhibiting or reducing the symptoms of the disease or disorder. The compositions are useful as prophylactic compositions, which confer resistance in a subject to subsequent tumor development or exposure to infectious agents. The compositions are also useful as therapeutic compositions, which can be used to initiate or enhance a subject's immune response to a pre-existing antigen, such as a tumor antigen in a subject with cancer, or a viral antigen in a subject infected with a virus.

The compositions are also useful to treat or prevent diseases and disorders characterized by undesirable activation, overactivation or inappropriate activation of the immune system, such as occurs during allergic responses, autoimmune diseases and disorders, graft rejection and graft-versus-host-disease.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, treatment against infectious agents with the compositions and systems may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

A. Subjects Infected with or Exposed to Infectious Agents

In some instances, the subject can be treated prophylactically, such as when there may be a risk of developing disease from an infectious agent. Infectious agents include bacteria, viruses and parasites. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

B. Subjects with or a Risk of Developing Malignant Tumors

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The compositions and method described herein may be useful for treating subjects having malignant tumors. Treating a subject having a malignant tumor includes delaying or inhibiting the growth of a tumor in a subject, reducing the growth or size of the tumor, inhibiting or reducing metastasis of the tumor, and inhibiting or reducing symptoms associated with tumor development or growth.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this technology is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided compositions and methods include, but are not limited to, the following: bladder, brain, breast, cervical, colo-rectal, esophageal, kidney, liver, lung, nasopharangeal, pancreatic, prostate, skin, stomach, uterine. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

C. Immunosuppressed Conditions

The compositions and systems are useful for treatment of disease conditions characterized by immunosuppression, including, but not limited to, AIDS or AIDS-related complex, idiopathic immunosuppression, drug induced immunosuppression, other virally or environmentally-induced conditions, and certain congenital immune deficiencies. The CNT compositions may also be employed to increase immune function that has been impaired by the use of radiotherapy of immunosuppressive drugs (e.g., certain chemotherapeutic agents), and therefore can be particularly useful when used in conjunction with such drugs or radiotherapy.

D. Subjects Exposed to Allergens

The compositions and methods are useful to treat and/or preventing allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may further alleviate allergic disease. These can be used to enhance blocking or tolerance inducing reactions.

E. Subjects with or at Risk of Developing Autoimmune Diseases or Disorders

The compositions and methods are useful for the treatment or prevention of autoimmune diseases and disorders. Exemplary autoimmune diseases include vasculitis, Wegener's granulomatosis, Addison's disease, alopecia, ankylosing spondylitis, antiphospholipid syndrome, Behcet's disease, celiac disease, chronic fatigue syndrome, Crohn's disease, ulcerative colitis, type I diabetes, fibromyalgia, autoimmune gastritis, Goodpasture syndrome, Graves' disease, idiopathic thrombocytopenic purpura (ITP), lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vitiligo, vasculitis, small vessel vasculitis, hepatitis, primary biliary cirrhosis, rheumatoid arthritis, Chrohn's disease, ulcerative colitis, sarcoidosis, scleroderma, graft versus host disease (acute and chronic), aplastic anemia, and cyclic neutropenia.

F. Subjects Undergoing or at Risk of Graft Rejection or Graft-Versus-Host Disease The compositions and methods are useful for the treatment or prevention of graft rejection or graft versus host disease. The methods and compositions can be used in the prevention or treatment of any type of allograft rejection or graft versus host disease for any type of graft, including a xenograft. The allograft can be an organ transplant, such as, but not limited to, a heart, kidney, liver, lung or pancreas. Alternatively, the allograft can be a tissue transplant, such as, but not limited to, heart valve, endothelial, cornea, eye lens or bone marrow tissue transplant. In yet other embodiments, the allograft can be a skin graft.

The present invention will be further understood by reference to the following non-limiting examples.

Example 1: Configuration Impacts on T Cell Activation

An experiment was designed to test the difference between the microparticles, nanoparticles, and scaffold for presentation of materials (e.g., anti-CD3, anti-CD28) for T cell activation. Tetrameric complexes, which are the gold standard for T cell activation, were also tested.

Figure 7:
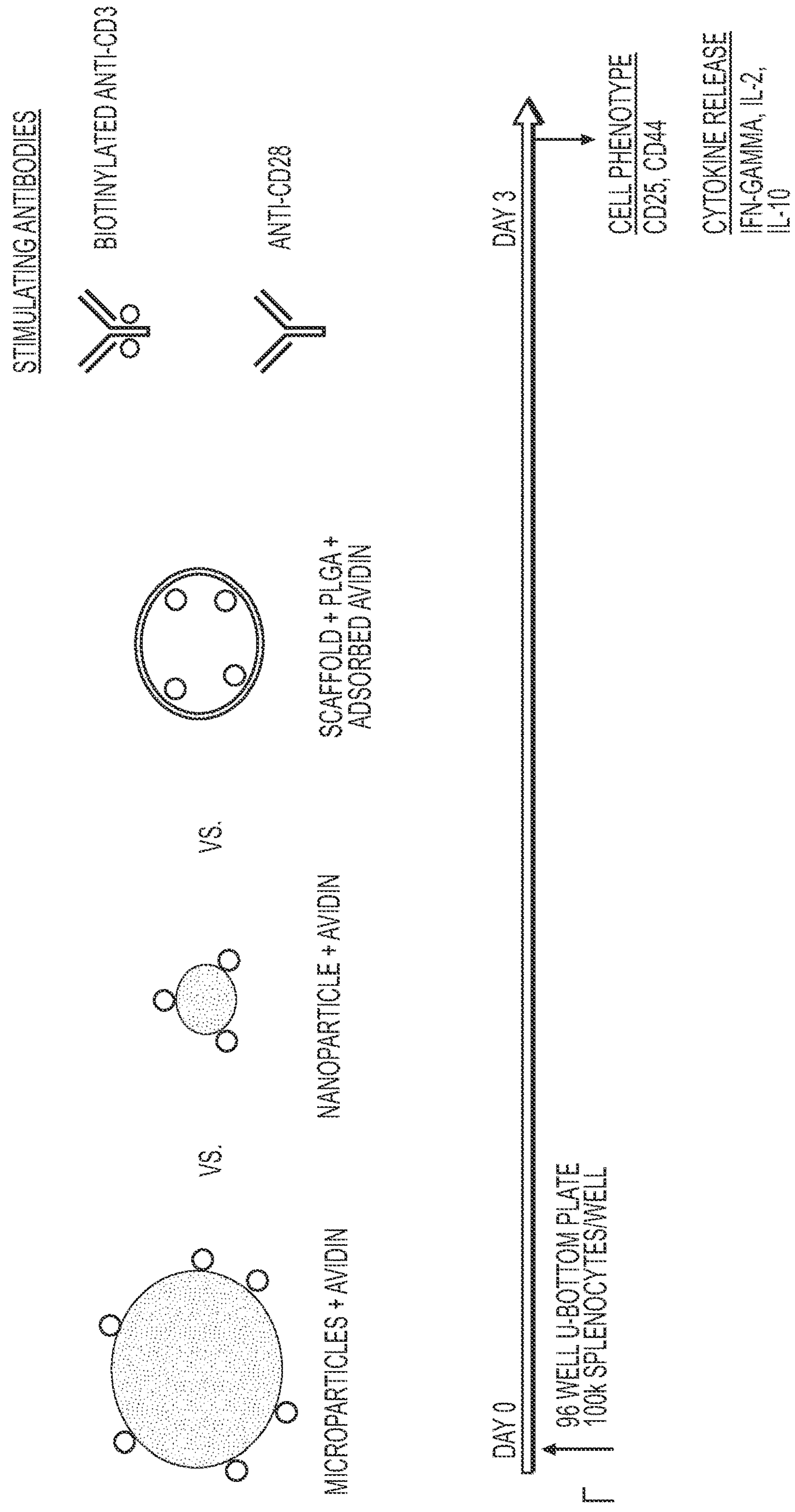
FIG. 7 is an illustration of an assay designed to test the difference in configurational design of the substrate and T cell activation. Here, microparticles, nanoparticles, soluble multivalent stimuli (tetrameric antibodies) and scaffold (the invention) are used as presentation stimulatory and co-stimulatory ligands (e.g., anti-CD3, anti-CD28) 1-10 ug/ml and 0.5-5 ug/ml respectively for T cell activation.
Figure 8B:
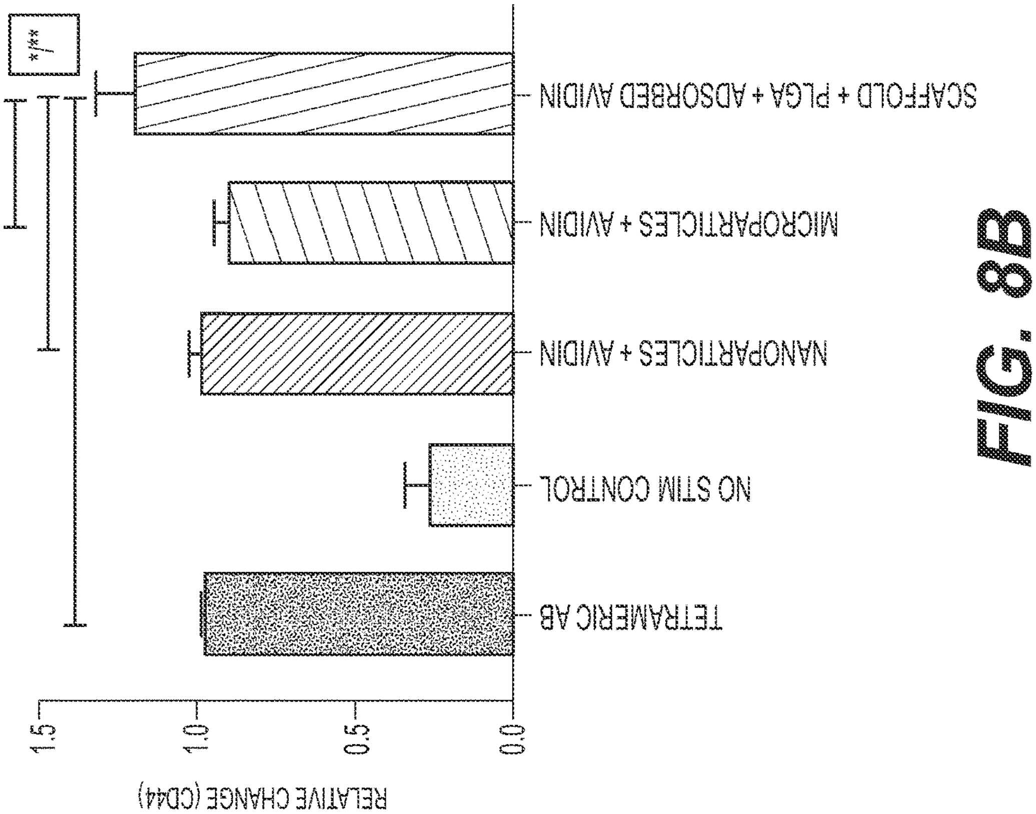
FIGS. 8A-8E Impact of artificial stimulus configuration on T cell activation. Three days post contact with the stimuli in tissue culture conditions (37 C, 95% CO2). Bar graphs showing relative change in CD25 expression (8A), relative change in CD44 expression (8B), IFN-gamma secretion (ng/ml) (8C), IL-2 secretion (ng/ml) (8D), and IL-10 secretion (ng/ml) (8E) for splenocytes incubated with soluble Ab, tetrameric Ab, no stimulation control, nanoparticles+avidin, microparticles+avidin, or scaffold+PLGA+adsorbed avidin. All culture conditions were performed in RPMI medium 1650 supplemented with 10% FBS with no IL-2 added.
Figure 8A:
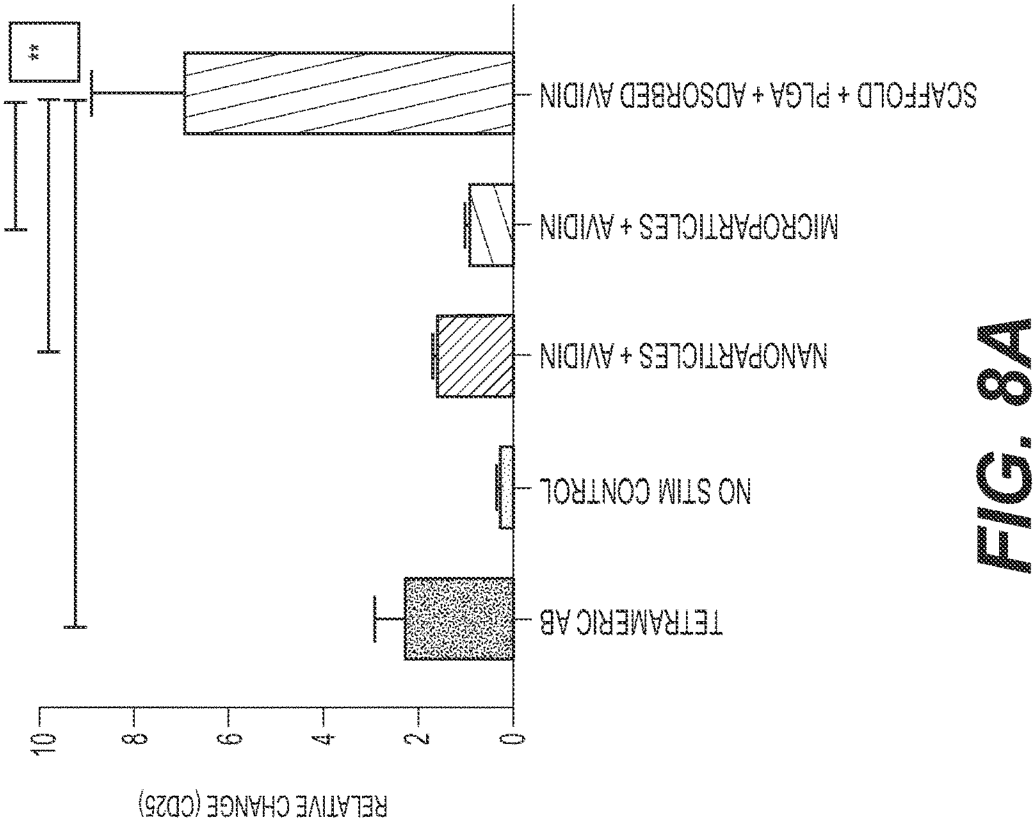
Figure 8C:
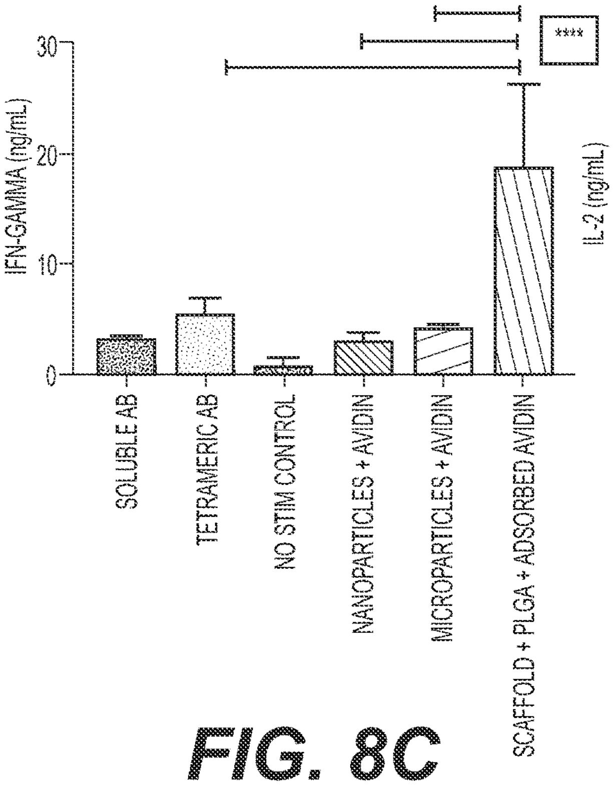
Figure 8D:
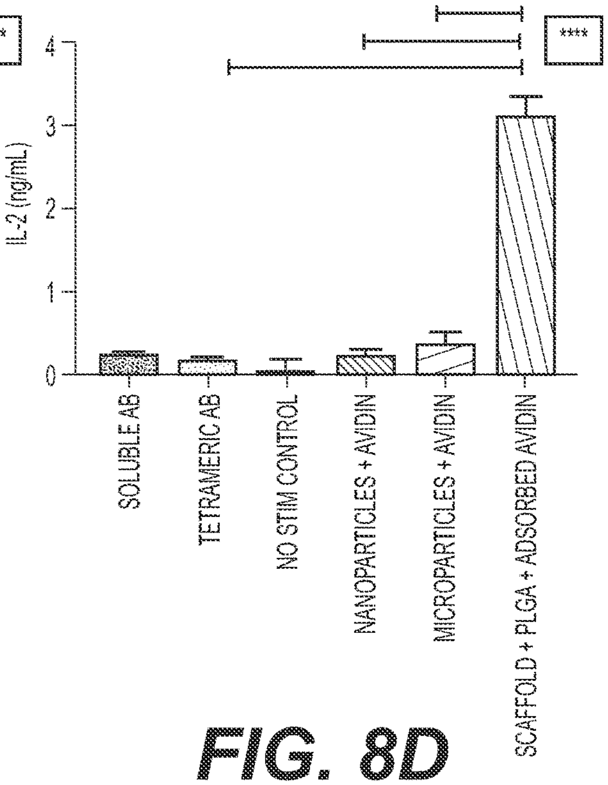
Figure 8E:
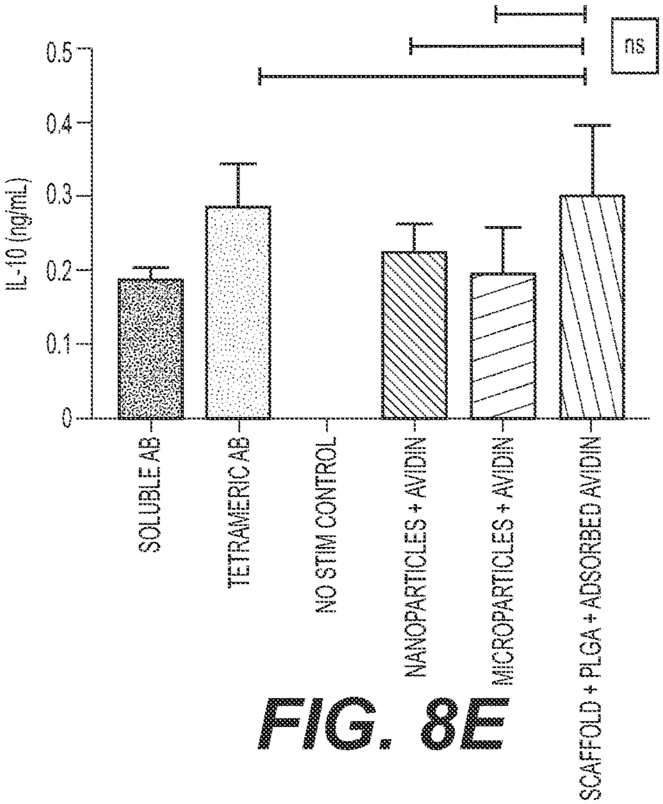

The assay design is illustrated in FIG. 7.

The scaffold refer to the base support without carbon nanotubes (CNTs). The scaffold was formed of polypropylene. CNTS are bundled CNTs. Microparticles, nanoparticles, and scaffold were decorated with avidin to facilitate attachment of biotinylated antibodies. Each test group was incubated with 100,000 splenocytes/well in 96-well u-bottom plates for 3 days and analyzed for expression of CD25 and CD44, and secretion of IFN-gamma, IL-2, and IL-10.

The results are presented in FIGS. 8A-8E. The scaffold system produced cells with the greatest amount of IL-2 receptor, and INF-gamma, and IL-2.

Example 2: Scaffold Pore Size Influences T Cell Activation

An experiment was designed to test the effect of density of T cell activation materials and pore size on the activation of T cells. Two separate densities were tested: 5 μg and 0.5 μg of antibody and anti-CD28 (equimolar). Pore sizes ranged from 300 μm to over 1000 μm. The details of the scaffolds tested are presented in Table 1. The assay designed is illustrated in FIG. 9.

TABLE 1

Details of Scaffolds Tested

| Pore Size | 310 um | 540 um | 1120 um |
|---|---|---|---|
| Specific Surface Area ($m^2$/g) | 7.3 | 6.6 | 4.0 |
| Scaffold Mass (g) | 1.0e−3 | 1.1e−3 | 1.8e−3 |
| Available Surface area ($m^2$) | 7.3e−3 | 7.3e−3 | 7.2e−3 |
| Avidin Mass (ug) | 5.0 or 0.50 | 5.0 or 0.50 | 5.0 or 0.50 |
| Avidin Density (ug/$m^2$) | 690 or 69 | 690 or 69 | 690 or 69 |

Each test group was incubated with 100,000 splenocytes/well in 96-well u-bottom plates for 3 days and analyzed for expression of CD25 (by FACS), and secretion of IFN-gamma, IL-2, and IL-10 (ELISA). The results comparing pore size at 5 μg of antibody per scaffold are presented in FIGS. 10A-10D, and 0.5 μg of antibody per scaffold are presented in FIGS. 11A-11D.

The results show that large pore sizes above 1000 μm can be detrimental for activation and proliferation. Pore sizes in the range of 100-500 μm are preferred for activation and proliferation.

IL-10 is an anti-inflammatory cytokine. It was examined here to ascertain the effect of parameters on the shift from a pro-inflammatory (activation) profile to an anti-inflammatory (suppressive) profile. Pore sizes above 500 μm appear to induce an anti-inflammatory phenotype of T cells, which is important for autoimmune applications and transplant rejection. By tuning the parameters of the system, one can shift the phenotype of cells produced for therapeutic applications ranging from cancer to autoimmune disease.

Generally, T cell activation was higher at 5 μg of antibody than at 0.5 μg of antibody: compare 10A-10D to 11A-11D.

Example 3: Scaffold Antibody Density Impacts T Cells Expansion

An additional experiment was designed to test the influence of density of T cell activating signals on T cell activation. The assay design is illustrated in FIG. 12. Each test group was incubated with 100,000 splenocytes/well in 96-well u-bottom plates for 3 days and analyzed for expression of CD25, and secretion of IFN-gamma, IL-2, and IL-10.

The results are shown in FIGS. 13A-13D. Generally, a scaffold with the same amount of antibody as a tetramer stimulating agent produces a potent phenotype characterized by increased release of IFN-gamma, IL-2, and presentation of ICD25 markers. This enhancement occurs at a specific concentration of ligand density on the scaffold.

Example 4: Paracrine Delivery of IL-2 Enhances T Cell Activation

An experiment was designed to test the impact scaffold-released IL-2 on T cell activation. The scaffold was coated with PLGA-entrapped rhIL-2. The assay design in illustrated in FIG. 14. Each test group was incubated with 100,000 splenocytes for 3 days and analyzed for expression of CD25, CD44, CD62L and secretion of IFN-gamma, IL-2, and IL-10. rhIL-2 was titrated (mass) and compared to a soluble/avidin/rhIL-2 (Tet-Exo) control. The results are shown in FIGS. 15A-15F.

Example 5: Flow Impacts T Cell Activation

An experiment was designed to test the impact of laminar flow on T cell activation. The assay design is illustrated in FIG. 16. Flow was laminar and recycled between a media reservoir and the bioreactor (line tubing: 0.32 cm ID; flow rate: ~5 ml/min) 100,000 splenocytes/well u bottom plate and 1,000,000 splenocytes/06.4 cm ID silicone tube were incubated for 3 days and analyzed for expression of CD25, CD44, % cells dividing, and secretion of IFN-gamma and IL-2. The results are presented in FIGS. 17A-17E. Flow has a significant effect, leading to upregulation of makers and secretion of cytokines needed for production of potent activated T cells.

Collectively, these experiments show that the scaffold is a better configuration of effective T cell activation and production than other artificial dendritic cells such as microparticles, nanoparticles, and tetrameric antibody. A pore diameter, such as diameter between nanoparticles, microparticles or nanotubes, between about 100 μm and about 1,200 μm, such as between about 200 μm and about 1200 μm, preferably between about 100 μm and 800 μm, such as between about 100 μm and about 500 μm, most preferably about 500 μm is preferred for activating pro-inflammatory T cells. The pore volume, volume of space between nanoparticles, microparticles or nanotubes, between $1\times10^{-6}$ cubic microns and $1\times10^{-7}$ cubic microns, preferably about $3.5\times10^{-6}$ cubic microns is preferred for activating pro-inflammatory T cells. The surface area of the pore space between nanoparticles, microparticles or nanotubes between $1\times10^{-3}$ $m^2$ and $10\times10^{-3}$ $m^2$, preferably between $5\times10^{-3}$ $m^2$ and $7\times10^{-3}$ $m^2$, is preferred. Scaffold volume between $0.5\times10^{-6}$ cubic meters and $5\times10^{-6}$ cubic meters, such as between $2.5\times10^{-6}$ cubic meters and $4.0\times10^{-6}$ cubic meters is preferred.

Antibody density plays an important role and may be between about 0.1 μg antibody per 10 square micron and about 100 μg antibody per 10 square micron. An antibody density in the range of about 1 μg antibody per 10 square micron to about 30 μg antibody per 10 square micron is preferred, and an antibody density in the range of about 0.9 μg antibody per 10 square micron to about 5 μg antibody per 10 square micron, such as about 5 μg antibody per 10 square micron, is most preferred. Flow also plays an important role in producing potent, activated T cells and these cells are characterized by an increased expression of CD62L—an important marker implicated in effective tumor immunotherapy.

Paracrine release of IL-2 from the scaffolds further enhances activation. IL-2 may be embedded in the scaffold and may be between about 0.1 ng per 10 square microns and 100 ng per 10 square microns, preferably between about 10 ng per 10 square microns and 50 ng per 10 square microns, most preferably about 20 ng per 10 square microns.

Flow rate through bioreactor may be between about about 0.1 ml/min and about 100 ml/min, preferably between about 0.1 ml/min and about 50 ml/min, such as between about 0.1 ml/min and about 5 ml/min, most preferably about 1.5 ml/min.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A device comprising:

(i) a porous thermoplastic polymeric base support ("base support");

(ii) a layer of one or more polymers and/or co-polymers ("polymer layer") adsorbed on a surface of the base support, the polymer layer comprising one or more active agents associated with, encapsulated within, surrounded by, dispersed therein, or a combination thereof; and (iii) a plurality of porous scaffolds ("the scaffolds") embedded in the polymer layer, the scaffolds comprising graphene, metallic nanoparticles, metallic microparticles, or carbon nanotubes having one or more ligands bound to or present on the surface thereof.

2. The device of claim 1, wherein the base support comprises pores, wherein a diameter of the pores is between 100 micrometers (μm) and 800 μm.

3. The device of claim 1 wherein the base support comprises a semicrystalline thermoplastic.

4. The device of claim 1 wherein the scaffold comprises graphene, metallic nanoparticles, or metallic microparticles.

5. The device of claim 4 wherein the scaffold comprises single-walled carbon nanotubes, multiwalled carbon nanotubes, or bundled carbon nanotubes.

6. The device of claim 2, wherein the scaffolds comprise a volume of space between the graphene, metallic nanoparticles, metallic microparticles, or carbon nanotubes, wherein the volume is between about $1\times10^{-6}$ $\mu m^3$–$1\times10^{-7}$ $\mu m^3$.

7. The device of claim 1, wherein one or more of the ligands comprises one or more T cell ligands.

8. The device of claim 1 wherein the one or more ligands comprises one or co-stimulatory molecules.

9. The device of claim 8 wherein the one or more co-stimulatory molecules is selected from the group consisting of CD7, B7-1 (CD80), B7-2 (CD86), PD-L1, PD-L2, 4-1BBL, OX40L, inducible co-stimulatory ligand (ICOS-L), intercellular adhesion molecule (ICAM), CD2, CD5, CD9, CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor, a ligand that specifically binds with B7-H3, antibodies that specifically bind with CD27, CD28, 4-1BB, OX40, CD30, CD40, PD-1, ICOS, lymphocyte function-associated antigen-1 (LFA-1), CD2, CD7, LIGHT, NKG2C, or B7-H3, and a ligand that specifically binds with CD83, or a combination thereof.

10. The device of claim 1 wherein the one or more ligands comprises one or more adhesion molecules.

11. The device of claim 1 wherein one or more of the ligands are linked to the scaffolds by an adaptor or Click chemistry.

12. The device of claim 1 wherein the adaptor is biotin-neutravidin and wherein the neutravidin is absorbed on the surface of the scaffolds and the biotin is conjugated to the ligand(s).

13. The device of claim 1, wherein the one or more active agents is a growth factor or cytokine.

14. The device of claim 1, wherein the ligands comprise a T cell recognition signal and costimulatory amplification signal, wherein the T cell recognition signal is anti-CD3 or a peptide/MHC complex, and wherein the costimulatory signal is anti-CD28 or anti-IBB.

15. The device of claim 1 wherein the ligands comprise a peptide/MCH II complex, an agonist for an immune checkpoint pathway receptor, or a combination thereof, wherein the immune checkpoint pathway receptor is PD-1 or CTLA-4.

16. The device of claim 1 comprising active agents comprising immunosuppressive or tolerogenic drug.

17. The device of claim 1 wherein the ligands include a ligand for an antigen presenting cell (APC) cell surface protein, wherein the ligand is CD11c, CD11d, or a combination thereof.

18. The device of claim 1 comprising active agents selected from the group consisting of a self-antigen, insect antigen, food antigen, a drug antigen, and an antigen derived from a cancer cell, bacteria, or virus.

19. A system comprising one or more of the devices of claim 1, and a gas permeable housing containing the device.

20. The system of claim 19, wherein the device is rolled-up, compressed, or a combination thereof, inside the housing.

21. The system of claim 19 comprising one or more flow lines, one or more valves or clamps, one or more ports, or a combination thereof, wherein at least one of flow lines is connectable to a subject in need of treatment.

22. The device of claim 7, wherein the one or more T cell ligands comprises one or more T cell receptor activators.

23. The device of claim 22, wherein the one or more T cell receptor activators comprises one or more polyclonal T cell activators, one or more antigen-specific T cell activators, or a combination thereof.

24. The device of claim 23, comprising one or more polyclonal T cell activators selected from the group consisting of mitogenic lectins concanavalin-A (ConA), phytohemagglutinin (PHA), pokeweed mitogen (PWM), antibodies that crosslink the T cell receptor/CD3 complex, and combinations thereof.

25. The device of claim 23, comprising one or more antigen-specific T cell activators, wherein the one or more antigen-specific T cell activators is MHC molecules bound to peptide antigens.

* * * * *